(12) United States Patent
Clark

(10) Patent No.: US 8,272,868 B2
(45) Date of Patent: Sep. 25, 2012

(54) DENTAL CURING LIGHTS AND A SEAMLESS, SINGLE LOAD CAVITY PREPARATION AND FILLING TECHNIQUE

(76) Inventor: David J. Clark, Lakewood, WA (US)

( * ) Notice: Subject to any disclaimer, the term of this patent is extended or adjusted under 35 U.S.C. 154(b) by 730 days.

(21) Appl. No.: 11/834,959

(22) Filed: Aug. 7, 2007

(65) Prior Publication Data

US 2008/0064000 A1    Mar. 13, 2008

Related U.S. Application Data

(60) Provisional application No. 60/844,333, filed on Sep. 13, 2006, provisional application No. 60/887,291, filed on Jan. 30, 2007.

(51) Int. Cl.
| | |
|---|---|
| *A61C 1/00* | (2006.01) |
| *A61C 3/00* | (2006.01) |
| *A61B 1/06* | (2006.01) |
| *F21V 5/00* | (2006.01) |
| *G01J 1/00* | (2006.01) |
| *G02F 1/00* | (2006.01) |

(52) U.S. Cl. .......................................... 433/29; 362/573
(58) Field of Classification Search .................... 433/29; 600/2–19; 606/245–246; 607/88, 90, 147; 362/269–270, 573, 572; 385/25, 26, 147
See application file for complete search history.

(56) References Cited

U.S. PATENT DOCUMENTS

| | | |
|---|---|---|
| 2,611,182 A | 9/1952 | Tofflemire |
| 3,108,377 A | 10/1963 | Meyer |
| 3,842,505 A | 10/1974 | Eames |
| 4,024,643 A | 5/1977 | Eisenberg |
| 4,259,070 A | 3/1981 | Soelberg et al. |
| 4,266,547 A * | 5/1981 | Komiya .......................... 606/15 |
| 4,337,041 A | 6/1982 | Harsany |
| 4,468,199 A | 8/1984 | Weikel |
| 4,523,909 A | 6/1985 | Lazarus |
| 4,536,155 A | 8/1985 | Ireland |
| 4,553,937 A | 11/1985 | Ropers |
| 4,601,662 A | 7/1986 | Galler |
| 4,704,087 A | 11/1987 | Dragan |
| 4,718,849 A | 1/1988 | von Weissenfluh et al. |
| 4,781,583 A | 11/1988 | Lazarus |
| 4,997,367 A | 3/1991 | Kassel |
| 5,017,140 A | 5/1991 | Ascher |
| 5,035,615 A | 7/1991 | Din |
| 5,104,317 A | 4/1992 | Riazi |
| 5,114,341 A | 5/1992 | Kassel |
| 5,201,655 A * | 4/1993 | Friedman ........................ 433/29 |
| 5,425,635 A | 6/1995 | Croll |
| 5,460,525 A | 10/1995 | Rashid |
| 5,470,331 A * | 11/1995 | Daikuzono ..................... 606/16 |

(Continued)

OTHER PUBLICATIONS

Ferracone, "Current Trends in Dental Composites", Crit Rev Oral Biol Med, 6(4), pp. 302-318, 1995.

(Continued)

*Primary Examiner* — Todd Manahan
*Assistant Examiner* — Matthew Nelson
(74) *Attorney, Agent, or Firm* — Quarles & Brady LLP

(57) ABSTRACT

There are disclosed methods for the restoration of a decayed portion of a tooth, and dental matrices, dental wedges, interdental matrix stabilizers, dental separator rings, dental curing light devices, and kits that can be used in the methods for the restoration of a decayed portion of a tooth.

16 Claims, 26 Drawing Sheets

U.S. PATENT DOCUMENTS

| | | | |
|---|---|---|---|
| 5,501,595 A | 3/1996 | Brorson | |
| 5,527,181 A | 6/1996 | Rawls et al. | |
| 5,607,302 A | 3/1997 | Garrison et al. | |
| 5,622,496 A | 4/1997 | Champagne | |
| 5,626,476 A | 5/1997 | Champagne | |
| 5,730,592 A | 3/1998 | Meyer | |
| 5,807,101 A | 9/1998 | Scalzo | |
| 5,975,906 A | 11/1999 | Knutson | |
| 5,997,302 A | 12/1999 | Alpert | |
| 6,079,978 A | 6/2000 | Kunkel | |
| 6,142,778 A | 11/2000 | Summer | |
| 6,155,823 A | 12/2000 | Nagel | |
| 6,162,055 A | 12/2000 | Montgomery et al. | |
| D439,667 S | 3/2001 | Brown | |
| 6,206,697 B1 | 3/2001 | Hugo | |
| 6,208,788 B1 * | 3/2001 | Nosov | 385/121 |
| 6,234,793 B1 | 5/2001 | Brattesani et al. | |
| 6,315,566 B1 | 11/2001 | Shen et al. | |
| 6,325,625 B1 | 12/2001 | Meyer | |
| 6,350,122 B1 | 2/2002 | Meyer | |
| 6,425,760 B1 | 7/2002 | Summer et al. | |
| 6,435,874 B1 | 8/2002 | Hughes | |
| 6,479,592 B2 | 11/2002 | Rheinberger et al. | |
| 6,482,007 B2 | 11/2002 | Stanwich et al. | |
| 6,540,072 B1 | 4/2003 | Fischer | |
| 6,599,125 B1 | 7/2003 | Freilich et al. | |
| 6,619,956 B1 | 9/2003 | Weir | |
| 6,712,608 B2 | 3/2004 | Bills | |
| 6,761,562 B2 | 7/2004 | Von Weissenfluh | |
| 6,767,955 B2 | 7/2004 | Jia | |
| 6,890,176 B2 | 5/2005 | Hahn | |
| 6,893,258 B1 | 5/2005 | Kert | |
| 6,976,841 B1 | 12/2005 | Osterwalder | |
| 7,097,364 B2 | 8/2006 | Wang | |
| 2002/0001202 A1 * | 1/2002 | Williams et al. | 362/572 |
| 2002/0119424 A1 | 8/2002 | Margeas et al. | |
| 2002/0128347 A1 | 9/2002 | Blackwell et al. | |
| 2003/0069326 A1 | 4/2003 | Stangel et al. | |
| 2003/0165793 A1 | 9/2003 | Yobel et al. | |
| 2004/0053189 A1 | 3/2004 | Friedman | |
| 2004/0229186 A1 | 11/2004 | Slone | |
| 2005/0074716 A1 | 4/2005 | Cleary et al. | |
| 2005/0089813 A1 | 4/2005 | Slone | |
| 2005/0089814 A1 | 4/2005 | Slone | |
| 2005/0231983 A1 | 10/2005 | Dahm | |
| 2005/0255428 A1 | 11/2005 | Coopersmith | |
| 2005/0287490 A1 | 12/2005 | Stookey et al. | |
| 2005/0287491 A1 | 12/2005 | Slone | |
| 2006/0009540 A1 | 1/2006 | Jia et al. | |
| 2006/0019217 A1 | 1/2006 | Yates | |
| 2006/0019220 A1 * | 1/2006 | Loebel et al. | 433/215 |
| 2006/0084029 A1 | 4/2006 | Viscomi et al. | |
| 2006/0088798 A1 | 4/2006 | Feinbloom et al. | |
| 2006/0110700 A1 | 5/2006 | Cipolla et al. | |
| 2006/0154197 A1 | 7/2006 | Gargiulo | |
| 2006/0155171 A1 | 7/2006 | Yang | |
| 2006/0188835 A1 | 8/2006 | Nagel et al. | |
| 2006/0275732 A1 | 12/2006 | Cao | |
| 2006/0275733 A1 | 12/2006 | Cao | |

OTHER PUBLICATIONS

Mount et al., "Classification and Cavity Preparation for Caries Lesions", Jan. 2005, pp. 243-249.

Bayne et al., "A Characterization of First-Generation Flowable Composites", Journal of the American Dental Association, vol. 129, May 1998, pp. 567-577.

Draga et al., "Contraction stress of flowable composite materials and their efficacy as stress-relieving layers", Journal of the American Dental Association, vol. 134, Jun. 2003, pp. 721-728.

David J. Clark et al., "Optimizing Gingival Esthetics: A Microscopic Perspective", Oral Health, Apr. 2005, pp. 116-126.

David J. Clark et al., "Definitive Diagnosis of Early Enamel and Dentinal Cracks Based on Microscopic Evaluation", Journal of Esthetic and Restorative Dentistry, vol. 15, 2003, pp. SI7-SI17.

Nordbo et al., "Saucer-shaped cavity preparations for posterior approximal resin composite restorations: Observations up to 10 years", Quintessence International, vol. 29, Issue 1, 1998, pp. 5-11.

McComb et al., "Systematic Review of Conservative Operative Caries Management Strategies", Journal of Dental Education, vol. 65, No. 10, 2001, pp. 1154-1161.

Downer et al., "How long do routine dental restorations last? A systematic review", British Dental Journal, vol. 187, No. 8, 1999, pp. 432-439.

Sensi et al., "Effect of Placement Techniques on the Marginal Adaptation of Class V Composite Restorations", The Journal of Contemporary Dental Practice, vol. 6, No. 4, Nov. 15, 2005, pp. 1-7.

* cited by examiner

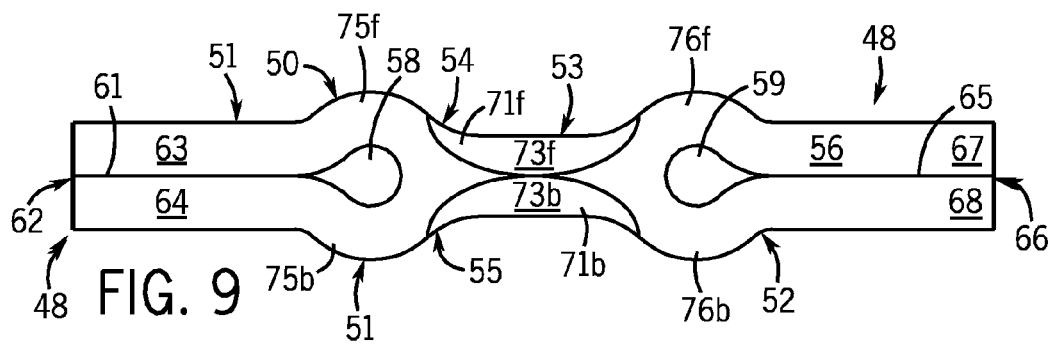
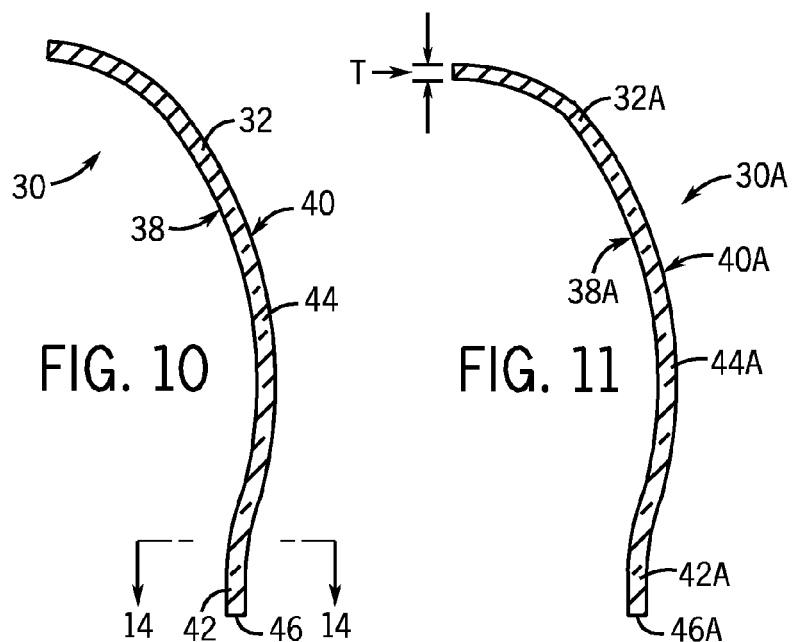
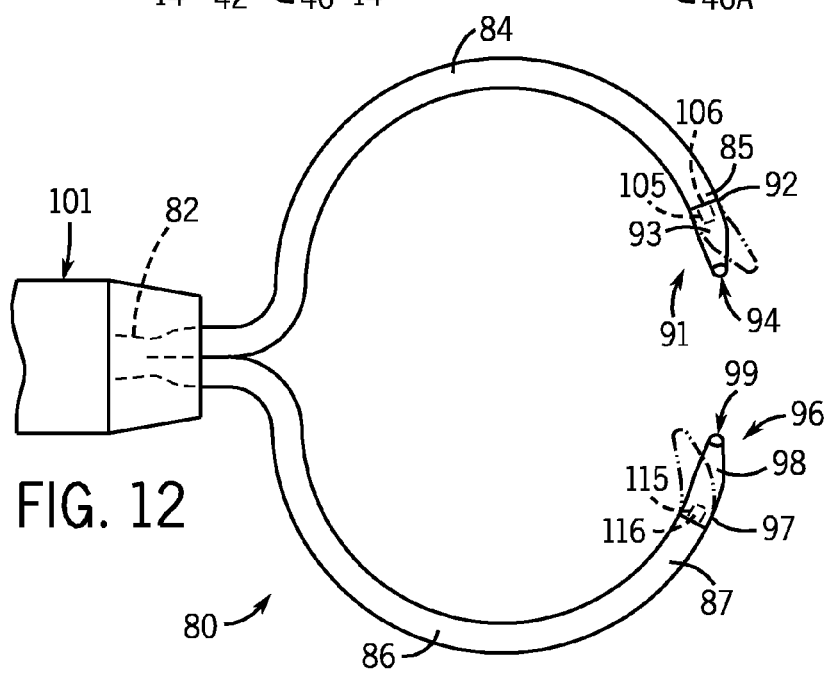

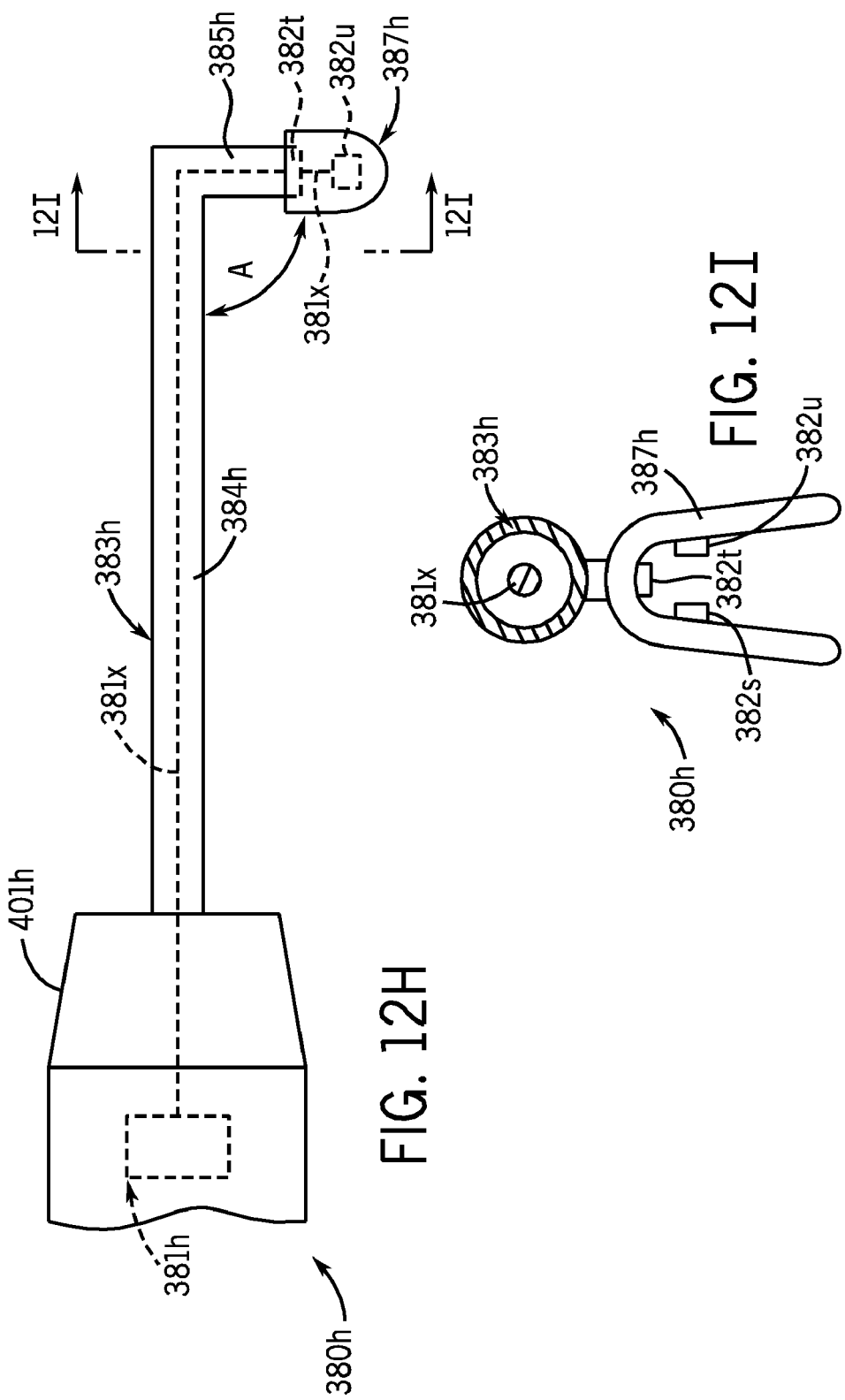

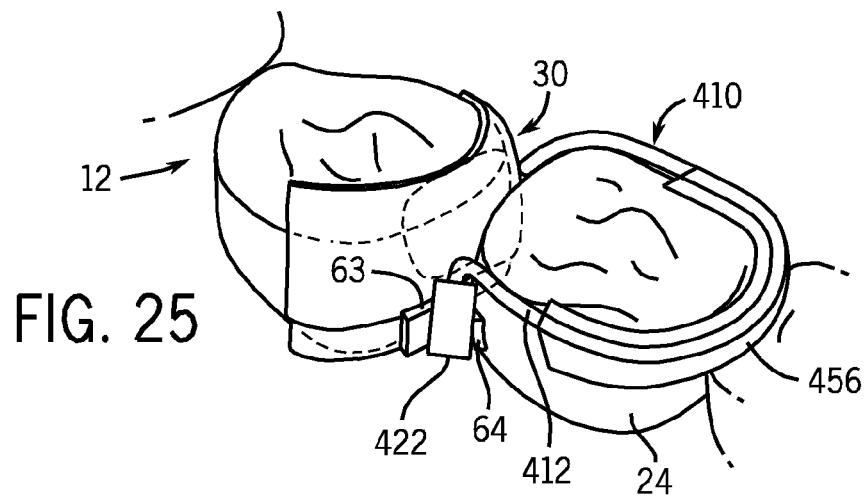
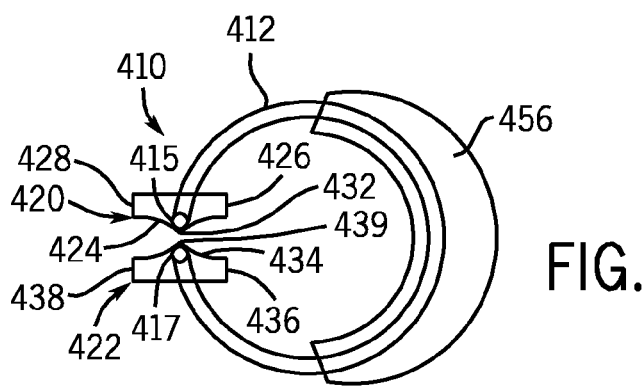
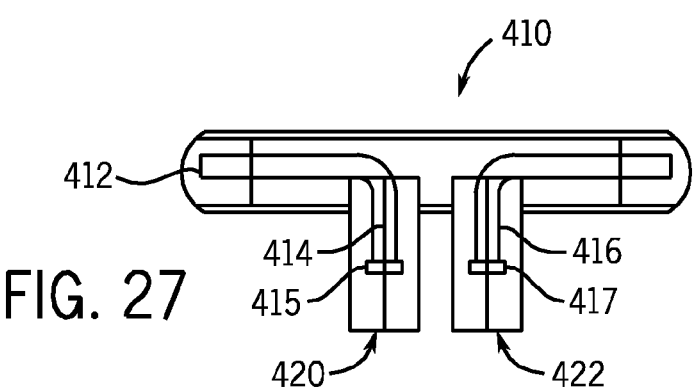
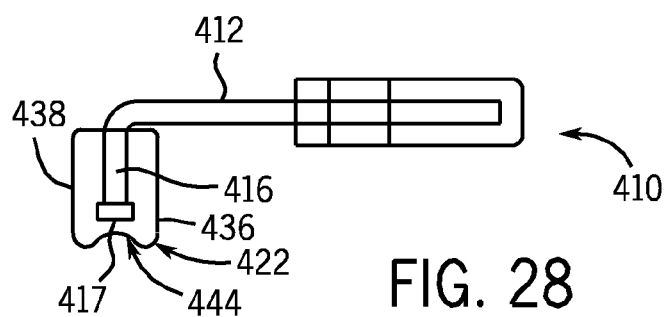

DENTAL CURING LIGHTS AND A SEAMLESS, SINGLE LOAD CAVITY PREPARATION AND FILLING TECHNIQUE

CROSS-REFERENCES TO RELATED APPLICATIONS

This application claims priority from U.S. Provisional Patent Application No. 60/844,333 filed Sep. 13, 2006 and from U.S. Provisional Patent Application No. 60/887,291 filed Jan. 30, 2007.

STATEMENT REGARDING FEDERALLY SPONSORED RESEARCH

Not Applicable.

BACKGROUND OF THE INVENTION

1. Field of the Invention

The present invention relates methods for the restoration of a decayed portion of a tooth and for dental matrices, dental wedges, interdental matrix stabilizers, dental separator rings, dental curing light devices, and kits that may be used in the methods for the restoration of a decayed portion of a tooth.

2. Description of the Related Art

Dental cavities that have spread to the dentin or have undergone cavitation are typically treated by removing the decayed portion of the tooth and thereafter filling the missing tooth structure with a restorative material such as silver (amalgam), white (resin), porcelain, or gold. Cavities that are located adjacent to neighboring teeth are called interproximal cavities.

When treating interproximal cavities, the dentist first removes the decayed portion of the side of the tooth. In order to properly deposit the restorative material on the side of the tooth without undesired leaking of the restorative material beyond the side of the tooth, the dentist places a dental matrix around at least a portion of the tooth. The dental matrix may be a metallic or plastic strip, and when the matrix is placed around at least a portion of the tooth, the matrix acts as a form for the desired shape of the restored tooth. Various dental matrix bands are shown in U.S. Pat. Nos. 6,712,608, 6,619,956, 6,350,122, 6,142,778, 6,079,978, 5,975,906, 5,807,101, 5,730,592, 5,622,496, 5,501,595, 5,460,525, 5,425,635, 5,114,341, 4,997,367, 4,781,583, 4,718,849, 4,704,087, 4,601,662, 4,553,937, 4,536,155, 4,523,909, 4,024,643, 3,842,505, 3,108,377, and 2,611,182, and U.S. Patent Application Publication Nos. 2006/0019217 and 2005/0089814. (These patents and all other patents and publications cited herein are incorporated herein by reference.) The disadvantages of these known matrix bands is that they are not truly anatomic and therefore, they must be conformed to the tooth by pressure or other means. As a result, these matrixes are inefficient in that more dentist time is needed to complete the restoration, and the final result may be a non-anatomic restoration.

One or more dental wedges may be used to spread adjacent teeth to allow the dental matrix to be positioned between the adjacent teeth. The dental wedge(s) may also function as a matrix stabilizer that maintains the matrix in a desired position with respect to the tooth to be restored. Various dental wedges are shown in U.S. Pat. Nos. 6,890,176, 6,761,562, 6,482,007, 6,435,874, 6,425,760, 6,234,792, 5,527,181, 5,104,317, 4,468,199, 4,337,041, 4,259,070 and D439,667.

A dental separator ring may also be used when filling interproximal cavities. The separator ring applies pressure against the adjacent teeth to force the adjacent teeth apart to allow a dental matrix to be positioned between the adjacent teeth. The dental separator ring may also include specially configured ends that also function as a matrix stabilizer that maintains the matrix in a desired position with respect to the tooth to be restored. Example dental separator rings can be found in U.S. Pat. Nos. 6,325,625, 6,206,697 and 5,607,302.

A dentist may choose to use curable restorative material to fill the interproximal cavity. Many curable dental restorative materials harden by polymerization reactions initiated by ultraviolet light or blue wavelengths. After placing curable restorative material between the matrix and the tooth being restored and in contact with the tooth being restored, the dentist uses a dental curing light device to direct light onto the curable restorative material to initiate polymerization of the curable restorative material. The curable restorative material then hardens in the cavity. Example dental lights and light curing devices can be found in U.S. Pat. Nos. 7,097,364, 6,976,841, 6,155,823, 6,162,055, and 5,017,140 and U.S. Patent Application Publication Nos. 2006/0275733, 2006/0275732, 2006/018835, 2006/0155171, 2006/0154197, 2006/0110700, 2006/0088798, 2004/0229186 and 2004/0053189.

Even though various dental matrices, dental wedges and dental curing light devices are available, there is a still a need for improved methods for the restoration of a decayed portion of a tooth and for improved dental matrices, dental wedges, interdental matrix stabilizers, separator rings, dental curing light devices, and kits that may be used in methods for the restoration of a decayed portion of a tooth.

SUMMARY OF THE INVENTION

The invention meets the foregoing needs by providing improved methods, dental matrices, dental wedges, interdental matrix stabilizers, dental separator rings, dental curing light devices, and kits for the restoration of a decayed portion of a tooth.

The invention provides a method for the restoration of a tooth having an original shape including a top surface and an interproximal surface. In the method, a portion of the top surface of the tooth and a portion of the interproximal surface of the tooth are removed using conventional dental instruments to form a hollow cavity preparation that extends from the top surface to the interproximal surface of the tooth. The hollow cavity preparation is preferably saucer shaped wherein the cavity preparation does not extend inward more than two millimeters from the interproximal surface of the tooth. The removed portion of the interproximal surface of the tooth is then surrounded with a sectional translucent (preferably transparent) anatomic dental matrix. The actual anatomic shapes of the matrix are created from scans of natural teeth, molds of natural teeth, and/or molds of tooth models. Thus, by "anatomic", it is meant that the matrix has an inner surface that conforms to the shape of the outer surface of the region of the natural tooth being restored.

A lightly filled or unfilled light curable resin tooth bonding agent is then applied to the tooth covering the entire cavity preparation. The resin tooth bonding agent is then air thinned except on the tooth surface where a small pool of resin tooth bonding agent is maintained. The resin tooth bonding agent is not light cured at this point. A light-curable flowable composite is injected into the cavity preparation to create a pool of the flowable composite and the tooth bonding agent in the cavity preparation. A light-curable paste composite resin is then extruded into the pool of the flowable composite and the tooth bonding agent before light curing the pool of the flowable composite. The flowable composite and the paste composite resin and the tooth bonding agent contained in the cavity preparation are then light cured simultaneously. The result is an injection molded restoration. Optionally, a curable base material can be loaded into deeper cavity preparations to cover the dentin. The curable base material is cured before beginning the injection molding process. Preferably, the cured base material is about two millimeters from the projected outer tooth surface of the restoration.

In one version of the method, a pre-wedging step occurs in that a wedge is inserted between the interproximal surfaces of the teeth before beginning the cavity preparation. This creates a gap between the interproximal surface of the tooth being restored and the interproximal surface of a second tooth, and also protects and compresses the soft tissue and rubber dam. The wedge is removed, and thereafter the removed portion of the interproximal surface of the tooth is surrounded with the matrix. A translucent elastic matrix stabilizer can also be positioned in contact with the matrix to maintain contact of the matrix with the tooth being restored. A separator ring can also be positioned in contact with the matrix stabilizer to create separation between the interproximal surface of the tooth being restored and an interproximal surface of a second tooth adjacent the tooth being restored.

During the curing process, light is directed at the top surface of the tooth, the buccal portion of the interproximal surface of the tooth, and the lingual portion of the interproximal surface of the tooth. Preferably, curing light is simultaneously directed at the buccal portion and the lingual portion of the interproximal surface of the tooth.

Thus, in the method of the invention, a single load of restorative material can be cured in a single step to produce a seamless cavity restoration.

In one aspect, the invention provides a method for the restoration of a tooth having an original shape including a top surface and an interproximal surface. In the method, a portion of the top surface of the tooth and a portion of the interproximal surface of the tooth are removed to form a hollow cavity preparation which extends from the top surface to the interproximal surface of the tooth. The removed portion of the interproximal surface of the tooth is surrounded with a matrix. A light-curable resin tooth bonding agent is placed into the cavity preparation. A light-curable flowable composite is then injected into the cavity preparation to create a pool of the flowable composite in the cavity preparation. A light-curable paste composite resin is then extruded into the pool of the flowable composite before light curing the pool of the flowable composite. The bonding agent and the flowable composite and the paste composite resin contained in the cavity preparation are then simultaneously light cured.

The dental practitioner may utilize an acid etching step with liquid and/or gel phosphoric acid treatment before placing the bonding agent into the cavity preparation. Preferably, the bonding agent is self-etching. The method can include a pre-wedging step including inserting a wedge pre-operatively between the interproximal surface of the tooth being restored and an interproximal surface of a second tooth adjacent the tooth being restored to separate the tooth being restored and the second tooth and to protect non-diseased surfaces between the interproximal surface of the tooth being restored and the interproximal surface of the second tooth. The cavity preparation can then be formed, and the wedge removed.

The dental practitioner may position a translucent elastic matrix stabilizer in contact with the matrix to maintain contact of the matrix with the tooth being restored and/or to create separation of the teeth. The dental practitioner may also position a separator ring with a transparent and anatomic interproximal zone in contact with the matrix stabilizer and matrix to create separation between the interproximal surface of the tooth being restored and an interproximal surface of a second tooth adjacent the tooth being restored.

In the light curing step, the dental practitioner may simultaneously direct light at the top surface of the tooth, at a buccal portion of the interproximal surface of the tooth, and at a lingual portion of the interproximal surface of the tooth. Alternatively, the dental practitioner may direct light at the top surface of the tooth, and then thereafter simultaneously direct light at a buccal portion and a lingual portion of the interproximal surface of the tooth. In one exemplary version of the method, light is directed from a first light guide at a buccal portion of the interproximal surface of the tooth, and directed from a second light guide at a lingual portion of the interproximal surface of the tooth, wherein the first light guide and the second light guide are hinged at a dental curing light housing.

The hollow cavity preparation is preferably saucer shaped. Preferably, the cavity preparation does not extend inward more than two millimeters from the interproximal surface of the tooth. Preferably, the hollow cavity preparation is saucer shaped and in an occlusal view has a first serpentine outline from a first cavity margin to an intermediate point of the cavity preparation and a second serpentine outline from a second cavity margin to the intermediate point of the cavity preparation. Preferably, the hollow cavity preparation is saucer shaped and in a gingival view has a first serpentine outline from a first cavity margin to an intermediate point of the cavity preparation and has a second serpentine outline from a second cavity margin to the intermediate point of the cavity preparation. Preferably, the hollow cavity preparation is saucer shaped and in a buccal view has a first serpentine outline from a first cavity margin to an intermediate point of the cavity preparation and has a second serpentine outline from a second cavity margin to the intermediate point of the cavity preparation. Preferably, the hollow cavity preparation is saucer shaped and in a lingual view has a first serpentine outline from a first cavity margin to an intermediate point of the cavity preparation and has a second serpentine outline from a second cavity margin to the intermediate point of the cavity preparation. Preferably, the hollow cavity preparation is saucer shaped in an occlusal view, and/or buccal view, and/or lingual view, and/or gingival view.

Various forms of the matrix are suitable for the method. For example, the matrix can be translucent, sectional, and/or anatomically shaped. The matrix can be tooth specific, or the matrix can be tooth type specific, or the matrix can be tooth surface specific.

In one exemplary version of the method, further flowable composite and/or paste composite resin are not added after the first load of flowable composite and paste composite resin such that the method produces a single cured layer load and layer of flowable composite and paste composite resin. Advantageously, the filled cavity preparation is seamless, injection molded, and/or not layered. In another version of the method, a curable base/liner material is loaded into the cavity preparation, the base/liner material is cured, and thereafter the light-curable flowable composite is injected into the cavity preparation to create the pool of the flowable composite in the cavity preparation. Preferably, an external surface of the cured base/liner material is two millimeters or less from a projected external interproximal filling surface of the tooth.

In another aspect, the invention provides a first embodiment of an interproximal dental matrix stabilizer. The interproximal dental matrix stabilizer includes an elongated elastic body having a first end portion, a second opposite end portion, a middle portion connecting the first end portion and the second end portion, a first side surface, a second side surface, a top surface and a bottom surface. The first end portion has a first throughhole extending from the top surface to the bottom surface, and the second end portion has a second throughhole extending from the top surface to the bottom surface. The first end portion includes an area of material weakness extending toward the top surface and extending toward the bottom surface and extending toward a first end surface of the body whereby the first end portion can be separated into separate end members by application of a separation force at the area of material weakness, which can extend from the first throughhole to the first end surface of the body. Preferably, the body comprises a translucent material. Most preferably, the body comprises a translucent material. Also, the interproximal dental matrix stabilizer can be made with translucent elastomeric material with a round and/or tapered cross section. The interproximal dental matrix stabilizer can be used in place of traditional wooden, plastic or rubber wedges and also allows for better photon transfer from a curing light. Preferably, the second end portion includes a second area of material weakness extending toward the top surface and extending toward the bottom surface and extending toward a second end surface of the body whereby the second end portion can be separated into separate end members by application of a separation force at the second area of material weakness.

In one exemplary form, the top surface of the body includes a first pair of upper side-by-side depressions in the middle portion of the body, and the bottom surface of the body includes at least one concavity in the middle portion of the body. In another exemplary form, the first pair of upper side-by-side depressions include an inwardly curved inner surface, and the bottom surface of the body includes a concavity having an inwardly curved inner surface. In yet another exemplary form, the first side surface of the body includes a first curved protrusion located near an intermediate vertical plane of the body. In still another exemplary form, the first side surface of the body includes a first curved protrusion located near the first throughhole, and the second side surface of the body includes a second curved protrusion located near the second throughhole.

In yet another exemplary form, the first side surface of the body includes a first curved protrusion located near the first throughhole, and the second side surface of the body includes a second curved protrusion located near the first throughhole. In still another exemplary form, the separate end members have a rectangular vertical cross-section.

In another aspect, the invention provides a second embodiment of an interproximal dental matrix stabilizer. The interproximal dental matrix stabilizer includes an elongated elastic body having a first end portion, a second opposite end portion, a middle portion connecting the first end portion and the second end portion, a first side surface, a second side surface, a top surface and a bottom surface. The first side surface of the body includes a first outwardly extending protrusion on the first end portion wherein the first outwardly extending protrusion is spaced inward from a first end surface of the body. The first side surface of the body further includes a second outwardly extending protrusion on the second end portion wherein the second outwardly extending protrusion is spaced inward from a second end surface of the body. Preferably, the body comprises a translucent material.

In one exemplary form, the first end portion includes a first section adjacent the first outwardly extending protrusion and a second section connected to the first section of the first end portion opposite the first outwardly extending protrusion wherein the second section of the first end portion extends laterally outward from the first section of the first end portion, and the second end portion includes a first section adjacent the second outwardly extending protrusion and a second section connected to the first section of the second end portion opposite the second outwardly extending protrusion wherein the second section of the second end portion extends laterally outward from the first section of the second end portion. Preferably, the second section of the first end portion is generally disc shaped, and the second section of the second end portion is generally disc shaped. Preferably, the top surface includes indicia for facilitating placement of the interproximal dental matrix stabilizer between approximating teeth with the top surface positioned away from the gingiva.

In another exemplary form, the second side surface of the body includes a third outwardly extending protrusion on the first end portion, and the second side surface of the body further includes a fourth outwardly extending protrusion on the second end portion. In yet another exemplary form, the first end portion includes an area of material weakness extending toward the top surface and extending toward the bottom surface and extending toward a first end surface of the body whereby the first end portion can be separated into separate first end members by application of a separation force at the area of material weakness, and the second end portion includes a second area of material weakness extending toward the top surface and extending toward the bottom surface and extending toward a second end surface of the body whereby the second end portion can be separated into separate second end members by application of a separation force at the second area of material weakness. Preferably, the first separate end members and the second separate end members have a rectangular vertical cross-section. In still another exemplary form, the first side surface of the body includes a first curved protrusion located near an intermediate vertical plane of the body. In yet another exemplary form, the bottom surface of the body includes a concavity. The concavity can have a longitudinal axis and a lateral axis transverse to the longitudinal axis wherein the longitudinal axis extends toward the first end portion and the second end portion and the longitudinal axis is longer than the lateral axis.

In yet another aspect, the invention provides a sectional translucent anatomic dental matrix for providing a form for filling a hollow cavity preparation in a tooth. The matrix includes a curved strip of material. The strip has a length from a first end to a second end sufficient to extend beyond a first vertical junction of the cavity preparation and a surface of the tooth and to extend beyond a second vertical junction of the cavity preparation and the surface of the tooth to create the form for filling the cavity preparation, which may be interproximal. The strip has a horizontally concave side surface and a horizontally convex side surface, and the strip has a base portion and an upper portion integral with and extending upward from the base portion. The concave side surface is anatomic in that the concave side surface has an inner surface that that conforms to the shape of the outer surface of the region of the natural tooth being restored. Also, the concave side surface and the convex side surface can extend from the first end to the second end. A first thickness between the concave side surface and the convex side surface at a first plane horizontal to the strip is less than a second thickness between the concave side surface and the convex side surface at a second plane horizontal to the strip wherein the second plane is below the first plane.

In one exemplary form, the horizontally concave side surface forming the base portion is not vertically concave, and the horizontally concave side surface forming the upper portion is vertically concave. In another exemplary form, the strip thickness between the concave side surface and the convex side surface at planes horizontal to the strip decreases from lower to upper sections of the upper portion of the strip. In yet another exemplary form, the concave side surface and the convex side surface extend from the first end to the second end.

Preferably, the material of the curved strip is translucent. In one form, the material is metallic. In another form, the material is polymeric. One non-limiting advantage to the translucent sectional matrix is that it allows a single load of composite material, which alleviates both the problems of (i) voids between the two millimeter separately loaded and cured increments required with composite material and a metal matrix and (ii) the additional time wasted to place and light cure several layers of composite filling material.

In one exemplary form, the matrix is sectional and anatomically shaped. In another exemplary form, the matrix is tooth specific. In yet another exemplary form, the matrix is tooth type specific. In still another exemplary form, the matrix is tooth surface specific.

In still another aspect, the invention provides a sectional translucent anatomic dental matrix for providing a form for filling a hollow cavity preparation in a tooth. The dental matrix includes a curved strip of material. The strip has a length from a first end to a second end sufficient to extend beyond a first vertical junction of the cavity preparation and a surface of the tooth and to extend beyond a second vertical junction of the cavity preparation and the surface of the tooth to create the form for filling the cavity preparation, which may be interproximal. The strip has a first side surface and a second side surface. The first side surface has an intermediate horizontally convex section between a first horizontally concave section and a second horizontally concave section. Preferably, the strip has a base portion and an upper portion integral with and extending upward from the base portion, and the base portion includes the horizontally convex section, the first horizontally concave section and the second horizontally concave section.

In one exemplary form, the strip thickness between the first side surface and the second side surface at planes horizontal to the strip decreases from lower to upper sections of the upper portion of the strip. In another exemplary form, the first side surface forming the base portion is not vertically concave, and the second side surface forming the upper portion is vertically concave. In yet another exemplary form, a first thickness between the first side surface and the second side surface at a first plane horizontal to the strip is less than a second thickness between the first side surface and the second side surface at a second plane horizontal to the strip, the second plane being below the first plane.

Preferably, the material of the curved strip is translucent. In one form, the material is metallic. In another form, the material is polymeric.

In one exemplary form, the matrix is sectional and anatomically shaped. In another exemplary form, the matrix is tooth specific. In yet another exemplary form, the matrix is tooth type specific. In still another exemplary form, the matrix is tooth surface specific.

In yet another aspect, the invention provides a dental matrix for providing a form for filling a first hollow interproximal cavity preparation in a first tooth and a second hollow interproximal cavity preparation in a second tooth. The matrix includes a first curved strip of a first material. The first strip has a length from a first end to a second end sufficient to extend beyond a first vertical junction of the first interproximal cavity preparation and an interproximal surface of the first tooth and to extend beyond a second vertical junction of the first interproximal cavity preparation and the interproximal surface of the first tooth to create the form for filling the first interproximal cavity preparation. The first strip has a first side surface and a second side surface. The matrix also includes a second curved strip of a second material. The second strip has a first side surface and a second side surface. The second strip has a length from a first end to a second end sufficient to extend beyond a first vertical junction of the second interproximal cavity preparation and an interproximal surface of the second tooth and to extend beyond a second vertical junction of the second interproximal cavity preparation and the interproximal surface of the second tooth to create the form for filling the second interproximal cavity preparation. The first curved strip and the second curved strip are joined at a middle portion of the multi-strip matrix, and the middle portion of the matrix has a thickness less than two times a thickness of the first end of the first curved strip. Preferably, the first curved strip and the second curved strip have an arc of less than 270 degrees.

In one exemplary form, the first curved strip and the second curved strip are translucent. The first material and the second material can be metallic, or the first material and the second material can be polymeric.

In one exemplary form, the matrix is sectional and anatomically shaped. In another exemplary form, the matrix is tooth specific. In yet another exemplary form, the matrix is tooth type specific. In still another exemplary form, the matrix is tooth surface specific.

In one exemplary form, the first curved strip has a first horizontally concave side surface and a first horizontally convex side surface, and the second curved strip has a second horizontally concave side surface and a second horizontally convex side surface. The concave side surfaces of the first and second strip are anatomic in that the concave side surfaces have an inner surface that that conforms to the shape of the outer surface of the region of the natural tooth being restored. Also, the concave side surface and the convex side surface can extend from the first end to the second end of the first strip and the second strip. In another exemplary form, the first strip has a first base portion and a first upper portion integral with and extending upward from the first base portion, the first horizontally concave side surface forming the first base portion is not vertically concave, the first horizontally concave side surface forming the first upper portion is vertically concave, the second strip has a second base portion and a second upper portion integral with and extending upward from the second base portion, the second horizontally concave side surface forming the second base portion is not vertically concave, and the second horizontally concave side surface forming the second upper portion is vertically concave.

In another aspect, the invention provides a method for filling a first hollow interproximal cavity preparation in a first tooth and a second hollow interproximal cavity preparation in an adjacent second tooth using this multi-strip matrix. In the method, a matrix stabilizer is placed between an interproximal surface of the first tooth and an interproximal surface of the second tooth, and the multi-strip matrix is placed between the first tooth and the second tooth such that the first curved strip is placed in contact with the interproximal surface of the first tooth, and the second curved strip is placed in contact with the interproximal surface of the second tooth, and the matrix stabilizer is placed between the first curved strip and the second curved strip and in contact with the first curved strip and the second curved strip. The cavity preparations may then be filled.

In yet another aspect, the invention provides a method for filling a first hollow interproximal cavity preparation in a first tooth and a second hollow interproximal cavity preparation in an adjacent second tooth using this multi-strip matrix. A matrix stabilizer is placed between an interproximal surface of the first tooth and an interproximal surface of the second tooth. The matrix stabilizer is placed in tension to create a middle portion of decreased cross-section in the matrix stabilizer. The multi-strip matrix is placed between the first tooth and the second tooth such that the first curved strip is placed in contact with the interproximal surface of the first tooth, and the second curved strip is placed in contact with the interproximal surface of the second tooth, and the matrix stabilizer is placed between the first curved strip and the second curved strip. The tension is then released on the matrix stabilizer such that the matrix stabilizer is placed in contact with the first curved strip and the second curved strip. The cavity preparations may then be filled.

In still another aspect, the invention provides a method for filling a first hollow interproximal cavity preparation in a first tooth and a second hollow interproximal cavity preparation in an adjacent second tooth using this multi-strip matrix. The multi-strip is placed between the first tooth and the second tooth such that the first curved strip is placed adjacent the interproximal surface of the first tooth and the second curved strip is placed adjacent the interproximal surface of the second tooth. At least one dental wedge is then placed between the first curved strip and the second curved strip and in contact with the first curved strip and the second curved strip thereby biasing the first curved strip into contact with the interproximal surface of the first tooth, and biasing the second curved strip into contact with the interproximal surface of the second tooth. The cavity preparations may then be filled.

In yet another aspect, the invention provides a dental matrix for providing a form for filling a first hollow interproximal cavity preparation in a first tooth and a second hollow interproximal cavity preparation in a second tooth. The matrix includes a first curved strip of a first material. The first strip has a length from a first end to a second end sufficient to extend beyond a first vertical junction of the first interproximal cavity preparation and an interproximal surface of the first tooth and to extend beyond a second vertical junction of the first interproximal cavity preparation and the interproximal surface of the first tooth to create the form for filling the first interproximal cavity preparation. The first strip has a first side surface and a second side surface, and the first curved strip has a first throughhole. The matrix also includes a second curved strip of a second material. The second strip has a first side surface and a second side surface. The second strip has a length from a first end to a second end sufficient to extend beyond a first vertical junction of the second interproximal cavity preparation and an interproximal surface of the second tooth and to extend beyond a second vertical junction of the second interproximal cavity preparation and the interproximal surface of the second tooth to create the form for filling the second interproximal cavity preparation. The second curved strip has a second throughhole. In the matrix, the first curved strip and the second curved strip are joined at a middle portion of the matrix. Preferably, the first curved strip and the second curved strip have an arc of less than 270 degrees. Preferably, the middle portion of the matrix has a thickness less than two times a thickness of the first end of the first curved strip.

In one exemplary form, the first curved strip and the second curved strip are translucent. The first material and the second material can be metallic, or the first material and the second material can be polymeric.

In one exemplary form, the matrix is sectional and anatomically shaped. In another exemplary form, the matrix is tooth specific. In yet another exemplary form, the matrix is tooth type specific. In still another exemplary form, the matrix is tooth surface specific.

In another exemplary form, the first curved strip has a first horizontally concave side surface and a first horizontally convex side surface, and the second curved strip has a second horizontally concave side surface and a second horizontally convex side surface. In yet another exemplary form, the first strip has a first base portion and a first upper portion integral with and extending upward from the first base portion, the first horizontally concave side surface forming the first base portion is not vertically concave, the first horizontally concave side surface forming the first upper portion is vertically concave, the second strip has a second base portion and a second upper portion integral with and extending upward from the second base portion, the second horizontally concave side surface forming the second base portion is not vertically concave, and the second horizontally concave side surface forming the second upper portion is vertically concave. In still another exemplary form, the first throughhole and the second throughhole are aligned to create a passageway. In yet another exemplary form, the first throughhole and the second throughhole are aligned, and a membrane is positioned between the first throughhole and the second throughhole.

In still another aspect, the invention provides a method for filling a first hollow interproximal cavity preparation in a first tooth and a second hollow interproximal cavity preparation in an adjacent second tooth using this multi-strip matrix. A matrix stabilizer is placed between an interproximal surface of the first tooth and an interproximal surface of the second tooth. The multi-strip matrix is placed between the first tooth and the second tooth such that the first curved strip is placed in contact with the interproximal surface of the first tooth, the second curved strip is placed in contact with the interproximal surface of the second tooth, and the matrix stabilizer is placed between the first curved strip and the second curved strip and in contact with the first curved strip and the second curved strip. The cavity preparations may then be filled.

In yet another aspect, the invention provides a method for filling a first hollow interproximal cavity preparation in a first tooth and a second hollow interproximal cavity preparation in an adjacent second tooth. A matrix stabilizer is placed between an interproximal surface of the first tooth and an interproximal surface of the second tooth. The matrix stabilizer is placed in tension to create a middle portion of decreased cross-section in the matrix stabilizer. The multi-strip matrix is inserted between the first tooth and the second tooth such that the first curved strip is placed in contact with the interproximal surface of the first tooth, the second curved strip is placed in contact with the interproximal surface of the second tooth, and the matrix stabilizer is placed between the first curved strip and the second curved strip. The tension on the matrix stabilizer is released such that the matrix stabilizer is placed in contact with the first curved strip and the second curved strip. The cavity preparations may then be filled.

In still another aspect, the invention provides a method for filling a first hollow interproximal cavity preparation in a first tooth and a second hollow interproximal cavity preparation in an adjacent second tooth using this multi-strip matrix. The multi-strip matrix is inserted between the first tooth and the second tooth such that the first curved strip is placed adjacent the interproximal surface of the first tooth, and the second curved strip is placed adjacent the interproximal surface of the second tooth. At least one dental wedge is placed between the first curved strip and the second curved strip and in contact with the first curved strip and the second curved strip thereby biasing the first curved strip into contact with the interproximal surface of the first tooth, and biasing the second curved strip into contact with the interproximal surface of the second tooth. The cavity preparations may then be filled.

In yet another aspect, the invention provides a dental matrix kit for providing a form for filling a first hollow interproximal cavity preparation in a first tooth and a second hollow interproximal cavity preparation in a second tooth. The matrix kit includes a first curved strip of a first material. The first strip has a length from a first end to a second end sufficient to extend beyond a first vertical junction of the first interproximal cavity preparation and an interproximal surface of the first tooth and to extend beyond a second vertical junction of the first interproximal cavity preparation and the interproximal surface of the first tooth to create the form for filling the first interproximal cavity preparation. The first strip has a first side surface and a second side surface. The matrix kit includes a second curved strip of a second material. The second strip has a first side surface and a second side surface. The second strip has a length from a first end to a second end sufficient to extend beyond a first vertical junction of the second interproximal cavity preparation and an interproximal surface of the second tooth and to extend beyond a second vertical junction of the second interproximal cavity preparation and the interproximal surface of the second tooth to create the form for filling the second interproximal cavity preparation. The second curved strip has a throughhole. Preferably, the first curved strip and the second curved strip are sectional and have an arc of less than 270 degrees.

In one exemplary form, the first curved strip and the second curved strip are translucent. The first material and the second material can be metallic, or the first material and the second material can be polymeric.

In one exemplary form, the first curved strip and the second curved strip are anatomically shaped. In another exemplary form, the first curved strip and the second curved strip are tooth specific. In yet another exemplary form, the first curved strip and the second curved strip are tooth type specific. In still another exemplary form, the first curved strip and the second curved strip are tooth surface specific.

In one exemplary form, the first curved strip has a first horizontally concave side surface and a first horizontally convex side surface, and the second curved strip has a second horizontally concave side surface and a second horizontally convex side surface. In another exemplary form, the first strip has a first base portion and a first upper portion integral with and extending upward from the first base portion, the first horizontally concave side surface forming the first base portion is not vertically concave, the first horizontally concave side surface forming the first upper portion is vertically concave, the second strip has a second base portion and a second upper portion integral with and extending upward from the second base portion, the second horizontally concave side surface forming the second base portion is not vertically concave, and the second horizontally concave side surface forming the second upper portion is vertically concave.

In yet another aspect, the invention provides a method for preparing a form for filling a first hollow interproximal cavity preparation in a first tooth and a second hollow interproximal cavity preparation in a second tooth. In the method, a first horizontally convex side surface of the first curved strip of the dental matrix kit is placed against a second horizontally convex side surface of the second curved strip of the dental matrix kit. A portion of the first curved strip of the dental matrix kit may also be positioned in the throughhole of the second curved strip of the dental matrix kit.

In another aspect, the invention provides a dental curing light. The curing light includes an electrical power supply, a first light guide in optical communication with at least one light source in electrical communication with the electrical power supply, and a second light guide in optical communication with at least one light source in electrical communication with the electrical power supply. The first light guide and the second light guide are connected to a housing, and at least one of the first light guide and the second light guide is hinged to the housing for movement with respect to the housing. Preferably, the first light guide and the second light guide are both hinged to the housing for movement with respect to the housing.

In one exemplary form, the first light guide has a first distal tip, the second light guide has a second distal tip, and the first tip and the second tip are angled toward each other. In another exemplary form, the first light guide and the second light guide are normally biased into a relaxed position in which the first distal tip and the second distal tip are a first distance apart, and the first light guide and the second light guide have an outwardly flexed position in which the first distal tip and the second distal tip are a second distance apart, the second distance being greater than the first distance. Preferably, the first distance is about 4 to about 15 millimeters.

In one exemplary form, the first light guide is in optical communication with a first light source in electrical communication with the electrical power supply, the second light guide is in optical communication with a second light source in electrical communication with the electrical power supply, the first light source is located in the first distal end of the first light guide, and the second light source is located in the second distal end of the second light guide. In another exemplary form, the dental curing light includes a third light guide in optical communication with at least one light source in electrical communication with the electrical power supply. The third light guide may be hinged at a dental curing light housing.

In yet another aspect, the invention provides a method for the restoration of a tooth having a hollow cavity preparation in an interproximal surface of the tooth. In the method, a light-curable restorative material is placed in the cavity preparation. Light is directed from the first light guide of the dental curing light at a buccal portion of the restorative material in the cavity preparation, light is simultaneously directed from the second light guide of the dental curing light at a lingual portion of the restorative material in the cavity preparation.

In another aspect, the invention provides a dental curing light including an electrical power supply, a first light guide in optical communication with at least one light source in electrical communication with the electrical power supply, a first light transmitting tip connected to a first distal end of the first light guide, the first tip including a first tip section having a diameter less than a diameter of the first distal end of the first light guide, a second light guide in optical communication with at least one light source in electrical communication with the electrical power supply and a second light transmitting tip connected to a second distal end of the second light guide, the second tip including a second tip section having a diameter less than a diameter of the second distal end of the second light guide. Preferably, the first tip and the second tip are angled toward each other.

In one exemplary form, the first light guide is in optical communication with a first light source in electrical communication with the electrical power supply, and the second light guide is in optical communication with a second light source in electrical communication with the electrical power supply. The first light source can be located in the first distal end of the first light guide, and the second light source can be located in the second distal end of the second light guide.

In another exemplary form, the first light guide and the second light guide are connected to a housing, and at least one of the first light guide and the second light guide is hinged to the housing for movement with respect to the housing. In yet another exemplary form, the first tip includes a first light transmitting section extending laterally from a base of the first tip section, and the second tip includes a second light transmitting section extending laterally from a base of the second tip section. In still another exemplary form, at least one of the first distal end of the first light guide and the second distal end of the second light guide includes an opening in fluid communication with a source of flowing air. In yet another exemplary form, the dental curing light includes a third light guide in optical communication with at least one light source in electrical communication with the electrical power supply. Preferably, the third light guide directs light in a direction substantially perpendicular to the first light guide.

In yet another aspect, the invention provides a dental curing light and related methods for using the dental curing light. The dental curing includes an electrical power supply, and a light source in electrical communication with the electrical power supply. The curing light also includes a light guide including a proximal section, a first distal section extending from the proximal section, and a second distal section extending from the proximal section. The proximal section is in optical communication with the light source, the first distal section and the second distal section. The first distal section has a first distal end, and the second distal section has a second distal end.

The curing light also includes a first light tip having a first base connected to the first distal end of the first distal section of the light guide. The first light tip includes a first hollow tubular opaque body having a first aperture for emitting light. The first body comprises a flexible material which retains shape in a bent condition such that the first hollow body can be bent to emit light in a first selected direction from the first aperture. The curing light also includes a second light tip having a second base connected to the second distal end of the second distal section of the light guide. The second light tip includes a second hollow tubular opaque body having a second aperture for emitting light. The second body comprises a flexible material which retains shape in a bent condition such that the second hollow body can be bent to emit light in a second selected direction from the second aperture.

Preferably, an outside diameter of the first light tip tapers inward from the first base toward the first aperture, and an outside diameter of the second light tip tapers inward from the second base toward the second aperture. The tapered curing light tip adaptors (micro-flex tips) are sized to fit into the narrow area between tooth surfaces and to flex to create better access and patient comfort. Tip to composite surface distance is extremely important to the depth and rate of cure where even a six millimeter distance is extremely important. Current curing light tip sizes are far too large and/or stiff to reach interproximally. In one form, the electrical power supply, the light source and the proximal section of the light guide are encased in a housing. In another form, the electrical power supply and the light source are encased in a housing. The first light tip can by removably connected to the first distal end of the first distal section of the light guide, and the second light tip can be removably connected to the second distal end of the second distal section of the light guide. The tapered curing light tip adaptors (micro-flex tips) are sized to fit into the narrow area between tooth surfaces and to flex to create better access and patient comfort. Tip to composite surface distance is extremely important to the depth and rate of cure where even a six millimeter distance is extremely important. Current curing light tip sizes are far too large and/or stiff to reach interproximally.

The dental curing light can be used in a method for the restoration of a tooth having a hollow cavity preparation in an interproximal surface of the tooth. In the method, a light-curable restorative material is placed in the cavity preparation, light is directed from the first light tip of the dental curing light at a buccal portion of the restorative material in the cavity preparation, and light is directed simultaneously from the second light tip of the dental curing light at a lingual portion of the restorative material in the cavity preparation. In the method, the first light tip can be bent such that light can be directed at the buccal portion of the restorative material in the cavity preparation In still another aspect, the invention provides a dental curing light and related methods for using the dental curing light. The dental curing light includes an electrical power supply, a first light guide in optical communication with at least one light source in electrical communication with the electrical power supply, a second light guide in optical communication with at least one light source in electrical communication with the electrical power supply, and a third light guide in optical communication with at least one light source in electrical communication with the electrical power supply. Preferably, the third light guide directs light in a direction substantially perpendicular to the first light guide, and the third light guide directs light in a direction substantially perpendicular to the second light guide. The dental curing light may include a first light transmitting tip connected to a first distal end of the first light guide, and a second light transmitting tip connected to a second distal end of the second light guide wherein the first tip and the second tip are angled toward each other.

In one exemplary form, the first light guide is in optical communication with a first light source in electrical communication with the electrical power supply, and the second light guide is in optical communication with a second light source in electrical communication with the electrical power supply, and the third light guide is in optical communication with a third light source in electrical communication with the electrical power supply. Preferably, the first light source is located in a first distal end of the first light guide, and the second light source is located in a second distal end of the second light guide, and the third light source is located in a third distal end of the third light guide. The first light guide and the second light guide can be connected to a housing, and at least one of the first light guide and the second light guide can be movable with respect to the housing. Preferably, the first light guide and the second light guide are both hinged to the housing for movement with respect to the housing. In another exemplary form, a first light transmitting tip is connected to a first distal end of the first light guide, a second light transmitting tip connected to a second distal end of the second light guide, the first light guide and the second light guide are normally biased into a relaxed position in which the first distal tip and the second distal tip are a first distance apart, and the first light guide and the second light guide have an outwardly flexed position in which the first distal tip and the second distal tip are a second distance apart, the second distance being greater than the first distance. Preferably, the first distance is about 4 to about 15 millimeters.

In another aspect, the invention provides a dental curing light including a housing, an electrical power supply, and an elongated arm extending from the housing. The arm has a distal section that terminates in a distal end wherein the distal section and the distal end define an included angle of greater than 0 degrees and less than 180 degrees. The curing light also includes a support having a base wall, a first wall extending from a first end of the base wall, and a spaced apart second wall extending from a second end of the base wall. The base wall is connected to the distal end of the arm. The curing light also includes a first light source in electrical communication with the power supply. The first light source transmits light away from an inner surface of the base wall. The curing light also includes a second light source in electrical communication with the power supply wherein the second light source transmits light away from an inner surface of the first wall. The curing light also includes a third light source in electrical communication with the power supply wherein the third light source transmits light away from an inner surface of the second wall. The included angle can be about 30 degrees to about 150 degrees. Preferably, the included angle is 60 degrees to about 120 degrees. In one form, the included angle is about 90 degrees. The support can have a generally U-shaped perimeter or a generally V-shaped perimeter.

In yet another aspect, the invention provides a separator ring for separating teeth and/or for creating adaptation pressure on an interproximal dental matrix stabilizer and/or a dental matrix. The separator ring includes an elastic metallic body that terminates in a pair of spaced apart clamping ends. The ends are dimensioned to separate teeth and/or create adaptation pressure on an interproximal dental matrix stabilizer and/or a dental matrix. The ends are translucent.

In one exemplary form, the ends include a first tip and a spaced apart second tip wherein the first tip is dimensioned to create adaptation pressure on the dental matrix and the second tip is dimensioned to create adaptation pressure on the interproximal dental matrix stabilizer. In another exemplary form, the ends have a configuration selected from the group consisting of J-shaped, L-shaped and V-shaped. In still another exemplary form, the body includes a pair of spaced apart legs that extend away from the body, each end is attached to one of the legs, and the ends are removable from the elastic body. In yet another exemplary form, the body includes a pair of spaced apart legs that extend away from the body, each end is attached to one of the legs, each end includes a surface with a ridge, and the ridges are arranged in a facing relationship when the ends are attached to the legs. Preferably, the ridges are centrally located on the surface. Preferably, the ridges extend from one edge to an opposite edge of the surface. The ridges can be coplanar with the legs when the ends are attached to the legs. In another exemplary form, the body includes a pair of spaced apart legs that extend away from the body, each end is attached to one of the legs, and each end includes a concavity in a surface opposite the body. In still another exemplary form, the body includes a pair of spaced apart legs that extend away laterally from the body, each end is attached to one of the legs, and the body is circular. The body can include an arcuate cover.

In still another aspect, the invention provides a separator ring for separating teeth and/or for creating adaptation pressure on an interproximal dental matrix stabilizer and/or a dental matrix. The separator ring includes an elastic metallic body that terminates in a first leg that extends away from the body and a second leg that extends away from the body wherein the first leg and the second leg are in spaced relationship. A first translucent clamping end is attached to the first leg; and a second translucent clamping end is attached to the second leg. The first end and the second end are dimensioned to separate teeth and/or create adaptation pressure on an interproximal dental matrix stabilizer and/or a dental matrix when the separator ring is installed between the teeth.

In one exemplary form, the first end is removable from the first leg, and the second end is removable from the second leg. In another exemplary form, the first leg extends away perpendicularly from the body, and the second leg extends away perpendicularly from the body. In still another exemplary form, the first end includes a first surface with a first ridge, the second end includes a second surface with a second ridge, and the first ridge and the second ridge are arranged in a facing relationship when the first end is attached to the first leg and the second end is attached to the second leg. The first ridge can be centrally located on the first surface, and the second ridge cam be centrally located on the second surface. Preferably, the first ridge extends from one edge to an opposite edge of the first surface, and the second ridge extends from one edge to an opposite edge of the second surface. The first ridge can be coplanar with the first leg when the first end is attached to the first leg, and the second ridge can be coplanar with the second leg when the second end is attached to the second leg. The first end can include a concavity in a surface opposite the body, and the second end can include a concavity in a surface opposite the body.

In yet another aspect, the invention provides a kit for preparing a form for filling a hollow cavity preparation in a tooth. The kit includes at least one sectional dental matrix comprising a curved strip of material. The strip has a length from a first end to a second end sufficient to extend beyond a first vertical junction of the cavity preparation and a surface of the tooth and to extend beyond a second vertical junction of the cavity preparation and the surface of the tooth to create the form for filling the cavity preparation. The strip has a horizontally concave side surface and a horizontally convex side surface. The kit also includes at least one separate dental matrix stabilizer including an elongated elastic body having a first end portion, a second opposite end portion, a middle portion connecting the first end portion and the second end portion, and a first side surface. The first side surface of the body includes a first outwardly extending protrusion on the first end portion, and the first side surface of the body further includes a second outwardly extending protrusion on the second end portion.

In the kit, the dental matrix can have has a first thickness between the concave side surface and the convex side surface at a first plane horizontal to the strip that is less than a second thickness between the concave side surface and the convex side surface at a second plane horizontal to the strip wherein the second plane is below the first plane. The strip of the dental matrix can have a base portion and an upper portion integral with and extending upward from the base portion, wherein the horizontally concave side surface forming the base portion is not vertically concave, and the horizontally concave side surface forming the upper portion of the dental matrix is vertically concave. The strip of the dental matrix can have a base portion and an upper portion integral with and extending upward from the base portion, and strip thickness between the concave side surface and the convex side surface at planes horizontal to the strip can decrease from lower to upper sections of the upper portion of the strip.

In the kit, the first end portion of the interproximal dental matrix stabilizer can include an area of material weakness extending toward the top surface and extending toward the bottom surface and extending toward a first end surface of the body whereby the first end portion can be separated into separate end members by application of a separation force at the area of material weakness.

In one exemplary form, the kit includes a matrix removal tool selected from the group consisting of pliers, tweezers or forceps. In another exemplary form, the kit includes more than one of the dental matrix, and at least two of the matrix are anatomically shaped for different teeth. In still another exemplary form, the kit includes more than one of the dental matrix, and at least two of the matrix are tooth specific for different teeth. In yet another exemplary form, the kit includes more than one of the dental matrix, and at least two of the matrix are tooth type specific for different teeth. In still another exemplary form, the kit includes more than one of the dental matrix, and at least two of the matrix are tooth surface specific for different tooth surfaces.

The kit may further include a separator ring for separating teeth and/or for creating adaptation pressure on the dental matrix stabilizer and/or the dental matrix. The separator ring comprises an elastic metallic body that terminates in a pair of spaced apart clamping ends. The clamping ends are dimensioned to separate teeth and/or create adaptation pressure on the dental matrix stabilizer and/or the dental matrix. Preferably, the clamping ends are translucent.

The kit may further include a set of instructions for using the kit in filling the cavity preparation. The kit may further include a set of instructions for preparing the cavity preparation before using the kit. The set of instructions can be a disc (such as a DVD or CD) and/or printed materials (such as a book). The set of instructions can be a tooth preparation guide for preparing a cavity preparation according to the invention or a guide for restoring a tooth using the method of the invention. The kit can include more than one of the dental matrix stabilizer, and at least two of the dental matrix stabilizer are of different size. The kit can have a curing light.

In the kit, the first outwardly extending protrusion of the dental matrix stabilizer can be spaced inward from a first end surface of the body of the dental matrix stabilizer, and the second outwardly extending protrusion of the dental matrix stabilizer can be spaced inward from a second end surface of the body of the dental matrix stabilizer. Preferably, the body of the dental matrix stabilizer is translucent. Preferably, the material of the curved strip of the dental matrix is translucent.

In one form of the kit, the dental matrix comprises a second curved strip of translucent material. The second strip can have a length from a first end to a second end sufficient to extend beyond a first vertical junction of a second cavity preparation in an adjacent tooth and a surface of the adjacent tooth and to extend beyond a second vertical junction of the second cavity preparation and the surface of the adjacent tooth to create the form for filling the second cavity preparation. The second strip can have a horizontally concave side surface and a horizontally convex side surface wherein the second curved strip is joined to the curved strip.

In another form of the kit, the dental matrix can have a second curved strip of translucent material wherein the second strip has a length from a first end to a second end sufficient to extend beyond a first vertical junction of a second cavity preparation in an adjacent tooth and a surface of the adjacent tooth and to extend beyond a second vertical junction of the second cavity preparation and the surface of the adjacent tooth to create the form for filling the second cavity preparation. The second strip can have a horizontally concave side surface and a horizontally convex side surface wherein the second curved strip and/or the curved strip have at least one throughhole.

Therefore, it is one advantage of the invention to provide a single load, injection molded class II preparation, matrixing and composite filling technique and instruments.

It is another advantage of the invention to provide a unique translucent anatomic series of matrices and stabilizing instruments for class III, IV and VI composites.

It is still another advantage of the invention to provide a fully translucent matrix, separator and stabilizers (wedging action to replace wedge) that allows better vision (than metal matrices and separators) and full light curing access from occlusal and interproximal areas. This lateral and or simultaneous curing of a class II composite is an integral and unique feature of the invention. Heretofore the light curing has been based on curing from the occlusal (or chewing surface of the tooth) which requires several incremental layers.

It is yet another advantage of the invention to provide a fully anatomic sectional matrix and stabilizers.

It is still another advantage of the invention to provide a sectional translucent anatomic dental matrix which allows for the restoration of two approximating teeth simultaneously, including a back to back version. One of the two sectional matrices are designated as "back to back" and have a contact area specific cut out to allow a tighter contact. Non-limiting advantages are that there is only one thickness of material (e.g., Mylar™) between the approximating teeth which allows a tighter contact area; and also to avoid collapsing or buckling of one of the two rounded matrices where one of the two matrices will invert and create an undesirable concavity on the outer surface. This situation is uniquely critical to a Mylar™ type matrix but will also be beneficial to a metal version of the matrix.

It is yet another advantage of the invention to provide a system to allow a completely convex surface to a filling in all axes. Previous systems create flat spots and a lack of bulbousness to the outer surface of the filling that encourage bacterial colonization and food impaction which is a pervasive problem in dentistry today. A completely convex filling surface that is naturally smooth from the resultant ideal anatomic shape of the matrix has inherent health benefits because of improved self cleansing and better action and access for a toothbrush and floss. Once the composite is trimmed back to fit the tooth, the surface loses its luster and smoothness and rarely is it polished back to the mirror like finish of composite that is injected against these matrix and then left untouched.

It is still another advantage of the invention to provide a restorative and matrix system to be tooth specific. Previous systems are classified simply as anterior or posterior tooth specific. The system of the invention, because it is truly anatomic, is specific to each tooth or tooth type. For example, in some instances it will be specific to the mesial or distal (right side or left side of front teeth, front or back for back teeth) of the tooth. This is important because teeth have unique shapes that are specific to each tooth and each "side" of the tooth. For example the mesial of an upper incisor is significantly flatter than the distal surface. Because of the specificity of the system this feature is required. Significant adaptation and forming of generically shaped, non anatomic matrices is currently the standard. Because these conventional matrices do not fit the tooth precisely, time and energy is spent to crimp and press the matrix to conform to the tooth. In addition to time and energy wasted, the crimping and wedging create flat spots, indentations and other filling surface flaws.

It is yet another advantage of the invention to provide a system that has matrices that are self adapting. Because the fit is natural with advantages of saved time, energy for the clinician, and a filling with a better, smoother, healthier, and more comfortable surface.

It is still another advantage of the invention to provide a method and instruments for the restoration of a tooth where less finishing or removal of excess restorative material is a feature because of an intimate adaptation to a tooth being restored by a matrix that allows the injection molding of restorative material to occur without excess extruding in areas that are difficult to access. Better final result and times savings are some results.

It is yet another advantage of the invention to provide a method, when there is deep decay or a previous filling that incorporates both the occlusal and interproximal surfaces, wherein the method is divided into the occlusal first and then the interproximal surfaces last. In other words, the occlusal and deep interproximal are prepared and then filled. Then the interproximal is prepared or re-prepared with the ideal saucer or slice shape so that the cavity configuration will allow for the ideal "C factor" (cavity configuration factor) and so that is never deeper than two millimeters in the axial dimension. Then the injection molding, single load technique can be utilized with the components of the system of the invention.

It is still another advantage of the invention to provide a method and instruments for the restoration of a tooth where feather and knife edge cavity margins are produced. Combined with the overall saucer shape of the cavity preparation, it creates a C Factor (cavity configuration factor) that can be as small as 1/1 or 1. Typical C factors for traditional class II cavity preparations are in the range of 2/1 or 3/1 or higher. The higher the C factor, the greater the risk that areas of composite will pull away from a tooth surface during polymerization leaving a resulting gap; or creating stress to the tooth causing enamel fractures and/or post-operative symptoms.

It is yet another advantage of the invention to provide a method for the restoration of a posterior tooth having an original shape including a top surface and an interproximal surface. The unique preparation design, restorative protocol and kit for filling and finishing are interdependent on each aspect to create a significant advancement in this procedure. The final outcome is a tooth that will be less weakened and therefore more fracture resistant. The C factor is mitigated, and marginal integrity and filling strength are greatly improved with the method.

It is still another advantage of the invention to provide a method including simultaneously light curing of a bonding agent and a flowable composite and paste composite resin contained in the cavity preparation. Preferably, the curing light is simultaneously directed at the top surface of the tooth, at a buccal portion of the interproximal surface of the tooth, and a lingual portion of the interproximal surface of the tooth. Buccal-Lingual curing of a Class II restoration is unique to this advancement, heretofore has been from largely from the occlusal.

It is yet another advantage of the invention to provide a method for the restoration of a tooth wherein the filled cavity preparation of the interproximal area is injection molded rather than layered and therefore seamless. Injection of the second and third components, flowable composite and paste composite into an existing pool of uncured and therefore fluid environment allows consistent bubble and gap formation.

The combination of one or more features of the invention allows the radical departure from traditional class II composite preparations and fillings which have a significant failure rate, as high as 50% higher failure rate than Class II silver amalgam fillings. (See, for example, Van Nieuwenhuysen et al., "Long-term evaluation of extensive restorations in permanent teeth", *J. Dent.* 2003, 31:395-405; and Sjogren et al., "Survival time of class II molar restorations in relation to patient and dental health insurance costs for treatment", *Swed Dent J.* 2002, 26:59-66; and Mjor et al., "Placement and replacement of restorations in primary teeth. *Acta Odontol Scand.* 2002, 60:25-28.)

Although Class II composites have been performed for at least 25 years, the cavity form has maintained a "mechanical lock" created by undercuts that physically retain the filling. This was a necessary design for non-bonded silver amalgam. Unfortunately these "box" forms leave weakened, undermined, vulnerable tooth structure and the tooth often begins to fracture over time. Cracked and fractured teeth are now the third leading cause of tooth loss in industrialized nations. It is therefore another advantage of the invention to provide an excellent seal and high surface area for enamel rod engagement. This overall system (tooth preparation, matrix system, injection molded filling process) allows for a non mechanical undercut cavity and instead relies on adhesion to enamel rods (pores of the enamel opened up during conditioning/etching of enamel) and the filling is retained with the same robust and permanent adhesion enjoyed by cosmetic veneering of front teeth which have no mechanical retention, only enamel adhesion.

These and other features, aspects, and advantages of the present invention will become better understood upon consideration of the following detailed description, drawings, and appended claims.

BRIEF DESCRIPTION OF THE DRAWINGS

FIG. 9 is a top view of one embodiment of an interproximal dental matrix stabilizer according to the invention.

FIG. 10 is a side cross-sectional view of a dental matrix according to the invention.

FIG. 11 is a side cross-sectional view of another dental matrix according to the invention.

FIG. 12 is a top view of a light curing device according to the invention.

FIG. 12AA is a view of the light curing device of FIG. 12A taken along line 12AA-12AA of FIG. 12A.

FIG. 12H is a side view of still another version of a light curing device according to the invention.

FIG. 12I is a view of the light curing device of FIG. 12H taken along line 12I-12I of FIG. 12H.

FIG. 25 is a perspective view showing the use of another alternative separator ring according to the invention.

FIG. 26 is a bottom view of the separator ring shown in FIG. 25.

FIG. 27 is a front view of the separator ring shown in FIG. 25.

FIG. 28 is a side view of the separator ring shown in FIG. 25.

Like reference numerals will be used to refer to like parts from Figure to Figure in the following description of the drawings.

DETAILED DESCRIPTION OF THE INVENTION

Figure 1:
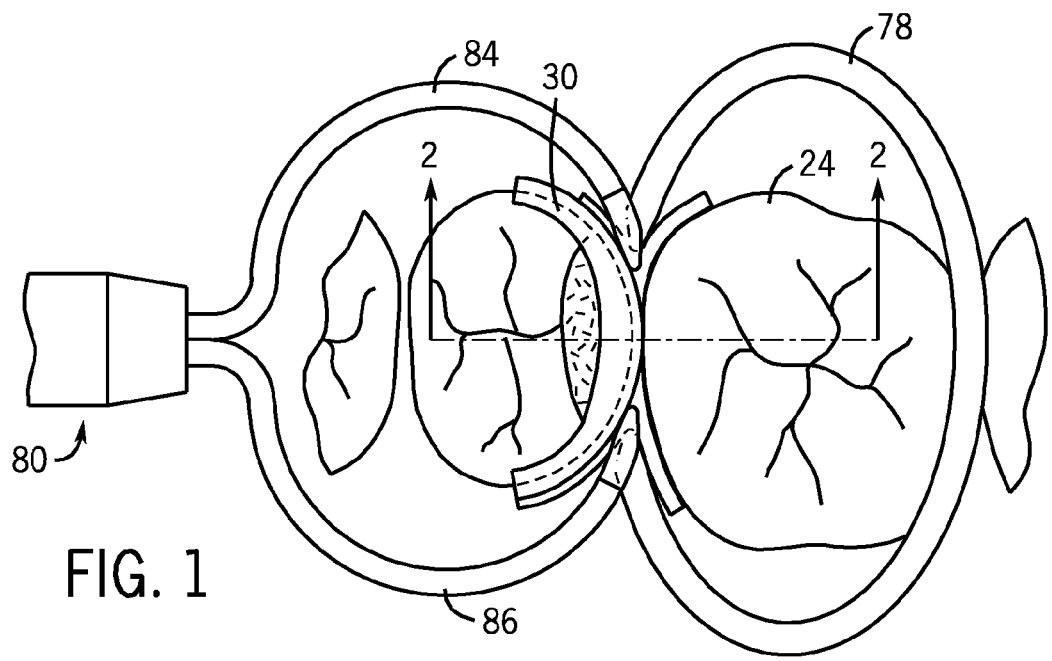
FIG. 1 is a top view of the light curing step of a tooth restoration method according to the invention.
Figure 2:
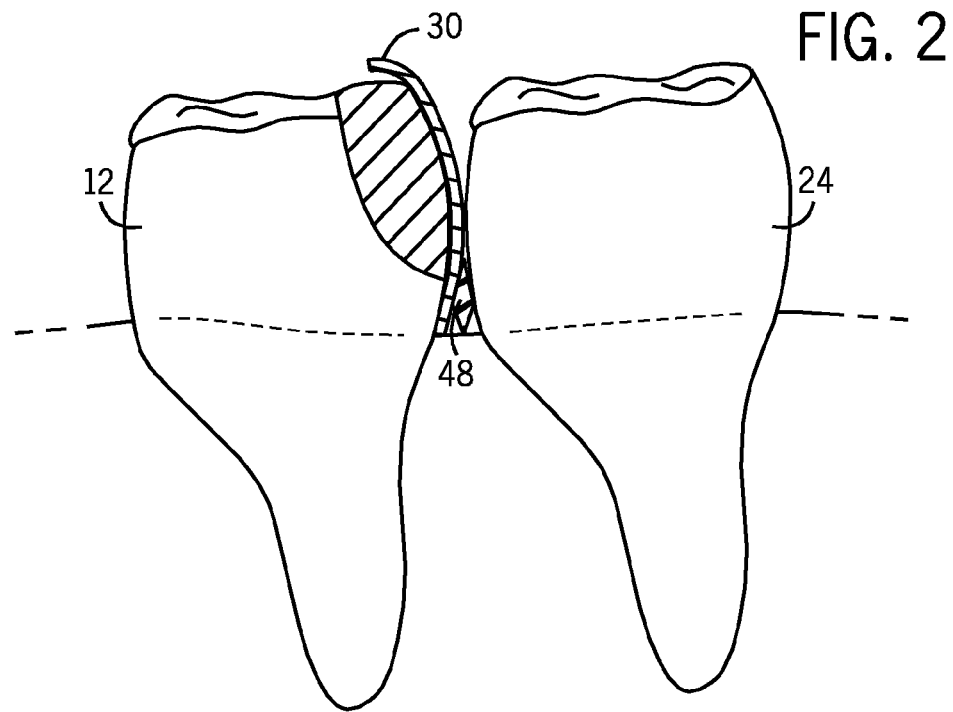
FIG. 2 is a cross-sectional view taken along line 2-2 of FIG. 1.
Figure 3:
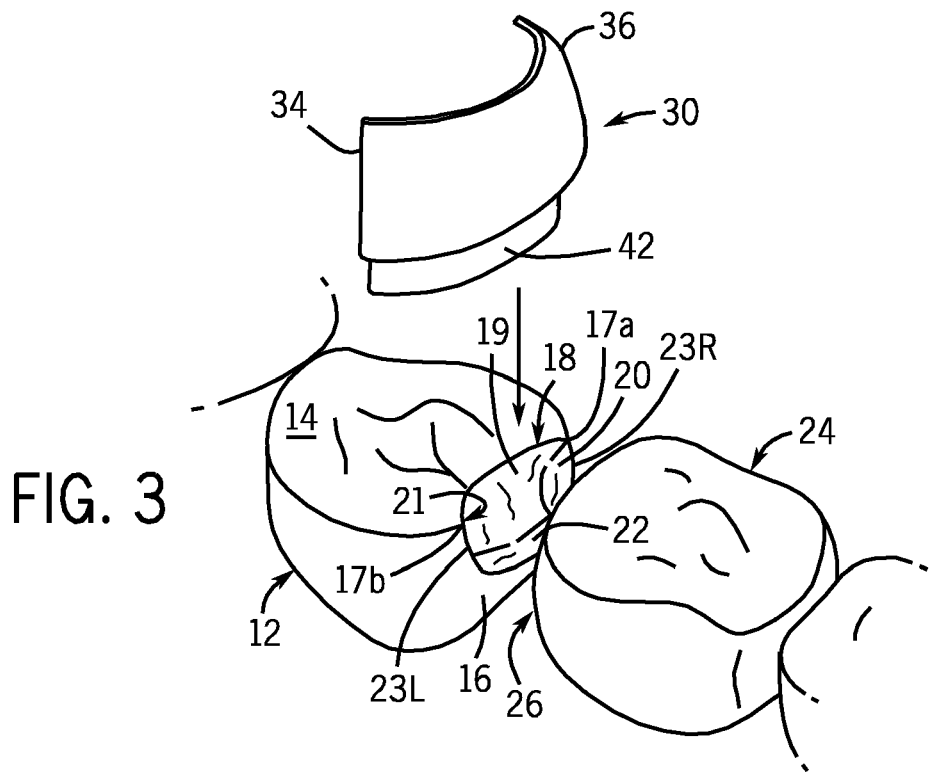
FIG. 3 is a top perspective view of the matrix insertion step of the method according to the invention.

Turning to FIGS. 1-8, there is shown various steps and devices in an example method according to the invention for the restoration of a tooth. In a first step, the dentist locates a tooth having a cavity. Referring to FIG. 3, there is shown a tooth 12 having a top occlusal surface 14 and an interproximal side surface 16. A hollow cavity preparation 18 has been prepared in tooth 12. The hollow cavity preparation 18 includes an inner surface 19, a side surface 20, an opposite side surface 21 and a bottom surface 22. Using the well known classification system developed by Dr. G. V. Black in 1908, this would be a Class II cavity involving the interproximal side surface 16 and top occlusal surface 14 of tooth 12, which may be a premolar or molar.

The tools and techniques for removing a portion of the top surface 14 of the tooth 12 and a portion of the interproximal surface 16 of the tooth 12 to form the hollow cavity preparation 18 are well known in the art and therefore will not be explained further. However, the Class II cavity preparation 18 of FIG. 3 is saucer shaped when viewed from above and does not have the usual box-like shape of a conventional Class II cavity preparation. Specifically, the ends 17a, 17b of the cavity preparation 18 are not tangential to the tooth outside surface. Also, the cavity preparation 18 does not extend inward more than two millimeters inward from the interproximal side surface 16.

Figure 4:
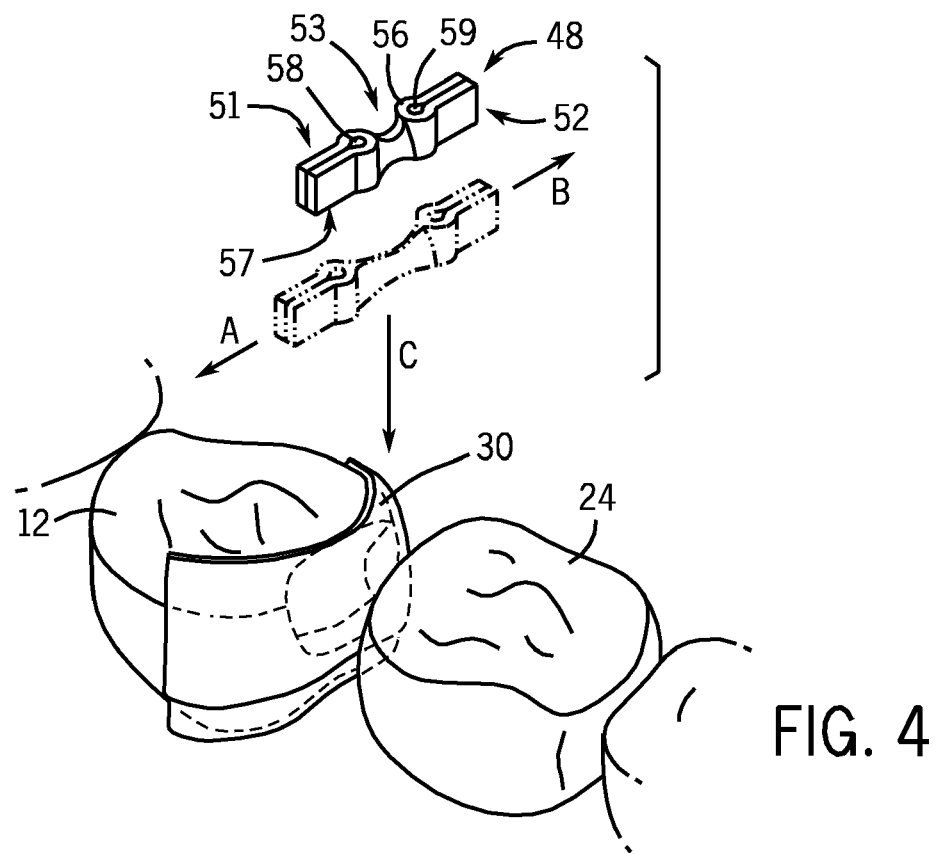
FIG. 4 is a top perspective view of the interproximal dental matrix stabilizer insertion step of the method according to the invention.

After preparation of the saucer shaped Class II cavity preparation 18 in the tooth 12 of FIG. 3, a wedge (not shown) is inserted between the interproximal surface 16 of the tooth 12 and the interproximal surface 26 of adjacent tooth 24 to create a gap between the tooth 12 and the tooth 24. Known wedges are suitable for this "pre-wedging" step. The wedge is removed, and a sectional anatomic translucent anatomic dental matrix 30 is inserted between the tooth 12 and the tooth 24 as shown in FIGS. 3 and 4. The dental matrix 30 will be described in further detail below.

Figure 5:
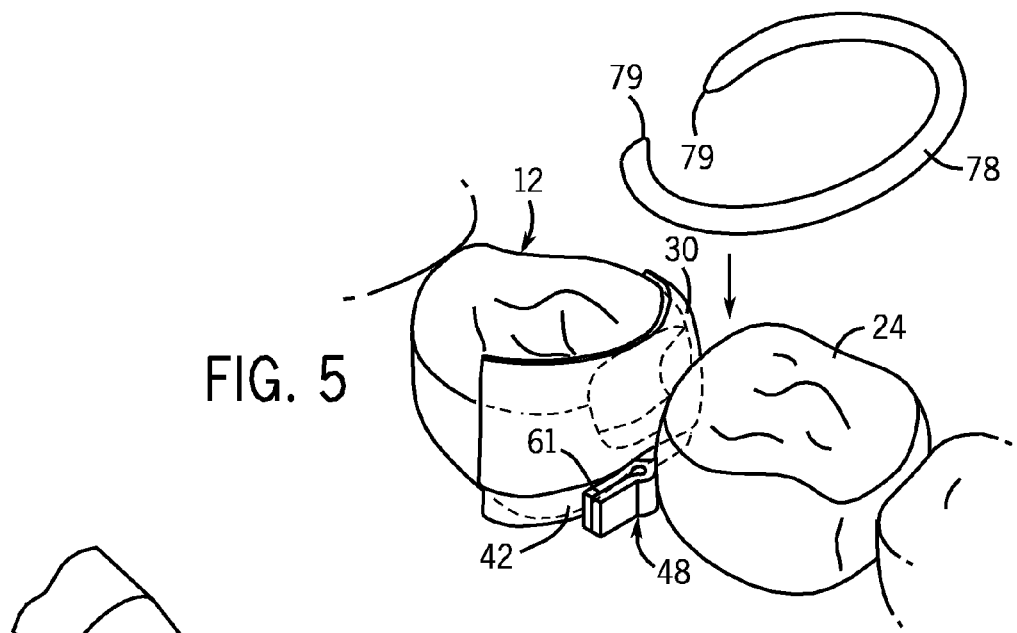
FIG. 5 is a top perspective view of the ring separator insertion step of the method according to the invention.

Looking at FIGS. 4 and 5, the clear plastic anatomical sectional matrix 30 is placed around the tooth 12 maintaining anatomic root adaptation contact using an interproximal dental matrix stabilizer 48 according to the invention. The interproximal dental matrix stabilizer 48 will be described in further detail below. A metallic elastic separator ring 78 is then placed in the interproximal embrasure to create slight tooth separation and additional adaptation pressure on the interproximal dental matrix stabilizer 48 and/or the matrix 30.

The cavity preparation 18 in tooth 12 is then etched with liquid and/or gel phosphoric acid, about 2 millimeters past the margins. The cavity preparation 18 in tooth 12 is then rinsed and dried. A lightly filled or unfilled light curable resin tooth bonding agent is then applied to tooth 12 covering the entire cavity preparation 18 and about 0.5-1.5 millimeters past the margins. The resin tooth bonding agent is then air thinned except on surface 22 where a small pool of resin tooth bonding agent is maintained. The resin tooth bonding agent is not light cured at this point. Resin tooth bonding agents improve composite to enamel and/or dentin bonding. One example resin tooth bonding agent is available under the tradename OptiBond Solo Plus®.

A light curable flowable composite resin is then injected directly into the pool of resin tooth bonding agent (under magnification if possible) without incorporating bubbles. A tiny amount of the light curable flowable composite resin is expressed before placement to ensure that there is no air in the cannula. The light curable flowable composite and resin tooth bonding agent are not light cured at this point. Generally, light curable flowable composite resins contain 20-25 percent less filler in the light curable polymeric material than nonflowable paste materials. Light curable flowable composite resins are available under tradenames such as Filtek™, Flow-It™, EsthetX®, Revolution®, AeliteFlo®, PermaFlo®, Dyract Flow®, Tetric®, and Heliomolar®. Light curable resins are preferred as light cured resins are more color stable than chemically cured resins.

A light curable paste composite resin is then extruded into the pool of flowable composite resin and resin tooth bonding agent without creating air bubbles, allowing the composite resin to displace most of the lesser filled flowable composite resin and resin tooth bonding agent (under magnification if possible). Composite resins are available under tradenames such as 3M Z100™, 3M Filtek Supreme™, and Prodigy®. The next steps are burnishing, carving the anatomy and carving excess composite. There is no need to use a condenser or plugger.

The top occlusal surface 14 of the filled cavity preparation is then cured using a curing light such as high intensity light emitting diode (LED) lights, plasma-arc curing lights, halogen lights, and laser lights. The interproximal region of the filled cavity preparation is cured using a dental curing light 80 with a light guide having two separate distal sections that allow for simultaneous curing of the buccal portion and the lingual portion of the filled cavity preparation while applying air cooling from an air syringe or one curing light according to the invention. Thus, lateral light curing is used. Alternatively, two individual curing lights can be used. The separator ring 78 and interproximal dental matrix stabilizer 48 are then removed and the simultaneous curing of the buccal portion and the lingual portion of the filled cavity preparation is then repeated using the dental curing light 80 that will be described in further detail below. The matrix 30 is then removed, and the restored tooth 12 is polished with discs, strips, and rubber tipped and carbide burs.

In cases where the cavity preparation 18 must extend inward more than about two millimeters from the interproximal side surface 16, an alternative method may be used. In this alternative method, a base material, such as a flowable composite, a glass ionomer material or a paste composite resin, is first used to build up the restoration such that the cured base material is about two millimeters or less from the desired restored tooth interproximal outside surface. However, the cured base material does not extend to the edge of the cavity preparation 18 in the tooth. A lightly filled or unfilled light curable resin tooth bonding agent is then applied to the cured base material in the cavity preparation 18 and about 0.5-1.5 millimeters past the margins. The resin tooth bonding agent is then air thinned except on surface 22 where a small pool of resin tooth bonding agent is maintained. The resin tooth bonding agent is not light cured at this point.

A light curable flowable composite resin is then injected directly into the pool of resin tooth bonding agent (under magnification if possible) without incorporating bubbles. A tiny amount of the light curable flowable composite resin is expressed before placement to ensure that there is no air in the cannula. The light curable flowable composite and resin tooth bonding agent are not light cured at this point. A light curable paste composite resin is then extruded into the pool of flowable composite resin and resin tooth bonding agent without creating air bubbles, allowing the composite resin to displace most of the lesser filled flowable composite resin and resin tooth bonding agent (under magnification if possible). The next steps are burnishing, carving the anatomy and carving excess composite. The light curing process then proceeds as above.

An example embodiment of a sectional translucent anatomic dental matrix 30 that can be used in the method of the invention will be now be described in further detail. While the matrix 30 has been illustrated and described herein in the context of a Class II restoration, the matrix 30 and all other matrices described herein are also suitable for Class III and Class IV restorations. Looking at FIGS. 3 and 10, the dental matrix 30 includes a curved strip 32 of translucent material. The dental matrix 30 can be formed from a translucent material such as a polymeric film. One non-limiting example material is the polyester film commercially available as Mylar™. The strip 32 has a length running from a first end 34 to a second end 36 of the dental matrix 30. The length of the dental matrix 30 is sufficient to extend beyond a first vertical junction 23L of the interproximal cavity preparation 18 and an interproximal surface 16 of the tooth 12 and to extend beyond a second vertical junction 23R of the interproximal cavity preparation 18 and the interproximal surface 16 of the tooth 12 to create the form for filling the interproximal cavity preparation 18.

The strip 32 of the dental matrix 30 has a horizontally concave side surface 38 and a horizontally convex side surface 40 (see FIG. 10). The concave side surface 38 and the convex side surface 40 extend from the first end 34 to the second end 36 of the dental matrix 30. The strip 32 of the dental matrix 30 also has a base portion 42 and an upper portion 44 integral with and extending upward from the base portion 42 of the dental matrix 30. The horizontally concave side surface 38 forming the base portion 42 is not vertically concave (that is, a cross-section of the base portion 42 has parallel straight vertical walls that are normal to a bottom surface 46 of the dental matrix 30. The horizontally concave side surface 38 forming the upper portion 44 of the dental matrix 30 is vertically concave. See FIG. 10. The horizontally concave side surface 38 is anatomic in that the horizontally concave side surface 38 has an inner surface that that conforms to the shape of the outer surface of the region of the natural tooth being restored.

Preferably, the matrix 30 is anatomically shaped. The matrix 30 can be tooth specific. By "tooth specific" it is meant that the matrix is configured to conform to the shape of the outer surface of the specific natural tooth being restored such as (without limitation) an upper right second molar. The matrix 30 can be tooth type specific. By "tooth type specific" it is meant that the matrix is configured to conform to the shape of the outer surface of the specific type of natural tooth being restored such as (without limitation) an upper molar. The matrix 30 can be tooth surface specific. By "tooth surface specific" it is meant that the matrix is configured to conform to the shape of the outer surface of the specific natural tooth surface being restored such as (without limitation) an upper right first molar mesial surface.

Turning to FIG. 11, there is shown another embodiment of a sectional translucent anatomic dental matrix 30A. In the dental matrix 30A, the strip thickness between the concave side surface 38A and the convex side surface 40A at planes horizontal to the strip 32A decreases from lower to upper sections of the strip 32A. Thus, the clear plastic anatomical matrix 30A has variable thickness to allow the thinner portion for the tooth contact area and the thicker portion at the gingival area. The tapering (decrease in thickness) of the strip 32A can begin at any location above the bottom surface 46A of the strip 32A. However, in one version of the strip 32A, the tapering of thickness begins in the upper portion 44A. In other words, the base portion 42A has uniform thickness. The dental matrix 30A can be formed from a translucent material such as a polymeric film. One non-limiting example material is the polyester film commercially available as Mylar™.

Figure 14:
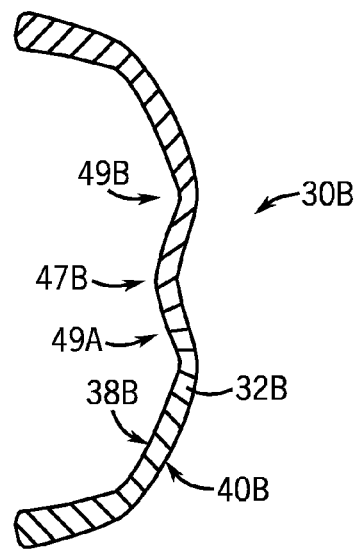
FIG. 14 is a cross-sectional view of the dental matrix of FIG. 10 taken along line 14-14 of FIG. 10.

Turning to FIG. 14, there is shown yet another embodiment of a sectional translucent anatomic dental matrix 30B. In the dental matrix 30B, the strip 32B has a first side surface 38B and a second side surface 40B. The first side surface 38B has an intermediate horizontally convex section 47B between a first horizontally concave section 49A and a second horizontally concave section 49B. The intermediate horizontally convex section 47B provides contact with tooth surface that may have inward furcation and/or fluting from decay due to the age of the patient. The intermediate horizontally convex section 47B can begin at any location above the bottom surface of the strip 32B. The dental matrix 30B can be formed from a translucent material such as a polymeric film. One non-limiting example material is the polyester film commercially available as Mylar™.

An example embodiment of an interproximal dental matrix stabilizer 48 that can be used in the method of the invention will be now described in further detail. Looking at FIGS. 4 and 9, the interproximal dental matrix stabilizer 48 includes an elongated translucent (preferably transparent) elastic body 50 having a first end portion 51, a second opposite end portion 52, a middle portion 53 connecting the first end portion 51 and the second end portion 52, a first side surface 54, a second side surface 55, a top surface 56 and a bottom surface 57. The first end portion 51 has a first throughhole 58 extending from the top surface 56 to the bottom surface 57 of the interproximal dental matrix stabilizer 48. The second end portion 52 has a second throughhole 59 extending from the top surface 56 to the bottom surface 57 of the interproximal dental matrix stabilizer 48.

The first end portion 51 includes an area 61 of material weakness that extends toward the top surface 56 and extends toward the bottom surface 57 and extends toward a first end surface 62 of the body 50. The area 61 of material weakness extends from the first throughhole 58 to the first end surface 62 of the body 50. This allows the first end portion 51 to be separated into separate end members 63, 64 by application of a separation force at the area 61 of material weakness of the interproximal dental matrix stabilizer 48. Preferably, end members 63, 64 have a rectangular vertical cross-section. The area 61 of material weakness can be formed with a material of lower shear strength than the other material of the dental matrix stabilizer 48, or can be formed by including perforations or other like open areas in the area 61 of material weakness.

The second end portion 52 includes an area 65 of material weakness that extends toward the top surface 56 and extends toward the bottom surface 57 and extends toward a second end surface 66 of the body 50. The area 65 of material weakness extends from the second throughhole 59 to the second end surface 66 of the body 50. This allows the second end portion 52 to be separated into separate end members 67,68 by application of a separation force at the area 65 of material weakness of the interproximal dental matrix stabilizer 48. Preferably, end members 67, 68 have a rectangular vertical cross-section. The area 65 of material weakness can be formed with a material of lower shear strength than the other material of the dental matrix stabilizer 48, or can be formed by including perforations or other like open areas in the area 65 of material weakness.

The top surface 56 of the body 50 of the interproximal dental matrix stabilizer 48 includes a first pair of upper side-by-side depressions 71f, 71b in the middle portion 53 of the body 50, and the bottom surface 57 of the body 50 includes a second pair of analogous lower side-by-side depressions (not shown) in the middle portion of the body. The first pair of upper side-by-side depressions 71f, 71b include inwardly curved inner surfaces 73f, 73b, and the second pair of lower side-by-side depressions (not shown) include analogous inwardly curved inner surfaces (not shown).

In the interproximal dental matrix stabilizer 48, the first side surface 54 of the body 50 includes a curved protrusion 75f located near the first throughhole 58 and a curved protrusion 76f located near the second throughhole 59. Likewise, the second side surface 55 of the body 50 includes a curved protrusion 75b located near the first throughhole 58 and a curved protrusion 76b located near the second throughhole 59. The interproximal dental matrix stabilizer 48 can be formed from a translucent (preferably transparent) elastomeric material such as a silicone elastomer or a polyurethane elastomer.

Figure 13:
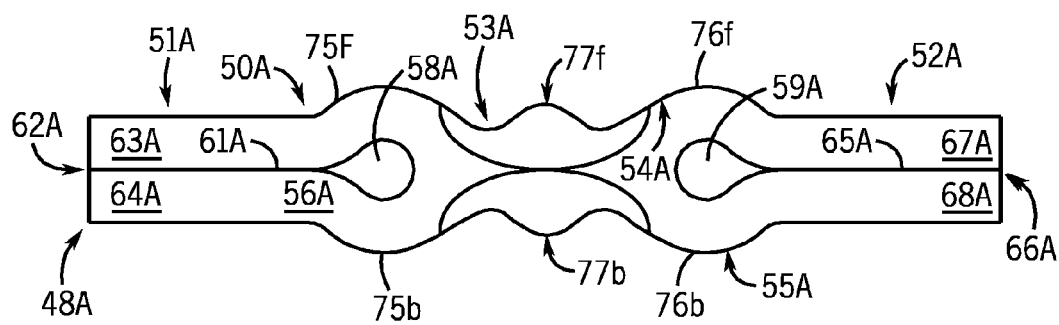
FIG. 13 is a top view of another embodiment of an interproximal dental matrix stabilizer according to the invention.

Turning to FIG. 13, there is shown another embodiment of an interproximal dental matrix stabilizer 48A which includes an elongated translucent (preferably transparent) elastic body 50A having a first end portion 51A, a second opposite end portion 52A, a middle portion 53A connecting the first end portion 51A and the second end portion 52A, a first side surface 54A, a second side surface 55A, a top surface 56A and a bottom surface (not shown). The first end portion 51A has a first throughhole 58A extending from the top surface 56A to the bottom surface of the interproximal dental matrix stabilizer 48A. The second end portion 52A has a second throughhole 59A extending from the top surface 56A to the bottom surface of the interproximal dental matrix stabilizer 48A.

The first end portion 51A includes an area 61A of material weakness that extends toward the top surface 56A and extends toward the bottom surface and extends toward a first end surface 62A of the body 50A. The area 61A of material weakness extends from the first throughhole 58A to the first end surface 62A of the body 50A. This allows the first end portion 51A to be separated into separate end members 63A, 64A by application of a separation force at the area 61A of material weakness of the interproximal dental matrix stabilizer 48A. Preferably, end members 63A, 64A have a rectangular vertical cross-section.

The second end portion 52A includes an area 65A of material weakness that extends toward the top surface 56A and extends toward the bottom surface and extends toward a second end surface 66A of the body 50A. The area 65A of material weakness extends from the second throughhole 59A to the second end surface 66A of the body 50A. This allows the second end portion 52A to be separated into separate end members 67A, 68A by application of a separation force at the area 65A of material weakness of the interproximal dental matrix stabilizer 48A. Preferably, end members 67A, 68A have a rectangular vertical cross-section.

In the interproximal dental matrix stabilizer 48A, the first side surface 54A of the body 50A includes a curved protrusion 75$f$ located near the first throughhole 58A and a curved protrusion 76$f$ located near the second throughhole 59A. Likewise, the second side surface 55A of the body 50A includes a curved protrusion 75$b$ located near the first throughhole 58A and a curved protrusion 76$b$ located near the second throughhole 59A.

In interproximal dental matrix stabilizer 48A, the first side surface 54A of the body 50A includes a first curved protrusion 77$f$ located near an intermediate vertical plane of the body 50A. Likewise, the second side surface 55A of the body 50A includes a second curved protrusion 77$b$ located near the intermediate vertical plane of the body 50A. The curved protrusions 77$f$, 77$b$ are beneficial when used with dental matrix 30B having the intermediate horizontally convex section 47B that provides contact with tooth surface that may have inward decay due to the age of the patient. The interproximal dental matrix stabilizer 48A can be formed from a translucent (preferably transparent) elastomeric material such as a silicone or polyurethane elastomer.

Figure 15:
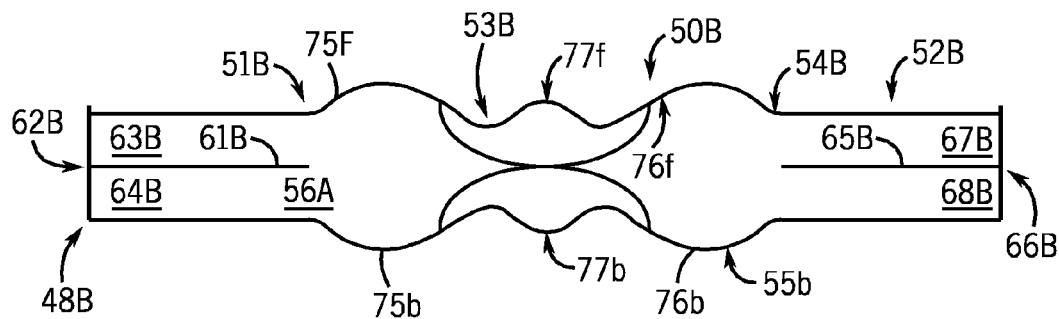
FIG. 15 is a top view of yet another embodiment of an interproximal dental matrix stabilizer according to the invention.

Turning to FIG. 15, there is shown another embodiment of an interproximal dental matrix stabilizer 48B which includes an elongated translucent (preferably transparent) elastic body 50B having a first end portion 51B, a second opposite end portion 52B, a middle portion 53B connecting the first end portion 51B and the second end portion 52B, a first side surface 54B, a second side surface 55B, a top surface 56B and a bottom surface (not shown).

The first end portion 51B includes an area 61B of material weakness that extends toward the top surface 56B and extends toward the bottom surface and extends toward a first end surface 62B of the body 50B. The area 61B of material weakness extends from an inner portion of the first end portion 51B to the first end surface 62B of the body 50B. This allows the first end portion 51B to be separated into separate end members 63B, 64B by application of a separation force at the area 61B of material weakness of the interproximal dental matrix stabilizer 48B. Preferably, end members 63B, 64B have a rectangular vertical cross-section.

The second end portion 52B includes an area 65B of material weakness that extends toward the top surface 56B and extends toward the bottom surface and extends toward a second end surface 66B of the body 50B. The area 65B of material weakness extends from an inner portion of the second end portion 52B to the second end surface 66B of the body 50B. This allows the second end portion 52B to be separated into separate end members 67B, 68B by application of a separation force at the area 65B of material weakness of the interproximal dental matrix stabilizer 48B. Preferably, end members 67B, 68B have a rectangular vertical cross-section.

In the interproximal dental matrix stabilizer 48B, the first side surface 54B of the body 50B includes a curved protrusion 75$f$ and a curved protrusion 76$f$. Likewise, the second side surface 55B of the body 50B includes a curved protrusion 75$b$ and a curved protrusion 76$b$.

In interproximal dental matrix stabilizer 48B, the first side surface 54B of the body 50B includes a first curved protrusion 77$f$ located near an intermediate vertical plane of the body 50B. Likewise, the second side surface 55B of the body 50B includes a second curved protrusion 77$b$ located near the intermediate vertical plane of the body 50B. The curved protrusions 77$f$, 77$b$ are beneficial when used with dental matrix 30B having the intermediate horizontally convex section 47B that provides contact with tooth surface that may have inward decay due to the age of the patient. The interproximal dental matrix stabilizer 48B can be formed from a translucent (preferably transparent) elastomeric material such as a silicone or polyurethane elastomer.

Figure 15B:
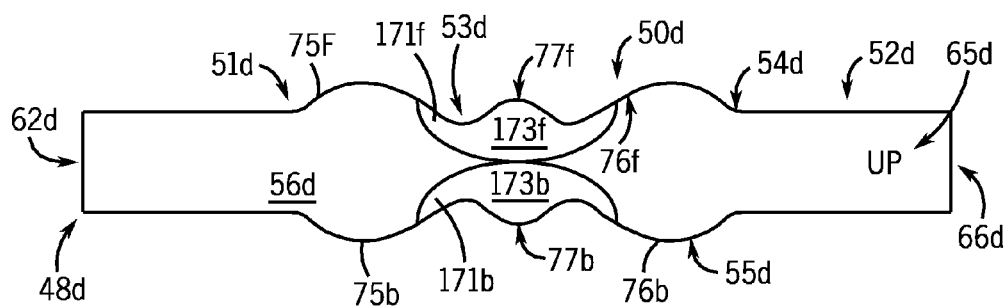
FIG. 15B is a top view of still another embodiment of an interproximal dental matrix stabilizer according to the invention.
Figure 15C:
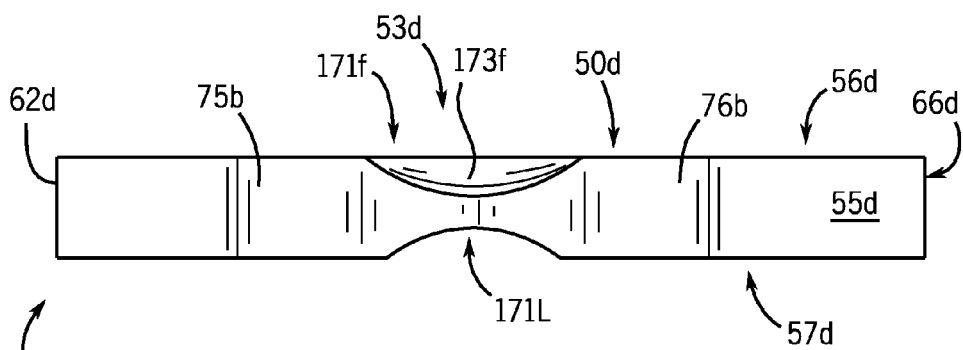
FIG. 15C is a front view of the interproximal dental matrix stabilizer of FIG. 15B.

Turning now to FIGS. 15B and 15C, there is shown yet another embodiment of an interproximal dental matrix stabilizer 48$d$ which includes an elongated translucent (preferably transparent) elastic body 50$d$ having a first end portion 51$d$, a second opposite end portion 52$d$, a middle portion 53$d$ connecting the first end portion 51$d$ and the second end portion 52$d$, a first side surface 54$d$, a second side surface 55$d$, a top surface 56$d$ and a bottom surface 57$d$. The first end portion 51$d$ extends to a first end surface 62$d$ of the body 50$d$. The second end portion 52$d$ extends to a second end surface 66$d$ of the body 50$d$. The top surface 56$d$ may include indicia 65$d$ that indicate which side is placed upward away from the gingival during use.

In the interproximal dental matrix stabilizer 48$d$, the first side surface 54$d$ of the body 50$d$ includes a curved protrusion 75$f$ and a curved protrusion 76$f$. Likewise, the second side surface 55$d$ of the body 50$d$ includes a curved protrusion 75$b$ and a curved protrusion 76$b$.

In interproximal dental matrix stabilizer 48$d$, the first side surface 54$d$ of the body 50$d$ includes a first curved protrusion 77$f$ located near an intermediate vertical plane of the body 50$d$. Likewise, the second side surface 55$d$ of the body 50$d$ includes a second curved protrusion 77$b$ located near the intermediate vertical plane of the body 50$d$. The curved protrusions 77$f$, 77$b$ are beneficial when used with dental matrix 30B having the intermediate horizontally convex section 47B that provides contact with tooth surface that may have inward decay due to the age of the patient. The interproximal dental matrix stabilizer 48$d$ can be formed from a translucent (preferably transparent) elastomeric material such as a silicone or polyurethane elastomer.

The top surface 56$d$ of the body 50$d$ of the interproximal dental matrix stabilizer 48$d$ includes a first pair of upper side-by-side depressions 171$f$, 171$b$ in the middle portion 53$d$ of the body 50$d$. The first pair of upper side-by-side depressions 171$f$, 171$b$ include inwardly curved inner surfaces 173$f$, 173$b$. The bottom surface 57$d$ of the body 50$d$ of the interproximal dental matrix stabilizer 48$d$ includes a lower concavity 171L in the middle portion 53$d$ of the body 50$d$. The lower concavity 171L limits the application of undesired pressure on the interdental gingival when the interproximal dental matrix stabilizer 48$d$ is positioned between a patient's teeth.

Figure 15D:
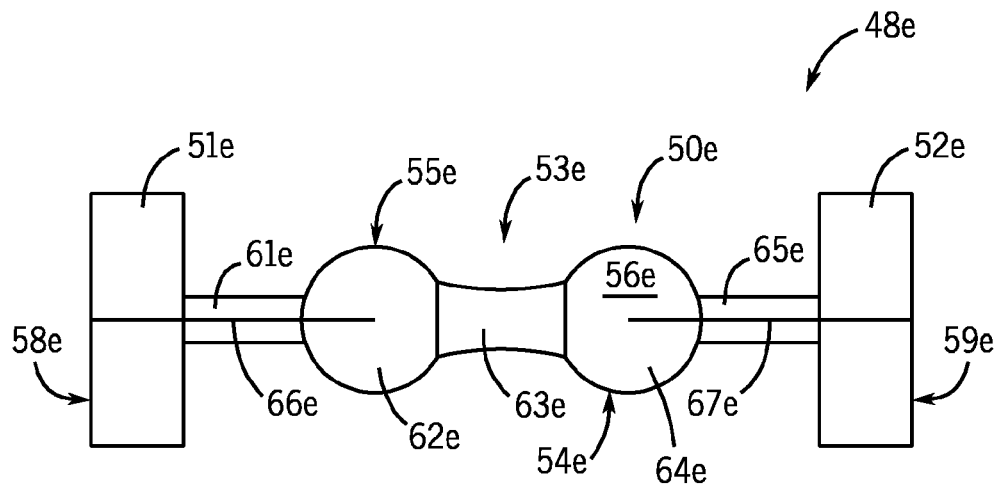
FIG. 15D is a top view of yet another embodiment of an interproximal dental matrix stabilizer according to the invention.
Figure 15E:
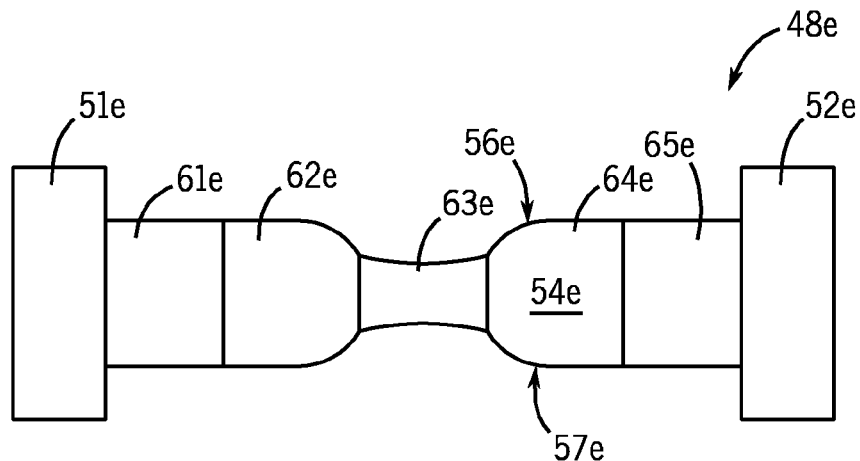
FIG. 15E is a front view of the interproximal dental matrix stabilizer of FIG. 15D.
Figure 15F:
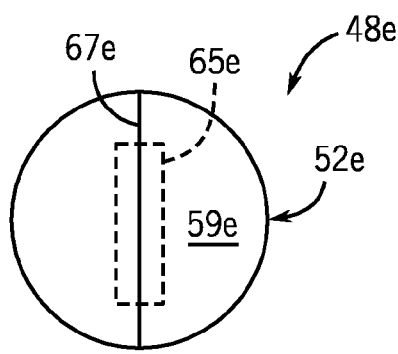
FIG. 15F is a side view of the interproximal dental matrix stabilizer of FIG. 15D.

Turning now to FIGS. 15D to 15F, there is shown another embodiment of an interproximal dental matrix stabilizer 48$e$ which includes an elongated translucent (preferably transparent) elastic body 50$e$ having a disc shaped first end portion 51$e$, a disc shaped second opposite end portion 52$e$, a middle portion 53$e$ connecting the first end portion 51$e$ and the second end portion 52$e$, a first side surface 54$e$, a second side surface 55$e$, a top surface 56$e$ and a bottom surface 57$e$. The first end portion 51e extends to a first end surface 58e of the body 50e. The second end portion 52e extends to a second end surface 59e of the body 50e. The interproximal dental matrix stabilizer 48e can be formed from a translucent (preferably transparent) elastomeric material such as a silicone or polyurethane elastomer.

In the interproximal dental matrix stabilizer 48e, the middle portion 53e includes a generally rectangular (in vertical cross-section) first section 61e, a first intermediate section 62e, a central rod-like section 63e, a second intermediate section 64e, and a generally rectangular (in vertical cross-section) second section 65e. As shown in the top view of FIG. 15D, the section of the first side surface 54e that is part of the first section 61e extends linearly inward from the first end portion 51e to the first intermediate section 62e. The section of the first side surface 54e that is part of the first intermediate section 62e extends in an outward arcuate manner from the first section 61e and then back inward in an arcuate manner to the central section 63e which is tapered inward near its center. The section of the first side surface 54e that is part of the second section 65e extends inward linearly from the second end portion 52e to the second intermediate section 64e. The section of the first side surface 54e that is part of the second intermediate section 64e extends in an outward arcuate manner from the second section 65e and then back inward in an arcuate manner to the central section 63e.

Likewise, the section of the second side surface 55e that is part of the first section 61e extends linearly inward from the first end portion 51e to the first intermediate section 62e. The section of the second side surface 55e that is part of the first intermediate section 62e extends in an outward arcuate manner from the first section 61e and then back inward in an arcuate manner to the central section 63e which is tapered inward near its center. The section of the second side surface 55e that is part of the second section 65e extends inward linearly from the second end portion 52e to the second intermediate section 64e. The section of the second side surface 55e that is part of the second intermediate section 64e extends in an outward arcuate manner from the second section 65e and then back inward in an arcuate manner to the central section 63e.

As shown in the side view of FIG. 15E, the section of the top surface 56e that is part of the first section 61e extends linearly inward from the first end portion 51e to the first intermediate section 62e and through part of the first intermediate section 62e. The section of the top surface 56e that is part of the inward section of the first intermediate section 62e extends inward in an arcuate manner to the central section 63e which is tapered inward near its center. The section of the top surface 56e that is part of the second section 65e extends linearly inward from the second end portion 52e to the second intermediate section 64e and through part of the second intermediate section 64e. The section of the top surface 56e that is part of the inward section of the second intermediate section 64e extends inward in an arcuate manner to the central section 63e.

Likewise, the section of the bottom surface 57e that is part of the first section 61e extends linearly inward from the first end portion 51e to the first intermediate section 62e and through part of the first intermediate section 62e. The section of the bottom surface 57e that is part of the inward section of the first intermediate section 62e extends inward in an arcuate manner to the central section 63e which is tapered inward near its center. The section of the bottom surface 57e that is part of the second section 65e extends linearly inward from the second end portion 52e to the second intermediate section 64e and through part of the second intermediate section 64e. The section of the bottom surface 57e that is part of the inward section of the second intermediate section 64e extends inward in an arcuate manner to the central section 63e.

The body 50e includes an area 66e of material weakness that extends toward the top surface 56e and extends toward the bottom surface 57e and extends to the first end surface 58e of the body 50e. The area 66e of material weakness extends from an inner portion of the first intermediate section 62e to the first end surface 58e of the body 50e. This allows the first end portion 51e, the first section 61e and part of the first intermediate section 62e to be separated into separate end members by application of a separation force at the area 66e of material weakness of the interproximal dental matrix stabilizer 48e. Likewise, the body 50e includes an area 67e of material weakness that extends toward the top surface 56e and extends toward the bottom surface 57e and extends to the second end surface 59e of the body 50e. The area 67e of material weakness extends from an inner portion of the second intermediate section 64e to the second end surface 59e of the body 50e. This allows the second end portion 52e, the second section 65e and part of the second intermediate section 64e to be separated into separate end members by application of a separation force at the area 67e of material weakness of the interproximal dental matrix stabilizer 48e.

Figure 15G:
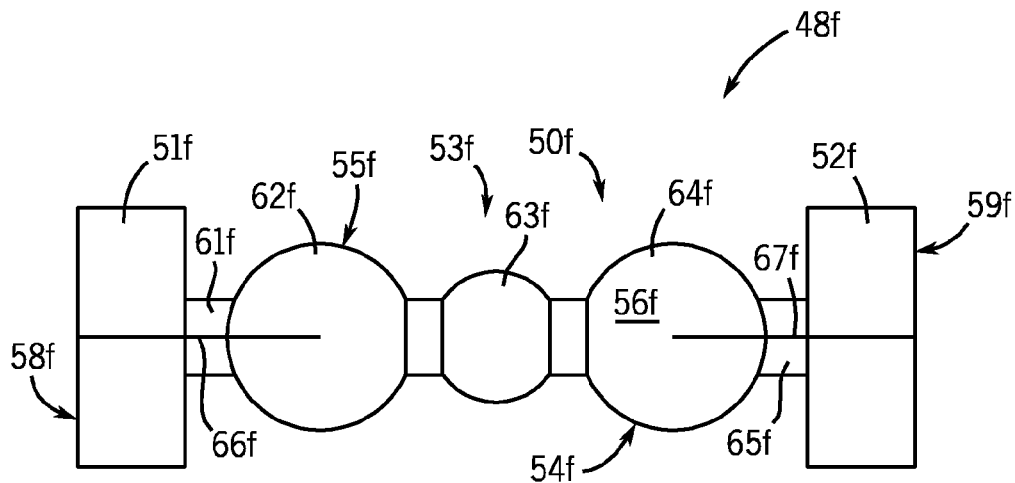
FIG. 15G is a top view of still another embodiment of an interproximal dental matrix stabilizer according to the invention.
Figure 15H:
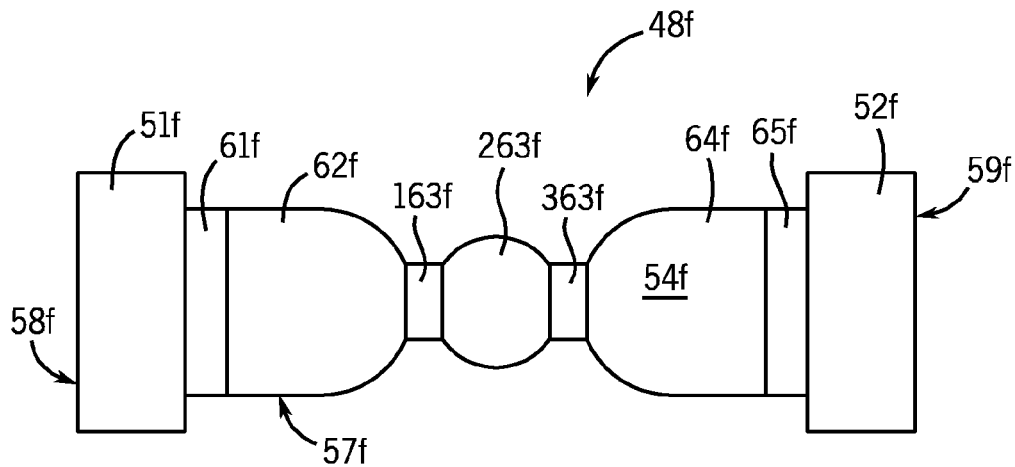
FIG. 15H is a front view of the interproximal dental matrix stabilizer of FIG. 15G.
Figure 15I:
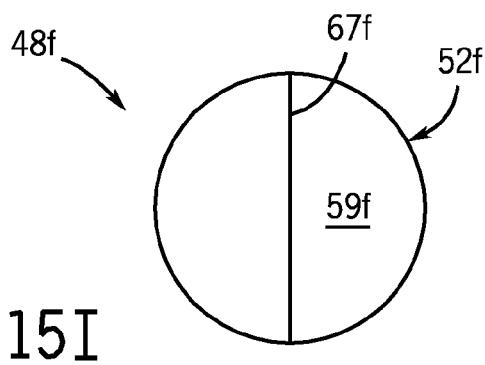
FIG. 15I is a side view of the interproximal dental matrix stabilizer of FIG. 15G.

Turning now to FIGS. 15G to 15I, there is shown another embodiment of an interproximal dental matrix stabilizer 48f which includes an elongated translucent (preferably transparent) elastic body 50f having a disc shaped first end portion 51f, a disc shaped second opposite end portion 52f, a middle portion 53f connecting the first end portion 51f and the second end portion 52f, a first side surface 54f, a second side surface 55f, a top surface 56f and a bottom surface 57f. The first end portion 51f extends to a first end surface 58f of the body 50f. The second end portion 52f extends to a second end surface 59f of the body 50f. The interproximal dental matrix stabilizer 48f can be formed from a translucent (preferably transparent) elastomeric material such as a silicone or polyurethane elastomer.

In the interproximal dental matrix stabilizer 48f, the middle portion 53f includes a generally rectangular (in vertical cross-section) first section 61f, a first intermediate section 62f, a central section 63f, a second intermediate section 64f, and a generally rectangular (in vertical cross-section) second section 65f. As shown in the top view of FIG. 15G, the section of the first side surface 54f that is part of the first section 61f extends linearly inward from the first end portion 51f to the first intermediate section 62f. The section of the first side surface 54f that is part of the first intermediate section 62f extends in an outward arcuate manner from the first section 61f and then back inward in an arcuate manner to the central section 63f which has cylindrical end sections 163f, 363f on both sides of a generally spherical center section 263f. The section of the first side surface 54f that is part of the second section 65f extends inward linearly from the second end portion 52f to the second intermediate section 64f. The section of the first side surface 54f that is part of the second intermediate section 64f extends in an outward arcuate manner from the second section 65f and then back inward in an arcuate manner to the central tubular section 63f.

Likewise, the section of the second side surface 55f that is part of the first section 61f extends linearly inward from the first end portion 51f to the first intermediate section 62f. The section of the second side surface 55f that is part of the first intermediate section 62f extends in an outward arcuate manner from the first section 61f and then back inward in an arcuate manner to the central section 63f which has cylindrical end sections 163f, 363f on both sides of a generally spherical center section 263f. The section of the second side surface 55f that is part of the second section 65f extends inward linearly from the second end portion 52f to the second intermediate section 64f. The section of the second side surface 55f that is part of the second intermediate section 64f extends in an outward arcuate manner from the second section 65f and then back inward in an arcuate manner to the central tubular section 63f.

As shown in the side view of FIG. 15H, the section of the top surface 56f that is part of the first section 61f extends linearly inward from the first end portion 51f to the first intermediate section 62f and through part of the first intermediate section 62f. The section of the top surface 56f that is part of the inward section of the first intermediate section 62f extends inward in an arcuate manner to the central tubular section 63f. The section of the top surface 56f that is part of the second section 65f extends linearly inward from the second end portion 52f to the second intermediate section 64f and through part of the second intermediate section 64f. The section of the top surface 56f that is part of the inward section of the second intermediate section 64f extends inward in an arcuate manner to the central tubular section 63f.

Likewise, the section of the bottom surface 57f that is part of the first section 61f extends linearly inward from the first end portion 51f to the first intermediate section 62f and through part of the first intermediate section 62f. The section of the bottom surface 57f that is part of the inward section of the first intermediate section 62f extends inward in an arcuate manner to the central tubular section 63f. The section of the bottom surface 57f that is part of the second section 65f extends linearly inward from the second end portion 52f to the second intermediate section 64f and through part of the second intermediate section 64f. The section of the bottom surface 57f that is part of the inward section of the second intermediate section 64f extends inward in an arcuate manner to the central tubular section 63f.

The body 50f includes an area 66f of material weakness that extends toward the top surface 56f and extends toward the bottom surface 57f and extends to the first end surface 58f of the body 50f. The area 66f of material weakness extends from an inner portion of the first intermediate section 62f to the first end surface 58f of the body 50f. This allows the first end portion 51f, the first section 61e and part of the first intermediate section 62f to be separated into separate end members by application of a separation force at the area 66f of material weakness of the interproximal dental matrix stabilizer 48f. Likewise, the body 50f includes an area 67f of material weakness that extends toward the top surface 56f and extends toward the bottom surface 57f and extends to the second end surface 59f of the body 50f. The area 67f of material weakness extends from an inner portion of the second intermediate section 64f to the second end surface 59f of the body 50f. This allows the second end portion 52f, the second section 65f and part of the second intermediate section 64f to be separated into separate end members by application of a separation force at the area 67f of material weakness of the interproximal dental matrix stabilizer 48f.

Figure 15J:
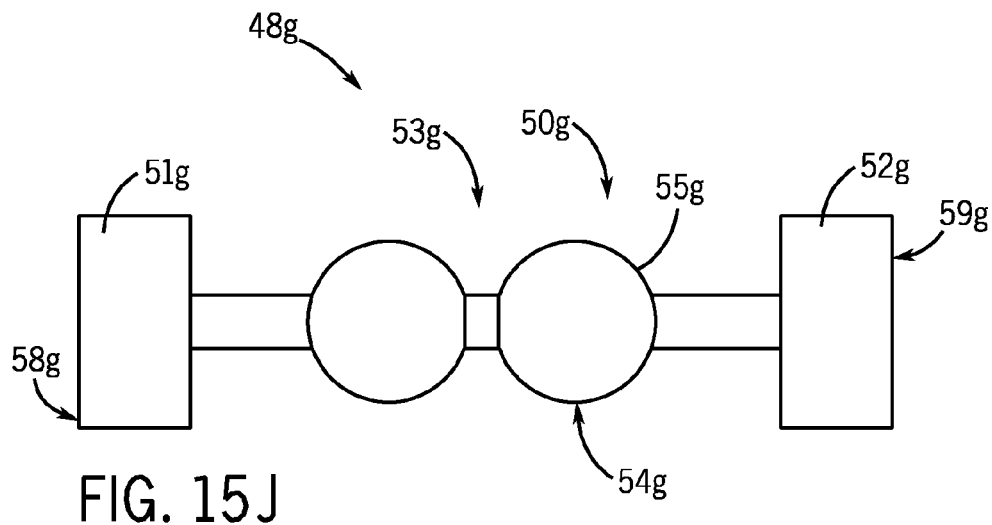
FIG. 15J is a top view of yet another embodiment of an interproximal dental matrix stabilizer according to the invention.
Figure 15K:
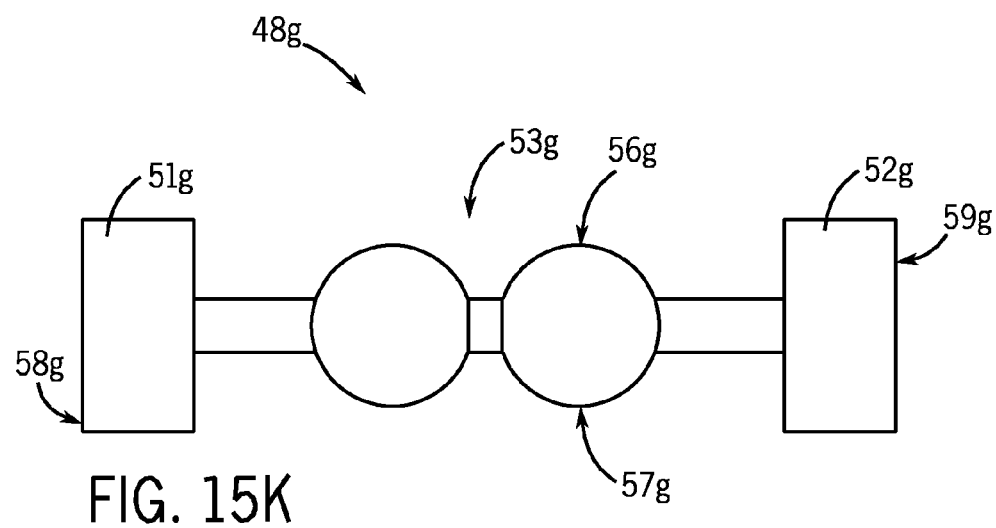
FIG. 15K is a front view of the interproximal dental matrix stabilizer of FIG. 15J.
Figure 15L:
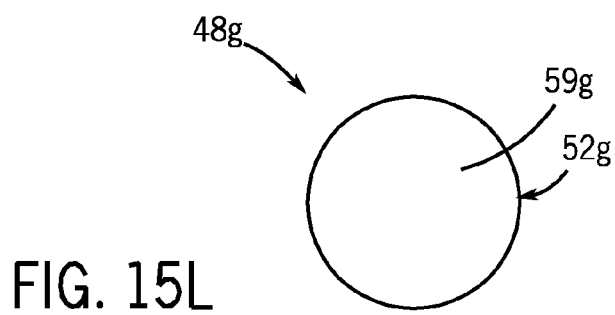
FIG. 15L is a side view of the interproximal dental matrix stabilizer of FIG. 15J.
Figure 15M:
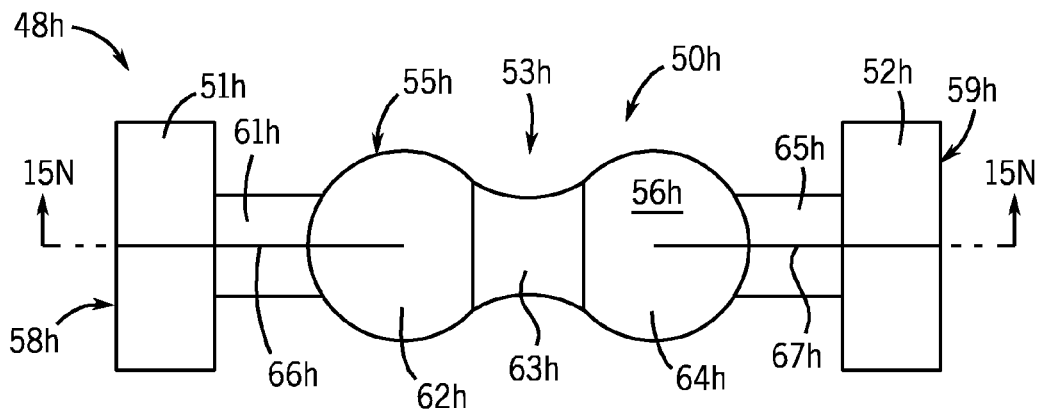
FIG. 15M is a top view of still another embodiment of an interproximal dental matrix stabilizer according to the invention.

Turning now to FIGS. 15J to 15L, there is shown another embodiment of an interproximal dental matrix stabilizer 48g which includes an elongated translucent (preferably transparent) elastic body 50g having a disc shaped first end portion 51g, a disc shaped second opposite end portion 52g, a middle portion 53g connecting the first end portion 51g and the second end portion 52g, a first side surface 54g, a second side surface 55g, a top surface 56g and a bottom surface 57g. The first end portion 51g extends to a first end surface 58g of the body 50g. The second end portion 52g extends to a second end surface 59g of the body 50g. The interproximal dental matrix stabilizer 48g can be formed from a translucent (preferably transparent) elastomeric material such as a silicone or polyurethane elastomer.

In the interproximal dental matrix stabilizer 48g, the middle portion 53g includes a generally cylindrical first section 61g, a first spherical intermediate section 62g, a central cylindrical section 63g, a second spherical intermediate section 64g, and a generally cylindrical second section 65g.

Turning now to FIGS. 15M to 15P there is shown another embodiment of an interproximal dental matrix stabilizer 48h which includes an elongated translucent (preferably transparent) elastic body 50h having a generally disc shaped first end portion 51h, a generally disc shaped second opposite end portion 52h, a middle portion 53h connecting the first end portion 51h and the second end portion 52h, a first side surface 54h, a second side surface 55h, a top surface 56h and a bottom surface 57h. The first end portion 51h extends to a first end surface 58h of the body 50h. The second end portion 52h extends to a second end surface 59h of the body 50h. The interproximal dental matrix stabilizer 48h can be formed from a translucent (preferably transparent) elastomeric material such as a silicone or polyurethane elastomer.

In the interproximal dental matrix stabilizer 48h, the middle portion 53h includes a generally rectangular (in vertical cross-section) first section 61h, a first intermediate section 62h, a central rod-like section 63h, a second intermediate section 64h, and a generally rectangular (in vertical cross-section) second section 65h. As shown in the top view of FIG. 15M, the section of the first side surface 54h that is part of the first section 61h extends linearly inward from the first end portion 51h to the first intermediate section 62h. The section of the first side surface 54h that is part of the first intermediate section 62h extends in an outward arcuate manner from the first section 61h and then back inward in an arcuate manner to the central section 63h which is tapered inward near its center. The section of the first side surface 54h that is part of the second section 65h extends inward linearly from the second end portion 52h to the second intermediate section 64h. The section of the first side surface 54h that is part of the second intermediate section 64h extends in an outward arcuate manner from the second section 65h and then back inward in an arcuate manner to the central section 63h.

Likewise, the section of the second side surface 55h that is part of the first section 61h extends linearly inward from the first end portion 51h to the first intermediate section 62h. The section of the second side surface 55h that is part of the first intermediate section 62h extends in an outward arcuate manner from the first section 61h and then back inward in an arcuate manner to the central section 63h which is tapered inward near its center. The section of the second side surface 55h that is part of the second section 65h extends inward linearly from the second end portion 52h to the second intermediate section 64h. The section of the second side surface 55h that is part of the second intermediate section 64h extends in an outward arcuate manner from the second section 65h and then back inward in an arcuate manner to the central section 63h.

Figure 15N:
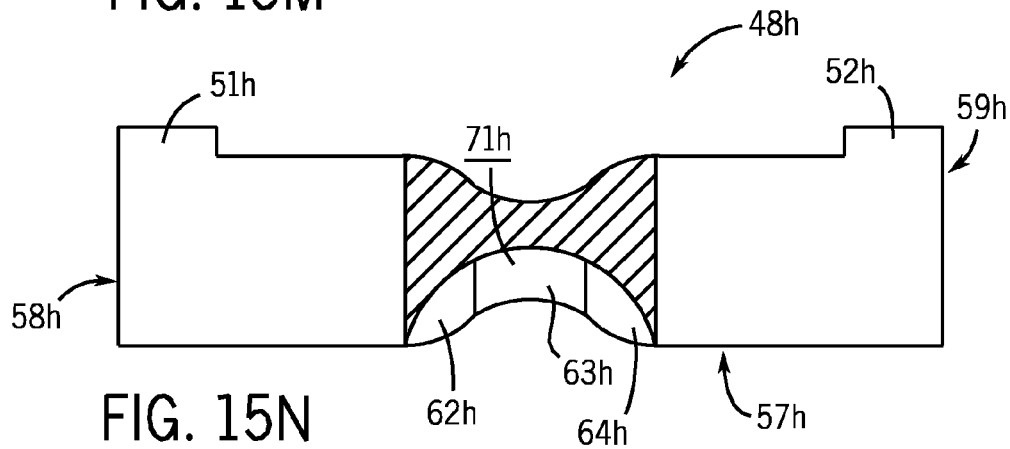
FIG. 15N is a cross-sectional view of the interproximal dental matrix stabilizer of FIG. 15M taken along line 15N-15N of FIG. 15M.
Figure 15O:
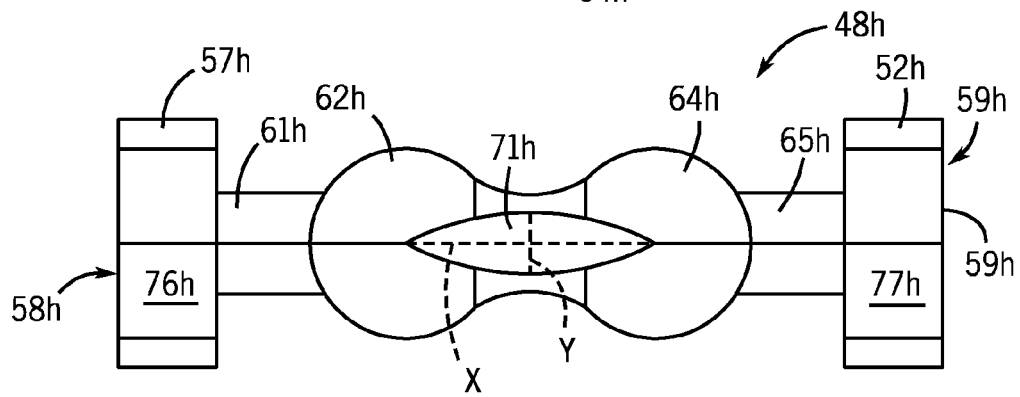
FIG. 15O is a bottom view of the interproximal dental matrix stabilizer of FIG. 15M.
Figure 15P:
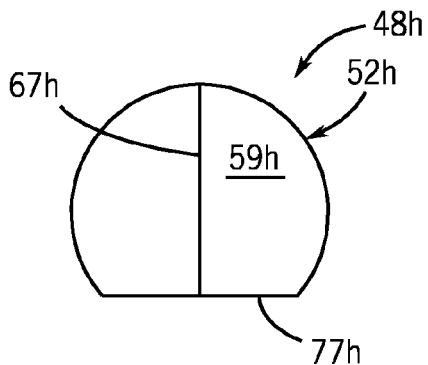
FIG. 15P is a side view of the interproximal dental matrix stabilizer of FIG. 15M.
Figure 15Q:
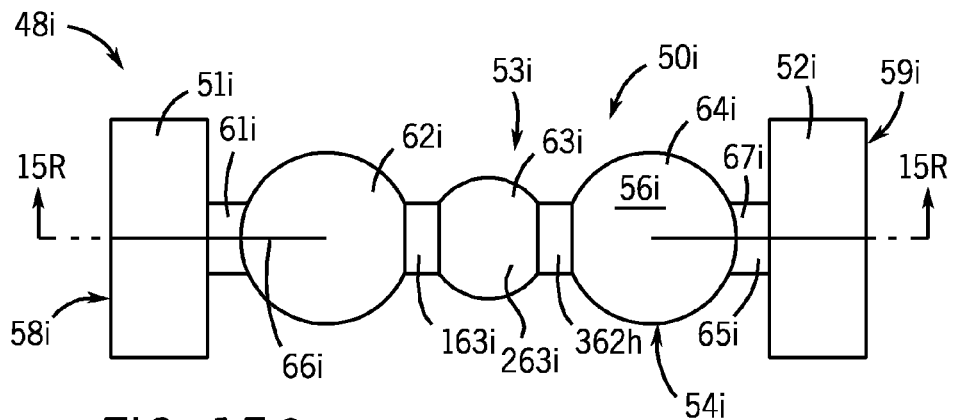
FIG. 15Q is a top view of yet another embodiment of an interproximal dental matrix stabilizer according to the invention.

As shown in the side view of FIG. 15N, the section of the top surface 56h that is part of the first section 61h extends linearly inward from the first end portion 51h to the first intermediate section 62h and through part of the first intermediate section 62h. The section of the top surface 56h that is part of the inward section of the first intermediate section 62h extends inward in an arcuate manner to the central section 63e which is tapered inward near its center. The section of the top surface 56h that is part of the second section 65h extends linearly inward from the second end portion 52h to the second intermediate section 64h and through part of the second intermediate section 64h. The section of the top surface 56h that is part of the inward section of the second intermediate section 64h extends inward in an arcuate manner to the central section 63h.

Likewise, the section of the bottom surface 57h that is part of the first section 61h extends linearly inward from the first end portion 51h to the first intermediate section 62h and through part of the first intermediate section 62h. The section of the bottom surface 57h that is part of the inward section of the first intermediate section 62h extends inward in an arcuate manner to the central section 63h which is tapered inward near its center. The section of the bottom surface 57h that is part of the second section 65h extends linearly inward from the second end portion 52h to the second intermediate section 64h and through part of the second intermediate section 64h. The section of the bottom surface 57h that is part of the inward section of the second intermediate section 64e extends inward in an arcuate manner to the central section 63h.

The body 50h includes an area 66h of material weakness that extends toward the top surface 56h and extends toward the bottom surface 57h and extends to the first end surface 58h of the body 50h. The area 66h of material weakness extends from an inner portion of the first intermediate section 62h to the first end surface 58h of the body 50h. This allows the first end portion 51h, the first section 61h and part of the first intermediate section 62h to be separated into separate end members by application of a separation force at the area 66h of material weakness of the interproximal dental matrix stabilizer 48h. Likewise, the body 50h includes an area 67h of material weakness that extends toward the top surface 56h and extends toward the bottom surface 57h and extends to the second end surface 59h of the body 50h. The area 67h of material weakness extends from an inner portion of the second intermediate section 64h to the second end surface 59h of the body 50h. This allows the second end portion 52h, the second section 65h and part of the second intermediate section 64h to be separated into separate end members by application of a separation force at the area 67h of material weakness of the interproximal dental matrix stabilizer 48h.

In the interproximal dental matrix stabilizer 48h, there is an inward concavity 71h in the bottom surface 57h in an inward section of the first intermediate section 62h, the central section 63h, and an inward section of the second intermediate section 64h. The inward concavity 71h has a longitudinal axis X and a lateral axis Y transverse to the longitudinal axis X. The longitudinal axis X extend toward the first end portion 51h and the second end portion 52h. The longitudinal axis X is longer than the lateral axis Y. The 71h limits the application of undesired pressure on the interdental gingival when the interproximal dental matrix stabilizer 48h is positioned between a patient's teeth. Also, the first end portion 51h has a flat bottom surface 76h, and the second end portion 52h has a flat bottom surface 77h.

Turning now to FIGS. 15Q to 15T, there is shown another embodiment of an interproximal dental matrix stabilizer 48i which includes an elongated translucent (preferably transparent) elastic body 50i having a generally disc shaped first end portion 51i, a generally disc shaped second opposite end portion 52i, a middle portion 53i connecting the first end portion 51i and the second end portion 52i, a first side surface 54i, a second side surface 55i, a top surface 56i and a bottom surface 57i. The first end portion 51i extends to a first end surface 58i of the body 50i. The second end portion 52i extends to a second end surface 59i of the body 50i. The interproximal dental matrix stabilizer 48i can be formed from a translucent (preferably transparent) elastomeric material such as a silicone or polyurethane elastomer.

In the interproximal dental matrix stabilizer 48i, the middle portion 53i includes a generally rectangular (in vertical cross-section) first section 61i, a first intermediate section 62i, a central section 63i, a second intermediate section 64i, and a generally rectangular (in vertical cross-section) second section 65i. As shown in the top view of FIG. 15Q, the section of the first side surface 54i that is part of the first section 61i extends linearly inward from the first end portion 51i to the first intermediate section 62i. The section of the first side surface 54i that is part of the first intermediate section 62i extends in an outward arcuate manner from the first section 61i and then back inward in an arcuate manner to the central section 63i which has cylindrical end sections 163i, 363i on both sides of a generally spherical center section 263i. The section of the first side surface 54i that is part of the second section 65i extends inward linearly from the second end portion 52i to the second intermediate section 64i. The section of the first side surface 54i that is part of the second intermediate section 64i extends in an outward arcuate manner from the second section 65i and then back inward in an arcuate manner to the central tubular section 63i.

Likewise, the section of the second side surface 55i that is part of the first section 61i extends linearly inward from the first end portion 51i to the first intermediate section 62i. The section of the second side surface 55i that is part of the first intermediate section 62i extends in an outward arcuate manner from the first section 61i and then back inward in an arcuate manner to the central section 63i which has cylindrical end sections 163i, 363i on both sides of a generally spherical center section 263i. The section of the second side surface 55i that is part of the second section 65i extends inward linearly from the second end portion 52i to the second intermediate section 64i. The section of the second side surface 55i that is part of the second intermediate section 64i extends in an outward arcuate manner from the second section 65i and then back inward in an arcuate manner to the central tubular section 63i.

Figure 15R:
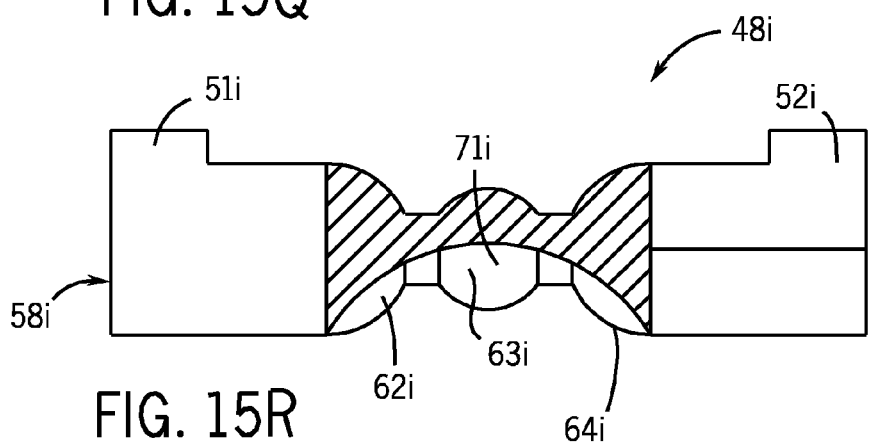
FIG. 15R is a cross-sectional view of the interproximal dental matrix stabilizer of FIG. 15Q taken along line 15R-15R of FIG. 15Q.
Figure 15S:
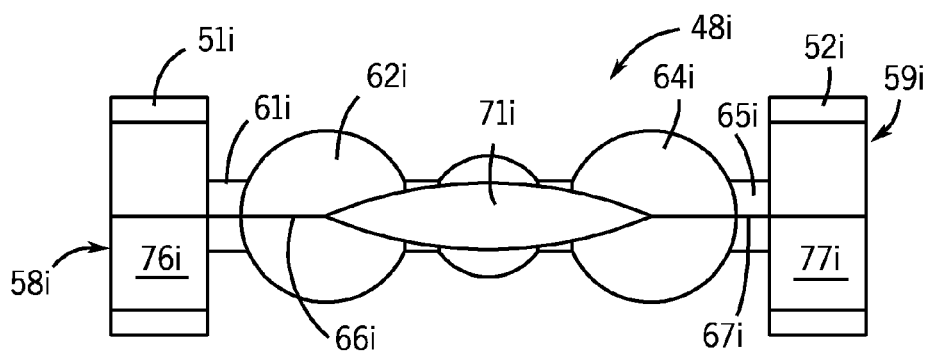
FIG. 15S is a bottom view of the interproximal dental matrix stabilizer of FIG. 15Q.
Figure 15T:
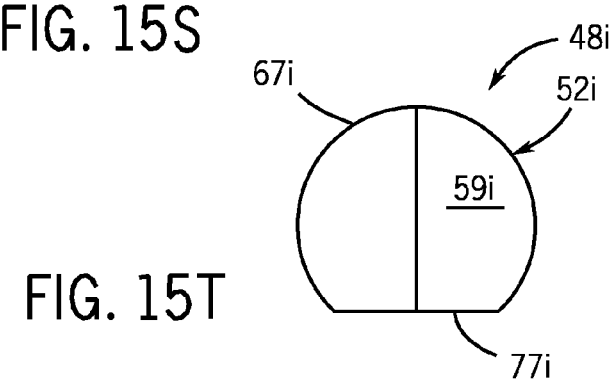
FIG. 15T is a side view of the interproximal dental matrix stabilizer of FIG. 15Q.

As shown in the side view of FIG. 15R, the section of the top surface 56i that is part of the first section 61i extends linearly inward from the first end portion 51i to the first intermediate section 62i and through part of the first intermediate section 62i. The section of the top surface 56i that is part of the inward section of the first intermediate section 62i extends inward in an arcuate manner to the central tubular section 63i. The section of the top surface 56i that is part of the second section 65i extends linearly inward from the second end portion 52i to the second intermediate section 64i and through part of the second intermediate section 64i. The section of the top surface 56i that is part of the inward section of the second intermediate section 64i extends inward in an arcuate manner to the central tubular section 63i.

Likewise, the section of the bottom surface 57i that is part of the first section 61i extends linearly inward from the first end portion 51i to the first intermediate section 62i and through part of the first intermediate section 62i. The section of the bottom surface 57i that is part of the inward section of the first intermediate section 62i extends inward in an arcuate manner to the central tubular section 63i. The section of the bottom surface 57i that is part of the second section 65i extends linearly inward from the second end portion 52i to the second intermediate section 64i and through part of the second intermediate section 64i. The section of the bottom surface 57i that is part of the inward section of the second intermediate section 64i extends inward in an arcuate manner to the central tubular section 63i.

The body 50*i* includes an area 66*i* of material weakness that extends toward the top surface 56*i* and extends toward the bottom surface 57*i* and extends to the first end surface 58*i* of the body 50*i*. The area 66*i* of material weakness extends from an inner portion of the first intermediate section 62*i* to the first end surface 58*i* of the body 50*i*. This allows the first end portion 51*i*, the first section 61*i* and part of the first intermediate section 62*i* to be separated into separate end members by application of a separation force at the area 66*i* of material weakness of the interproximal dental matrix stabilizer 48*i*. Likewise, the body 50*i* includes an area 67*i* of material weakness that extends toward the top surface 56*i* and extends toward the bottom surface 57*i* and extends to the second end surface 59*i* of the body 50*i*. The area 67*i* of material weakness extends from an inner portion of the second intermediate section 64*i* to the second end surface 59*i* of the body 50*i*. This allows the second end portion 52*i* the second section 65*i* and part of the second intermediate section 64*i* to be separated into separate end members by application of a separation force at the area 67*i* of material weakness of the interproximal dental matrix stabilizer 48*i*.

In the interproximal dental matrix stabilizer 48*i*, there is an inward concavity 71*i* in the bottom surface 57*i* in an inward section of the first intermediate section 62*i*, the central section 63*i*, and an inward section of the second intermediate section 64*i*. The 71*i* limits the application of undesired pressure on the interdental gingival when the interproximal dental matrix stabilizer 48*h* is positioned between a patient's teeth. Also, the first end portion 51*i* has a flat bottom surface 76*i*, and the second end portion 52*i* has a flat bottom surface 77*i*.

Referring now to FIGS. 4-8, the placement of the interproximal dental matrix stabilizer 48 is shown during a method according to the invention for the restoration of a tooth. After the dental matrix 30 is positioned as shown in FIG. 4, the dentist stretches the dental matrix stabilizer 48 in directions A and B shown in FIG. 4. The dental matrix stabilizer 48 can be stretched by inserting the ends of a pliers in the first throughhole 58 and the second throughhole 59 of the dental matrix stabilizer 48 and opening the ends of the pliers. Alternatively, the dentist can grab and pull apart the end portions 51 and 52 of the dental matrix stabilizer 48 in directions A and B shown in FIG. 4. The stretching of the dental matrix stabilizer 48 leads to a thinning of the middle portion 53 of the dental matrix stabilizer 48 such that the dental matrix stabilizer 48 can be inserted between teeth 12 and 24 by movement in direction C of FIG. 4. The dental matrix stabilizer 48 then biases the base portion 42 of the dental matrix 30 against the tooth 12 as shown in FIG. 5.

Figure 6:
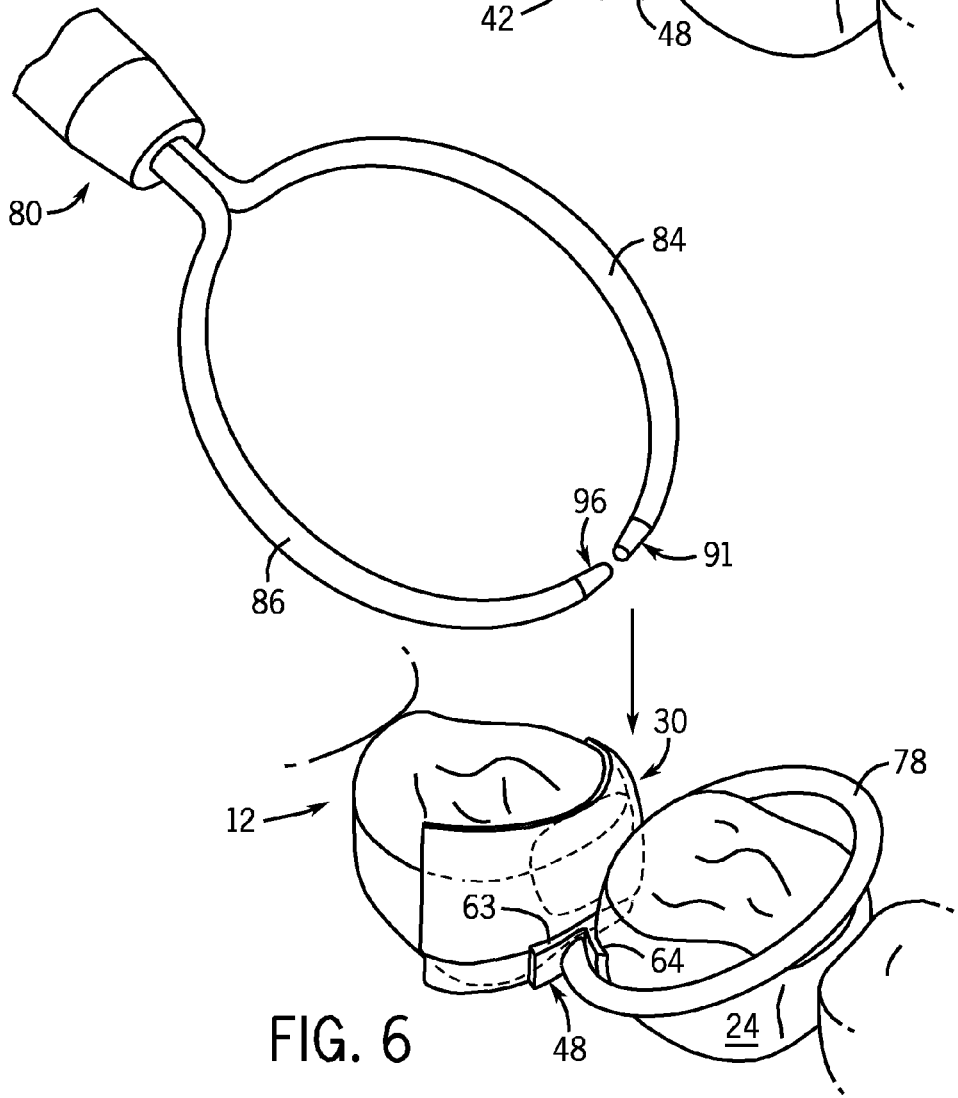
FIG. 6 is a top perspective view of the beginning of the light curing step of the method according to the invention.
Figure 7:
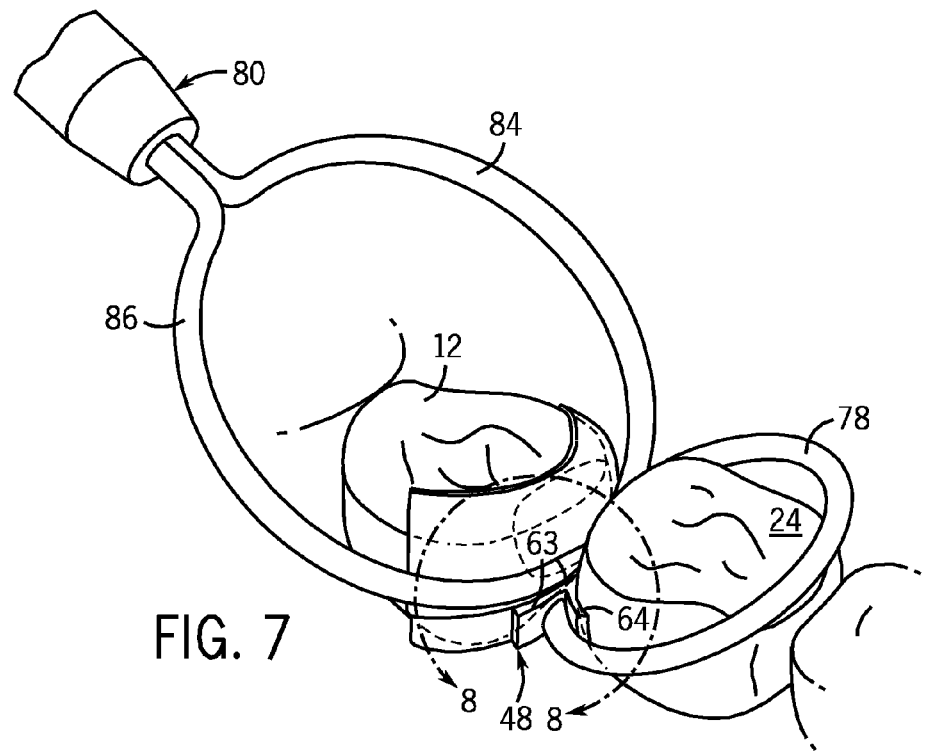
FIG. 7 is a top perspective view of the light curing step of the method according to the invention.

After the dental matrix stabilizer 48 is placed against the base portion 42 of the dental matrix 30, the dentist separates the first end portion 51 of the dental matrix stabilizer 48 into separate end members 63, 64 by application of a separation force at the area 61 of material weakness of the interproximal dental matrix stabilizer 48. Likewise, the dentist separates the second end portion 52 of the dental matrix stabilizer 48 into separate end members 67,68 by application of a separation force at the area 65 of material weakness of the interproximal dental matrix stabilizer 48. The dentist then flexes the separator ring 78 open and then places the ends 79 of the separator ring 78 between the separate end members 63, 64 and separate end members 67,68 of the dental matrix stabilizer 48 as shown in FIGS. 6 and 7. As shown in FIG. 7, the end member 63 biases the base portion 42 of the dental matrix 30 against the tooth 12 and the end member 64 contacts the base of the tooth 24. In a similar manner, the end member 67 biases the base portion 42 of the dental matrix 30 against the tooth 12 and the end member 68 contacts the base of the tooth 24.

Optionally, two separator rings can be used with one separator ring applying adaptation pressure on the dental matrix 30 and the other separator ring applying adaptation pressure on the dental matrix stabilizer.

The dental matrix stabilizers 48A, 48B, 48*d*, 48*e*, 48*f*, 48*g*, 48*h* can be placed in a similar manner. For example, no pliers is needed for placing dental matrix stabilizer 48B of FIG. 15 as the dentist can grab and pull apart the end portions 51B and 52B of the dental matrix stabilizer 48B in directions A and B shown in FIG. 4 when placing dental matrix stabilizer 48B. Also, the areas of material weakness 61, 61A, 61B, 65, 65A, 65B of the interproximal dental matrix stabilizers 48, 48A and 48B may not be present in the interproximal dental matrix stabilizers 48, 48A and 48B. In these embodiments, the dentist can separate the first end portion and the second end portion of the dental matrix stabilizers 48, 48A, 48B into separate end members (if desired) by cutting along a line marked at 61 and 65 in FIG. 9.

Figure 8:
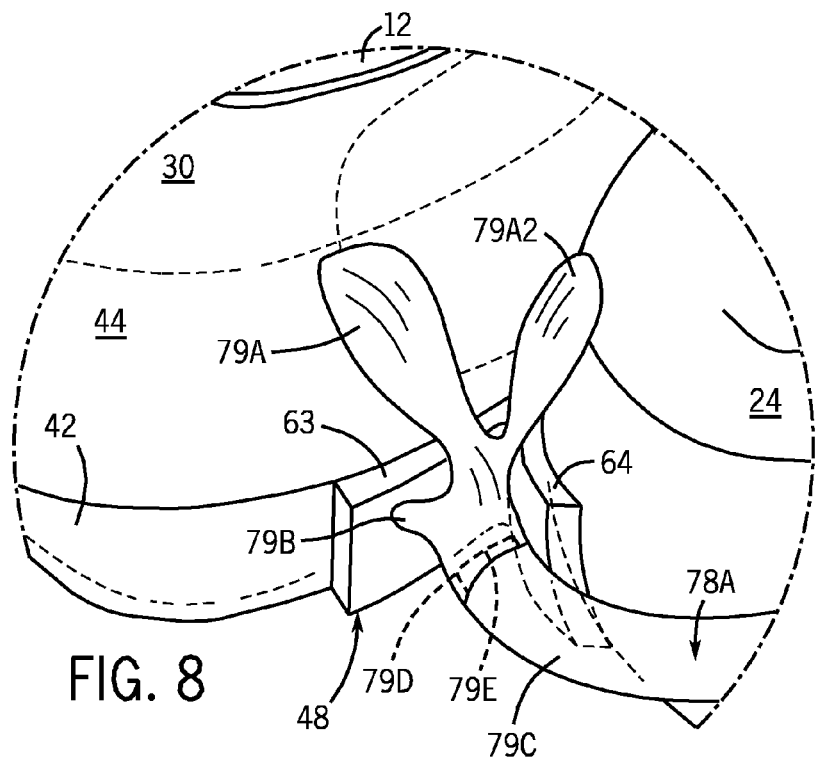
FIG. 8 is a detailed view taken along line 8-8 of FIG. 7 showing an alternative separator ring according to the invention.

Looking at FIG. 8, alternative ends 79A, 79A2, 79B, are shown on a separator ring 78A having an elastic ring 79C. The ends 79A, 79A2, 79B, of separator ring 78A are spaced apart such that end 79B can be placed between the separate end members 63, 64 of the dental matrix stabilizer 48 and the end 79A can bias the upper portion 44 of the dental matrix 30 and the end 79A2 can bias the tooth 24 when the separator ring 78A is placed on the dental matrix stabilizer 48. Preferably, the ends 79A, 79A2, 79B of separator ring 78A are formed from a translucent (preferably transparent) material to provide for passage of light from the dental curing light 80. The elastic ring 79C of the separator ring 78A can be opaque or translucent. Suitable materials for the ends 79A, 79A2, 79B of the separator ring 78A are elastic polymeric materials and suitable materials for the ring 79C of the separator ring 78A are polymeric, metallic or composite materials. In one embodiment, the ends 79A, 79A2, 79B of separator ring 78A have a recess 79D that accepts a protrusion 79E of the elastic ring 79C in an interference fit such that the ends 79A, 79A2, 79B of separator ring 78A are removable from the elastic ring 79C. While the ends 79A, 79A2, 79B of the separator ring 78A are shown having a generally J-shaped or L-shaped configuration in FIG. 8, the ends 79A, 79A2, 79B can also have a V-shaped configuration, or any other spaced apart configuration that allows for the application of force to end members of the dental matrix stabilizers 48, 48A, 48B and to the upper portion 44 of the dental matrix 30 when the separator ring 78A is placed on the dental matrix stabilizer.

An example dental curing light 80 used in the method of the invention will be now be described in further detail. Looking at FIG. 12, there is shown a dental curing light 80 according to the invention. The dental curing light 80 includes an electrical power supply (not shown) and a light source (not shown) in electrical communication with the electrical power supply. The light source can be a high intensity light emitting diode as is known in the art. The dental curing light 80 uses the typical 400-500 nanometer wavelength that is used in curing light curable composite materials. Single wavelength devices are preferred. The dental curing light 80 includes a light guide including a proximal section 82, a first distal section 84 extending from the proximal section 84, and a second distal section 86 extending from the proximal section 82. The proximal section 82 is in optical communication with the light source, the first distal section 84 and the second distal section 86. The first distal section 84 has a first distal end 85, and the second distal section 86 has a second distal end 87. The first distal section 84 and the second distal section 86 are formed from a flexible material which retains shape in a bent condition such that the first distal section 84 and the second distal section 86 can be bent to emit light in a various selected directions. An example flexible material is one that includes deformable metal wires that retain their shape upon bending in a matrix of an elastomer such as silicone or polyurethane.

The dental curing light 80 further includes a first light tip 91 having a first base 92 removably connected to the first distal end 85 of the first distal section 84 of the light guide. The first light tip 91 includes a first hollow tubular opaque body 93 having a first aperture 94 for emitting light. The first body 93 is formed from a flexible material which retains shape in a bent condition such that the first hollow body 93 can be bent to emit light in a first selected direction from the first aperture 94. An example flexible material is one that includes deformable metal wires that retain their shape upon bending in a matrix of an elastomer such as silicone or polyurethane. The outside diameter of the first light tip 91 tapers inward from the first base 92 toward the first aperture 94. In one embodiment, the first light tip 91 has a recess 105 that accepts a protrusion 106 of the first distal end 85 of the first distal section 84 of the light guide in an interference fit such that the first light tip 91 is removable from the first distal end 85 of the first distal section 84 of the light guide.

The dental curing light 80 also includes a second light tip 96 having a second base 97 removably connected to the second distal end 87 of the second distal section 86 of the light guide. The second light tip 96 includes a second hollow tubular opaque body 98 having a second aperture 99 for emitting light. The second body 98 is formed from a flexible material which retains shape in a bent condition such that the second hollow body 98 can be bent to emit light in a second selected direction from the second aperture 99. An example flexible material is one that includes deformable metal wires that retain their shape upon bending in a matrix of an elastomer such as silicone or polyurethane. The outside diameter of the second light tip 96 tapers inward from the second base 97 toward the second aperture 99. In one embodiment, the second light tip 96 has a recess 115 that accepts a protrusion 116 of the second distal end 87 of the second distal section 86 of the light guide in an interference fit such that the second light tip 96 is removable from second distal end 87 of the second distal section 86 of the light guide.

In the dental curing light 80, the electrical power supply, the light source and the proximal section 82 of the light guide can be encased in a housing 101. Alternatively, the electrical power supply and the light source are encased in the housing 101 and the proximal section 82 of the light guide is at least partially outside the housing 101.

The dental curing light 80 can be used in a method for the restoration of a tooth having a hollow cavity preparation in an interproximal surface of the tooth. In the method, a light-curable restorative material is placed in the cavity preparation, and light is directed from the first light tip 91 of the dental curing light 80 at a buccal portion of the restorative material in the cavity preparation. Simultaneously lights is directed from the second light tip 96 of the dental curing light 80 at a lingual portion of the restorative material in the cavity preparation. The first light tip 91 and the second light tip 96 can be bent such that light can be directed at the buccal portion and the lingual portion of the restorative material in the cavity preparation. The use of light curing is generally preferred over chemical curing as the resulting cured material is color stable.

Figure 12A:
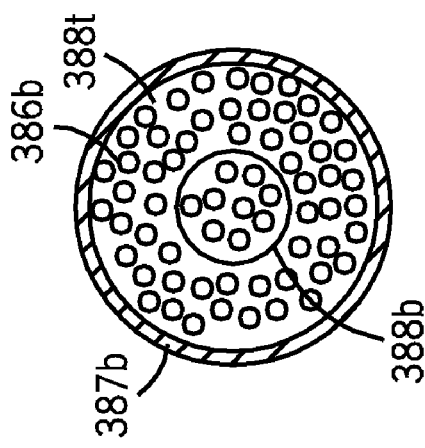
FIG. 12A is a top view of another version of a light curing device according to the invention.
Figure 12A:
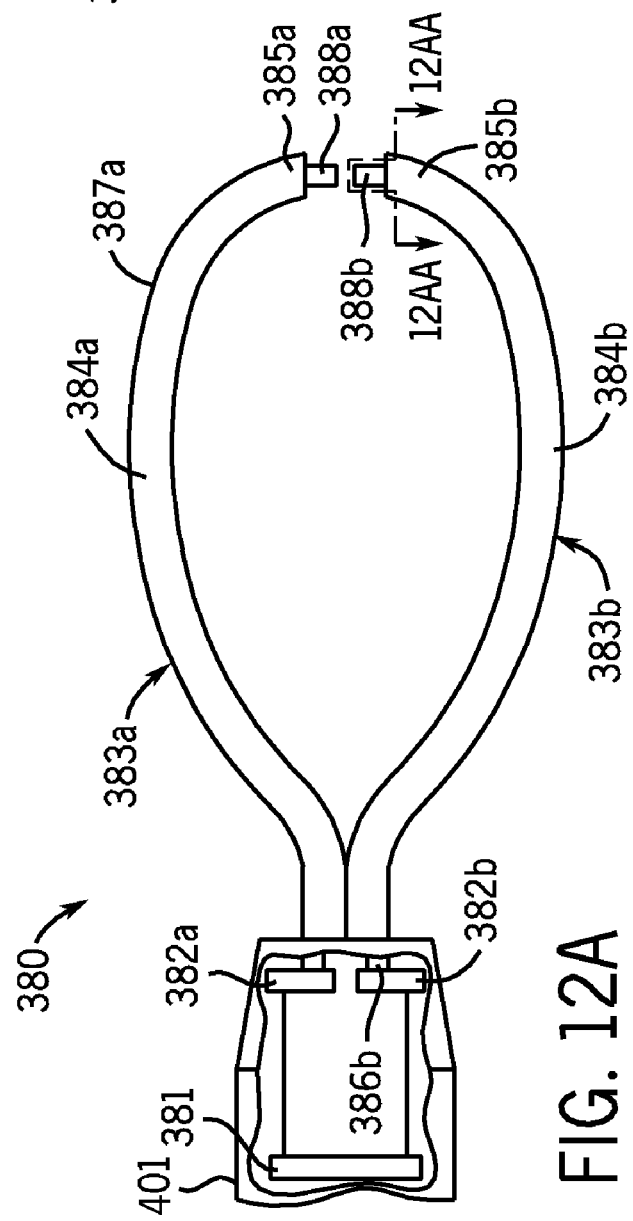
Figure 12B:
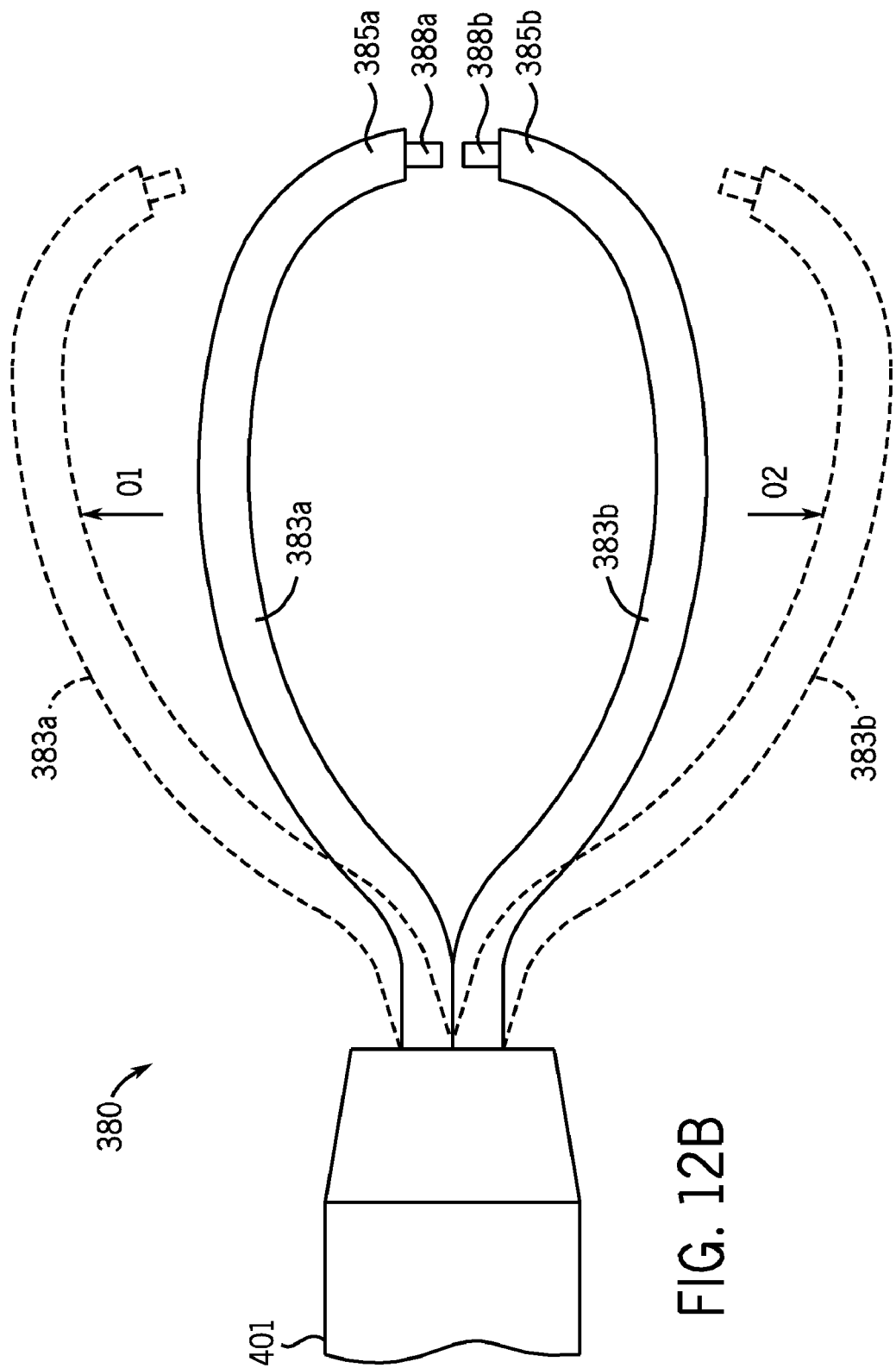
FIG. 12B is a top view of the light curing device of FIG. 12A showing the light guides in phantom in their flexed position.

Turning now to FIG. 12A, another example dental curing light 380 that may be used in the method of the invention will be now be described in further detail. The dental curing light 380 includes an electrical power supply 381 (such as an AC power supply or a rechargeable battery or a primary battery) and light sources 382a, 382b in electrical communication with the electrical power supply 381. The electrical power supply 381 and the light sources 382a, 382b are contained in a housing 401. The light sources 382a, 382b can be high intensity light emitting diodes as is known in the art. The dental curing light 380 can use the typical 400-500 nanometer wavelength that is used in curing light curable composite materials. Plasma arc, halogen, and laser light sources are also suitable.

The dental curing light 380 includes a first light guide 383a having a first distal section 384a and a first distal end 385a. A first light conducting optical fiber bundle (not shown, similar to 386b) is contained within a first sleeve of the first light guide 383a. The first light conducting optical fiber bundle conducts light from the light source 382a to a transparent or translucent first tip 388a of the first light guide 383a. The first tip 388a of the first light guide 383a can have a 3 millimeter circle diameter and can extend axially about 3 millimeters beyond the sleeve 387a of the first light guide 383a.

The dental curing light 380 also includes a second light guide 383b having a second distal section 384b and a second distal end 385b. A second circular light conducting optical fiber bundle 386b (see FIG. 12AA) is contained within a second sleeve 387b of the second light guide 383b. The second light conducting optical fiber bundle 386b conducts light from the light source 382b to a transparent or translucent second tip 388b of the second light guide 383b. The second tip 388b of the second light guide 383b can have a 3 millimeter circle diameter and can extend about 3 millimeters beyond the sleeve 387b of the second light guide 383b. The second tip 388b extends outward from an integral transparent or translucent disc-like flange 388t. The second light conducting optical fiber bundle 386b also conducts light from the light source 382b to the disc-like flange 388t.

In one version of the dental curing light 380, the first sleeve 387a and the second sleeve 387b are formed from a flexible material which retains shape in a bent condition such that the first sleeve 387a and the second sleeve 387b can be bent to emit light in a various selected directions. An example flexible material is one that includes deformable metal wires that retain their shape upon bending in a matrix of an elastomer such as silicone or polyurethane.

In another version of the dental curing light 380, the first sleeve 387a and the second sleeve 387b are formed from a rigid material. Looking at FIG. 12B, the operation of such a dental curing light 380 is shown. The light source 382a and first light guide 383a are mounted on a hinge assembly such that the light source 382a and first light guide 383a may pivot in direction O1 shown in FIG. 12B. Likewise, the light source 382b and second light guide 383b are mounted on a hinge assembly such that the light source 382b and second light guide 383b may pivot in direction O2 shown in FIG. 12B. The hinge assemblies are spring-biased inward such that the rest position for the first light guide 383a and the second light guide 383b are depicted in full lines in FIG. 12B. When the first light guide 383a and the second light guide 383b are flexed outward against the bias of the hinge assemblies, the first light guide 383a and the second light guide 383 are in the flexed positions depicted in dashed lines in FIG. 12B.

The dental curing light 380 can be used in a method for the restoration of a tooth having a hollow cavity preparation in an interproximal surface of the tooth. In the method, a light-curable restorative material is placed in the cavity preparation. The first light guide 383a and the second light guide 383b can be flexed outward as described with reference to FIG. 12B, and thereafter the first light guide 383a and the second light guide 383b are released such that the first tip 388a of the dental curing light 380 assumes a position near a buccal portion of the restorative material in the cavity preparation and the second tip 388b of the dental curing light 380 assumes a position near a lingual portion of the restorative material in the cavity preparation. Alternatively, when the first sleeve 387a and the second sleeve 387b comprise flexible materials, the first sleeve 387a and the second sleeve 387b can be bent such that light can be directed at the buccal portion and the lingual portion of the restorative material in the cavity preparation by the first tip 388a and the second tip 388b, preferably at a distance of less than 6 millimeters, most preferably at 3-4 millimeters. The proximity of the light guides or LEDs can be important as moving as little as 3 millimeters away from the surface affects photon transfer. The hinging of the light guides along with the dual surface profiles of the tips allows more intimate positioning than with previous lights. Preferably, in the relaxed position, the first tip 388a and the second tip 388b are about 4 to about 15 millimeters apart. In the case of incisor restoration, the first tip 388a and the second tip 388b are most preferably about 4 to about 15 millimeters apart. In the case of molar restoration, the first tip 388a and the second tip 388b are most preferably about 4 to about 15 millimeters apart.

Figure 12C:
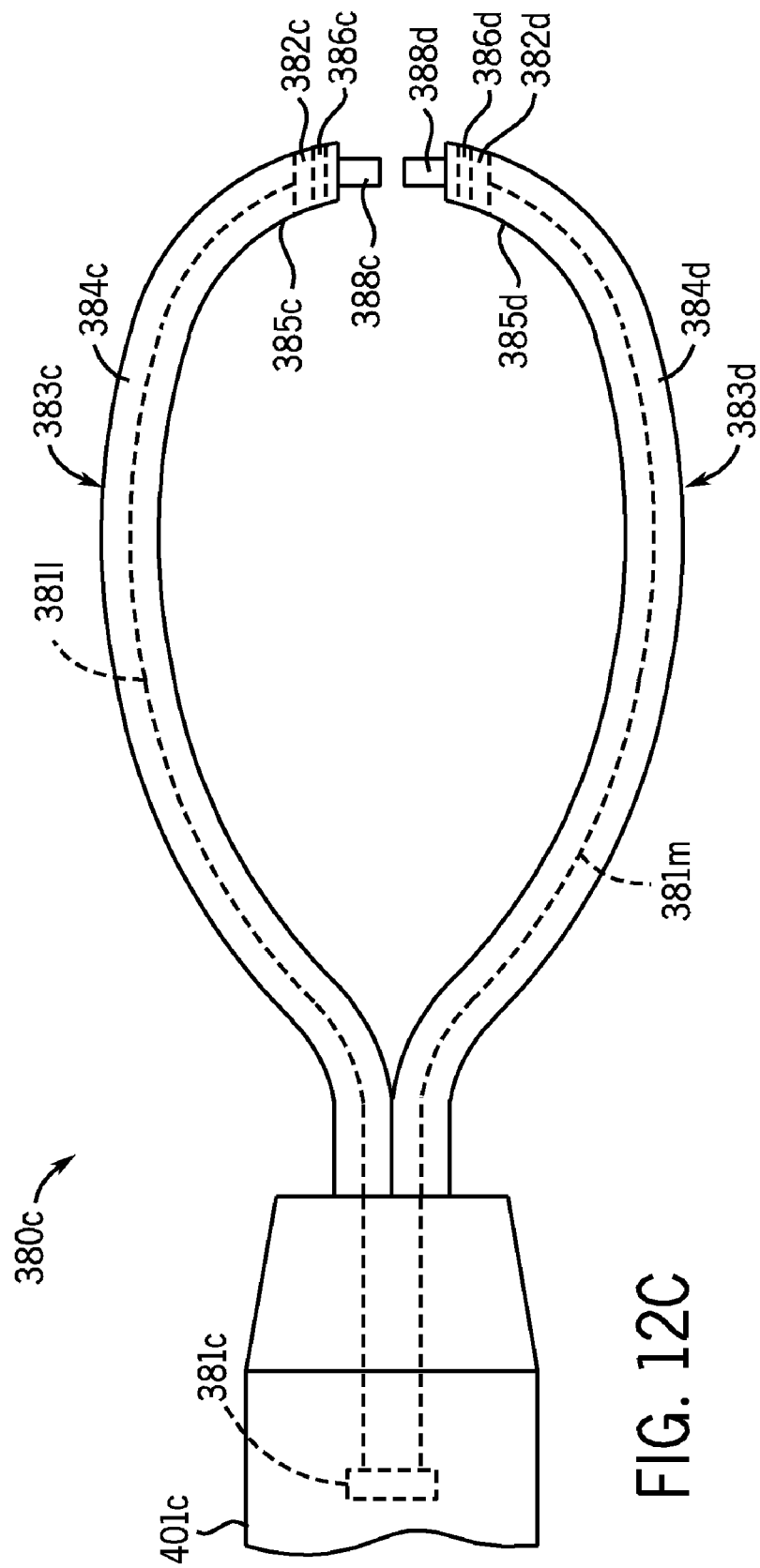
FIG. 12C is a top view of yet another version of a light curing device according to the invention.

Turning now to FIG. 12C, another example dental curing light 380c that may be used in the method of the invention will be now be described in further detail. The dental curing light 380c includes an electrical power supply 381c (such as batteries) and light sources 382c, 382d in electrical communication by way of lines 381l, 381m with the electrical power supply 381c. The light sources 382c, 382d can be high intensity light emitting diodes as is known in the art. The dental curing light 380c can use the typical 400-500 nanometer wavelength that is used in curing light curable composite materials. The electrical power supply 381c is contained in a housing 401c. The dental curing light 380c includes a first light guide 383c having a first distal section 384c and a first distal end 385c. The dental curing light 380c also includes a second light guide 383d having a second distal section 384d and a second distal end 385d. The light source 382c is contained in the first distal end 385c of the first light guide 383c. Likewise, the light source 382d is contained in the second distal end 385d of the second light guide 383d.

A first light conducting optical fiber bundle 386c conducts light from the light source 382c to a first tip 388c which can extend about 3 millimeters beyond the sleeve 387c of the first light guide 383c. Likewise, a second light conducting optical fiber bundle 386d conducts light from the light source 382d to a second tip 388d which can extend about 3 millimeters beyond the second sleeve 387d of the second light guide 383d. Alternatively, the first light conducting optical fiber bundle 386c and the second light conducting optical fiber bundle 386d may be omitted from the dental curing light 380c and light may be emitted from the light sources 382c, 382d to the tips 388c, 388d and directly onto the tooth. By locating the light sources 382c, 382d near the end of the light guides 383c, 383d loss of light intensity and light scattering are minimized.

Figure 12D:
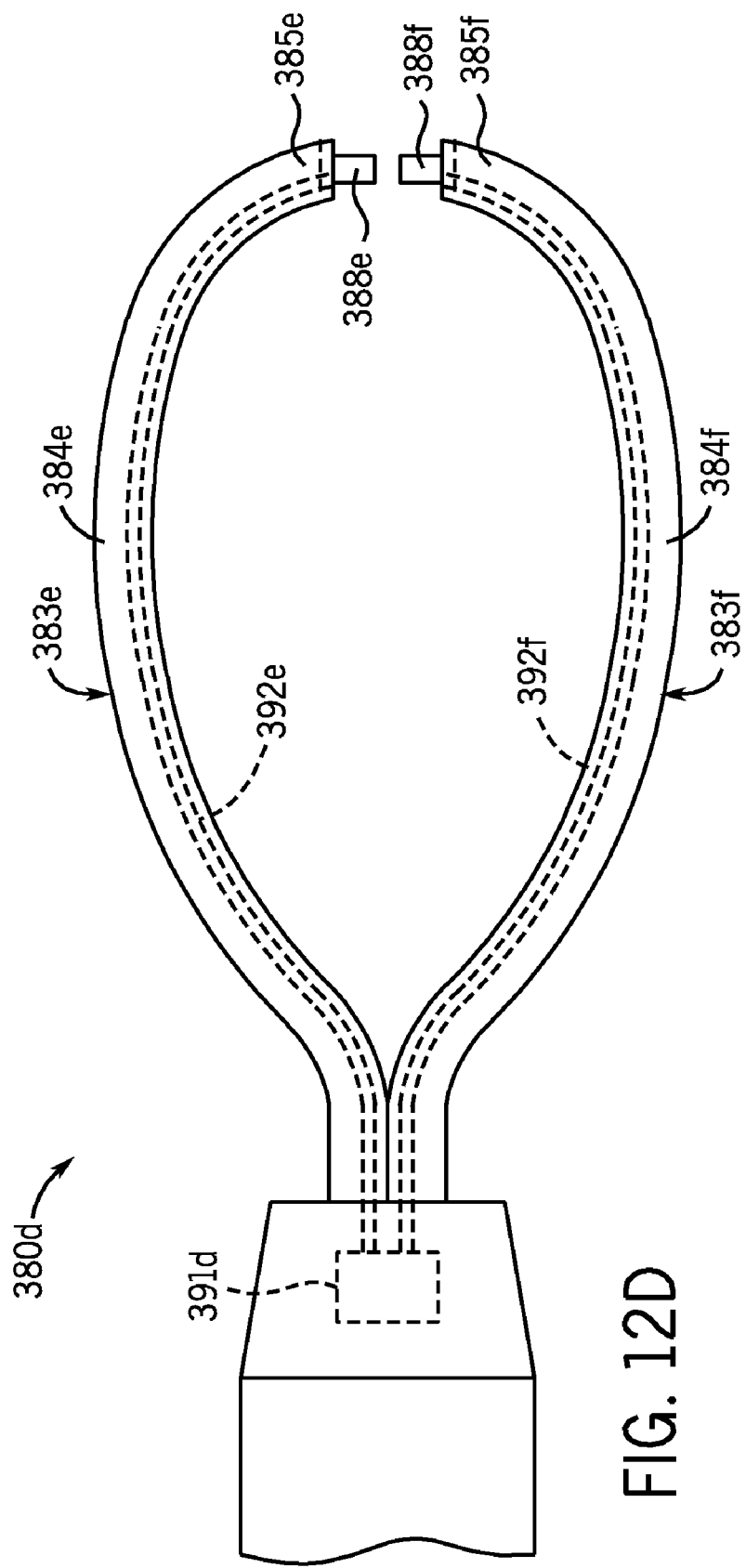
FIG. 12D is a top view of still another version of a light curing device according to the invention.

Turning now to FIG. 12D, another example dental curing light 380d that may be used in the method of the invention will be now be described in further detail. The dental curing light 380d includes an electrical power supply (not shown) and light sources (not shown) in electrical communication with the electrical power supply as in the dental curing light 380 of FIG. 12A. The dental curing light 380d includes a first light guide 383e having a first distal section 384e and a first distal end 385e. The dental curing light 380d also includes a second light guide 383f having a second distal section 384f and a second distal end 385f. A first light conducting optical fiber bundle conducts light from the light source to a first tip 388e of the first light conducting optical fiber. Likewise, a second light conducting optical fiber conducts light from the light source to a second tip 388f of the second light conducting optical fiber. In the dental curing light 380d, there is a fan 391d that is in fluid communication with a first fluid conduit 392e and a second fluid conduit 392f. The fan is powered by the electrical power supply. Flowing air from the fan 391d passes through the first fluid conduit 392e and exits the first distal end 385e of the first light guide 383e. Flowing air from the fan 391d also passes through the second fluid conduit 392f and exits the second distal end 385f of the second light guide 383f. When using the dental curing light 380d to cure restorative material in a cavity preparation, the flowing air contacts the tooth to provide a cooling effect. This eliminates heating of the tooth that results from photon collisions with the tooth.

Figure 12E:
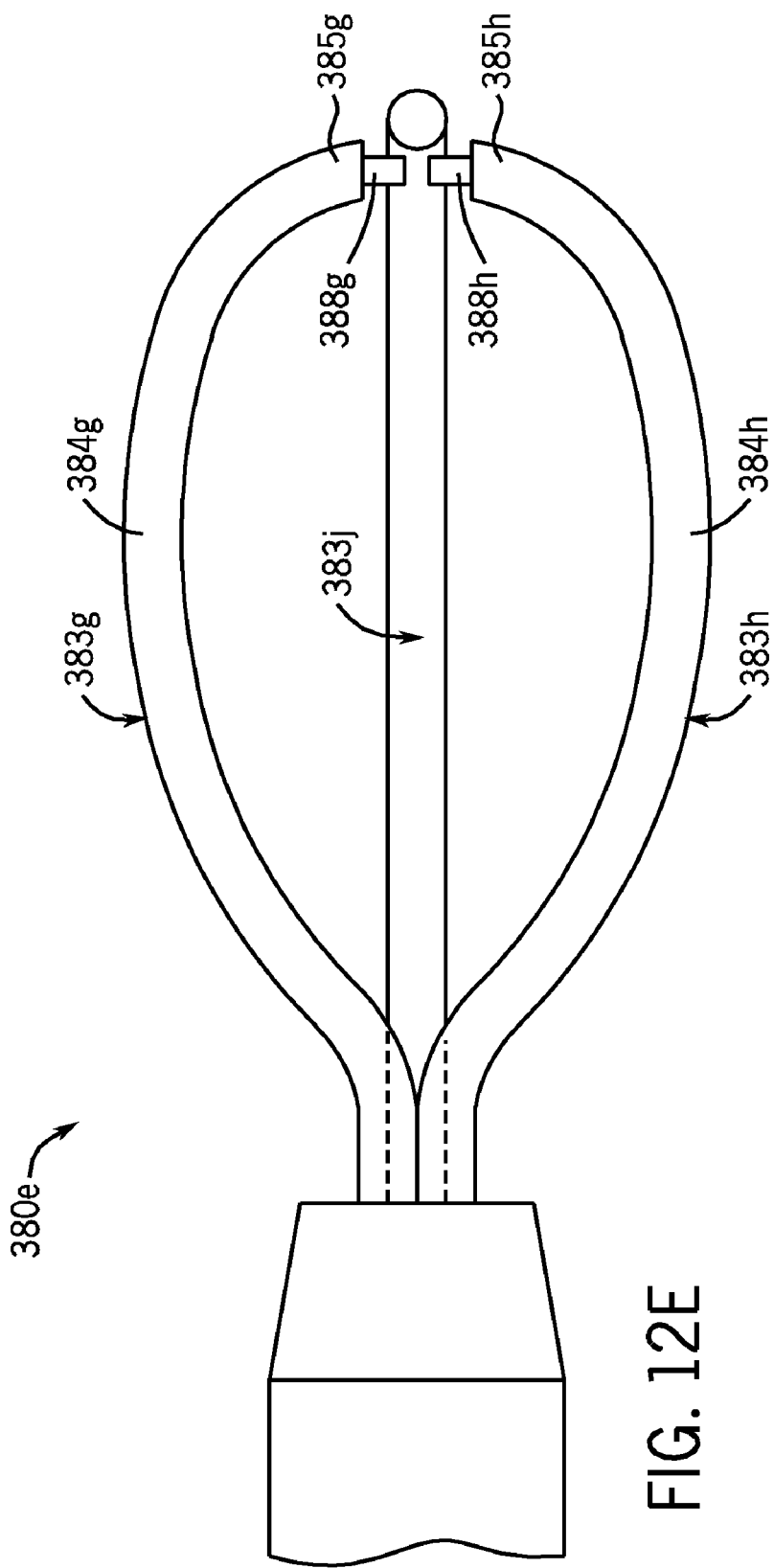
FIG. 12E is a bottom view of yet another version of a light curing device according to the invention.
Figure 12F:
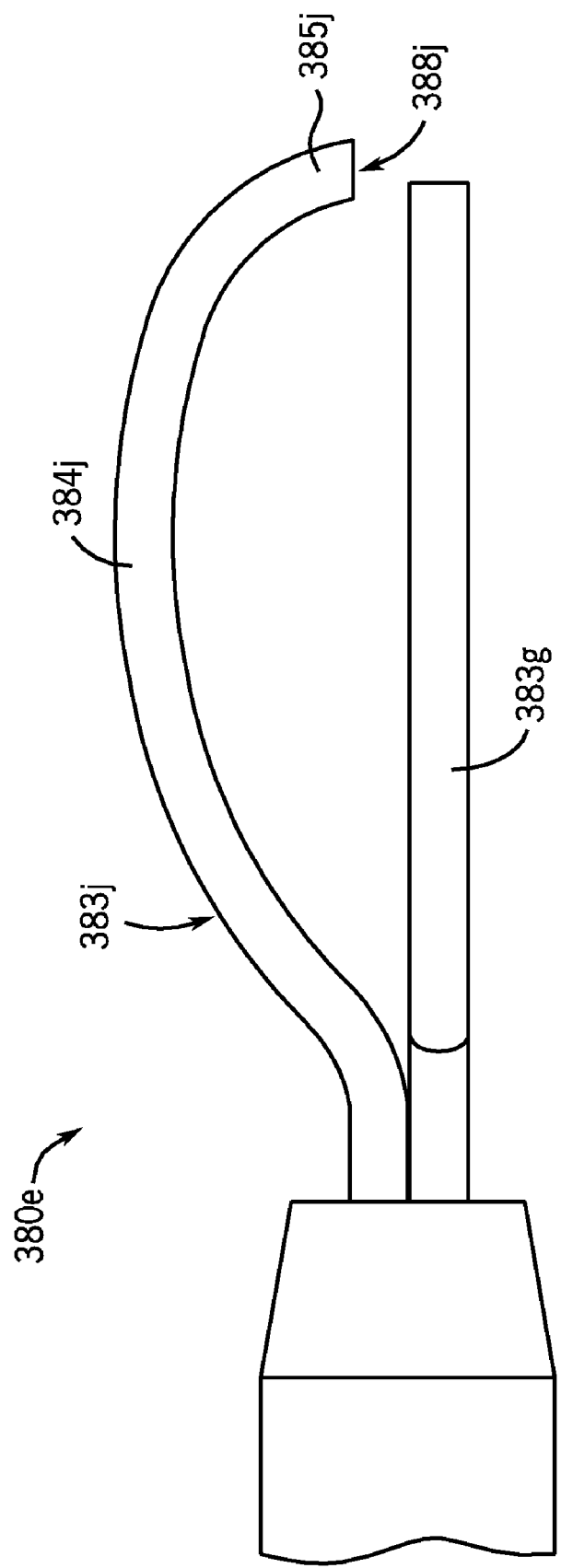
FIG. 12F is a side view of the light curing device of FIG. 12E.

Turning now to FIGS. 12E and 12F, another example dental curing light 380e that may be used in the method of the invention will be now be described in further detail. The dental curing light 380e includes an electrical power supply (not shown) and light sources (not shown) in electrical communication with the electrical power supply as in the dental curing light 380 of FIG. 12A. The dental curing light 380e includes a first light guide 383g having a first distal section 384g and a first distal end 385g. The dental curing light 380e also includes a second light guide 383h having a second distal section 384h and a second distal end 385h. In the dental curing light 380e, there is also a third light guide 383j having a third distal section 384j and a third distal end 385j. A first light conducting optical fiber bundle conducts light from the light source to a first tip 388g of the first light conducting optical fiber. Likewise, a second light conducting optical fiber bundle conducts light from the light source to a second tip 388h of the second light conducting optical fiber. Likewise, a third light conducting optical fiber conducts light from the light source to an end 388j of the third light conducting optical fiber. The first light guide 383g and the second light guide 383h are used to cure buccal and lingual portions of the restorative material as described above with reference to FIG. 12A. The third light guide 383j is used to cure occlusal portions of the restorative material.

Figure 12G:
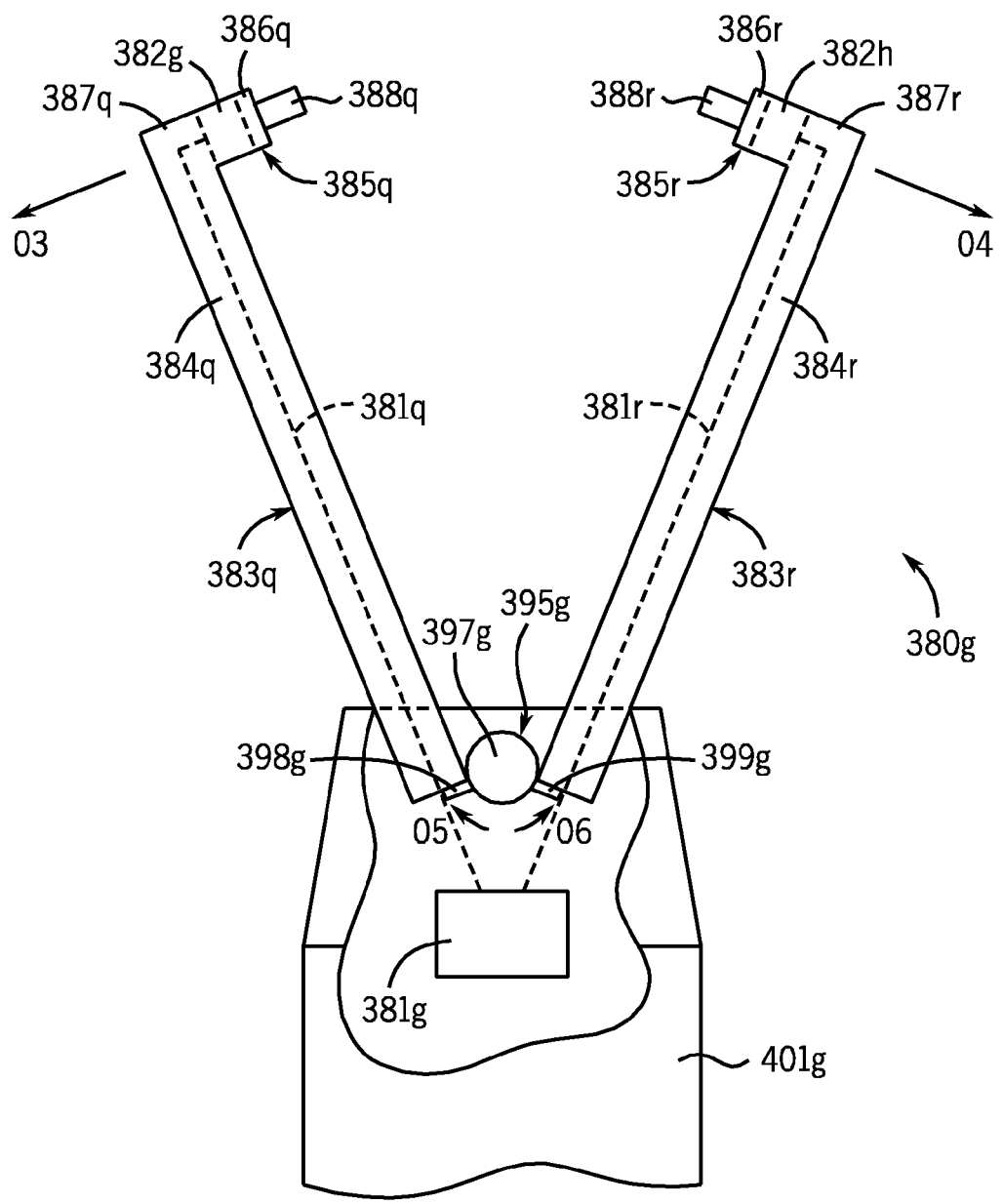
FIG. 12G is a top view of yet another version of a light curing device according to the invention.

Turning now to FIG. 12G, yet another example dental curing light 380g that may be used in the method of the invention will be now be described in further detail. The dental curing light 380g includes an electrical power supply 381g (such as batteries) and light sources 382g, 382h in electrical communication by way of lines 381q, 381r with the electrical power supply 381g. The light sources 382g, 382h can be high intensity light emitting diodes as is known in the art. The dental curing light 380g can use the typical 400-500 nanometer wavelength that is used in curing light curable composite materials. The electrical power supply 381g is contained in a housing 401g. The dental curing light 380c includes a first generally L-shaped light guide 383q having a first distal section 384q and a first distal end 385q. The dental curing light 380c also includes a second generally L-shaped light guide 383r having a second distal section 384r and a second distal end 385r. The light source 382g is contained in the first distal end 385q of the first light guide 383q. Likewise, the light source 382h is contained in the second distal end 385r of the second light guide 383r.

A first light conducting optical fiber bundle 386q conducts light from the light source 382g to a first tip 388q. The first tip 388q extends about 3 millimeters beyond the sleeve 387q of the first light guide 383q. Likewise, a second light conducting optical fiber 386r conducts light from the light source 382h to a second tip 388r. The second tip 388r of extends about 3 millimeters beyond the second sleeve 387r of the second light guide 383r. Alternatively, the first light conducting optical fiber bundle 386q and the second light conducting optical fiber bundle 386r may be omitted from the dental curing light 380g and light may be emitted from the light sources 382q, 382r to the tips 388q, 388r and directly onto the tooth. By locating the light sources 382q, 382r near the end of the light guides 383q, 383r loss of light intensity and light scattering are minimized.

In the dental curing light 380g, the first light guide 383q and the second light guide 383r are mounted on a hinge assembly 395g such that the first light guide 383q may pivot in direction O3 shown in FIG. 12G and the second light guide 383r may pivot in direction O4 shown in FIG. 12G. The hinge assembly 395g includes a central pivot pin 397g in the middle of a helical torsion spring that has a first leg 398g that biases the first light guide 383g in direction O5 and a second leg 399g that biases the second light guide 383r in direction O6 as shown in FIG. 12G.

The dental curing light 380g can be used in a method for the restoration of a tooth having a hollow cavity preparation in an interproximal surface of the tooth. In the method, a light-curable restorative material is placed in the cavity preparation. The first light guide 383q and the second light guide 383r can be flexed outward in directions O3 and O4 respectively as described with reference to FIG. 12G and thereafter the first light guide 383q and the second light guide 383g are released such that the first tip 388q of the dental curing light 380g assumes a position near a buccal portion of the restorative material in the cavity preparation (preferably at a distance of less than 6 millimeters, most preferably at 3-4 millimeters) and the second tip 388r of the dental curing light 380g assumes a position near a lingual portion of the restorative material in the cavity preparation (preferably at a distance of less than 6 millimeters, most preferably at 3-4 millimeters).

Turning now to FIG. 12H, another example dental curing light 380h that may be used in the method of the invention will be now be described in further detail. The dental curing light 380h includes an electrical power supply 381h (such as batteries) and light sources 382s, 382t, 382u in electrical communication by way of line 381x with the electrical power supply 381h. The light sources 382s, 382t, 382u can be high intensity light emitting diodes as is known in the art. The dental curing light 380h can use the typical 400-500 nanometer wavelength that is used in curing light curable composite materials. The electrical power supply 381h is contained in a housing 401h. The dental curing light 380h includes an tubular extension arm 383h having a distal section 384h and a distal end 385h. At the distal end 385h of the extension arm 383h, there is located an arch-shaped support 387h on which light sources 382s, 382t, 382u are mounted. In the embodiment of FIGS. 12H and 12I, the included angle A between the distal section 384h and the distal end 385h is about 90 degrees; however, the included angle between the distal section 384h and the distal end 385h can be about 30 degrees to about 150 degrees, preferably about 60 degrees to about 120 degrees. In the side view of FIG. 12H, the arch-shaped support 387h has a generally U-shaped perimeter; however, other perimeter shapes, such as square, rectangular, V-shaped, oval, or circular, can be used. The support 387h has a base wall 388x, a first wall 389x extending from the base wall 388x, and a spaced second wall 390x extending from the base wall 388x. The base wall 388x is connected to the arm 383h. The arch-shaped support 387h can be rigid, or can be formed from a flexible material that retains its shape upon deforming. An example flexible material is one that includes deformable metal wires that retain their shape upon bending in a matrix of an elastomer such as silicone or polyurethane.

The dental curing light 380h can be used in a method for the restoration of a tooth having a hollow cavity preparation in an interproximal surface of the tooth. In the method, a light-curable restorative material is placed in the cavity preparation. The dental curing light 380h is positioned such that the light source 382s assumes a position near a buccal portion of the restorative material in the cavity preparation (preferably at a distance of less than 9 millimeters), the light source 382t assumes a position near an occlusal portion of the restorative material in the cavity preparation (preferably at a distance of less than 9 millimeters), and the light source 382u assumes a position near a lingual portion of the restorative material in the cavity preparation (preferably at a distance of less than 9 millimeters).

Figure 16:
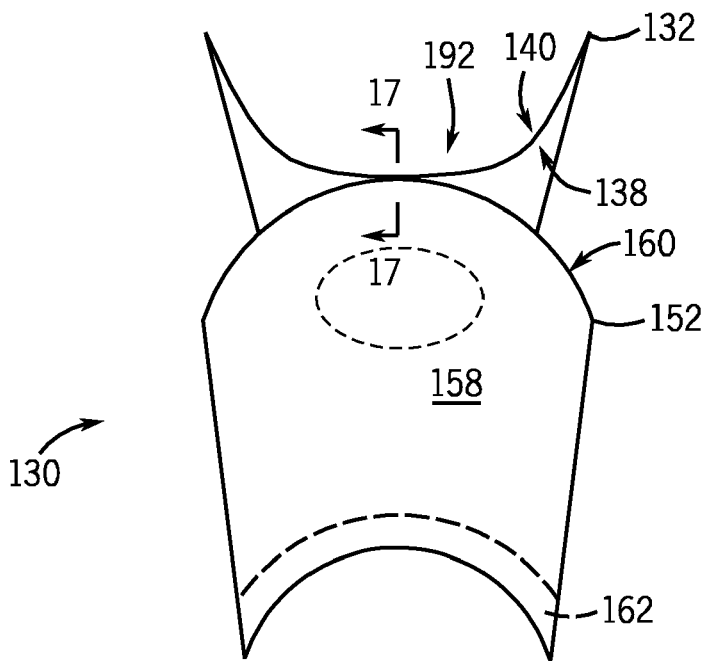
FIG. 16 is a top perspective view of another dental matrix according to the invention.
Figure 17:
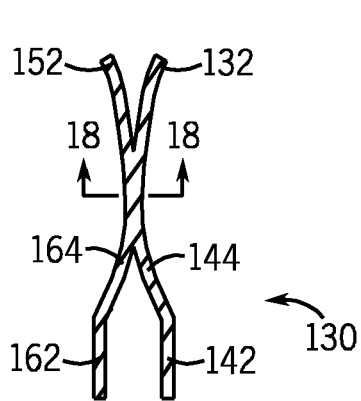
FIG. 17 is a cross-sectional view of the matrix of FIG. 16 taken along line 17-17 of FIG. 16.
Figure 18:
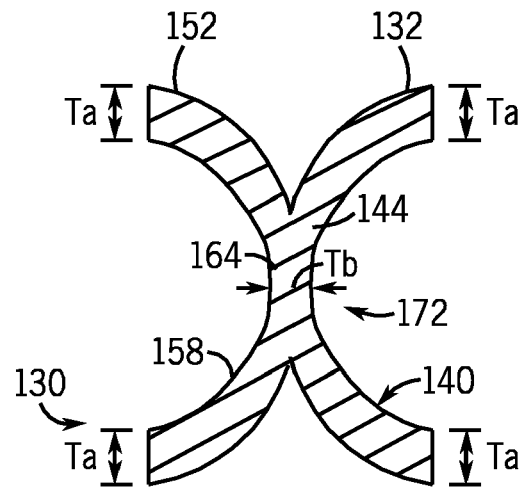
FIG. 18 is a cross-sectional view of the matrix of FIGS. 16 and 17 taken along line 18-18 of FIG. 17.

Turning to FIGS. 16-18, there is shown yet another embodiment of a sectional translucent (preferably transparent) anatomic dental matrix 130 which allows for the restoration of two approximating teeth simultaneously. In the dental matrix 130, there is a first strip 132 having a concave side surface 140 and a convex side surface 138 at planes horizontal to the first strip 132. The first strip 132 of the dental matrix 130 also has a base portion 142 and an upper portion 144 integral with and extending upward from the base portion 142 of the first strip 132. The horizontally concave side surface 140 forming the base portion 142 is not vertically concave, that is, a cross-section of the base portion 142 has parallel straight vertical walls that are normal to a bottom surface 146 of the first strip 132 (see FIG. 17). The horizontally concave side surface 140 forming the upper portion 144 of the first strip 132 is vertically concave (see FIG. 17).

In the dental matrix 130, there is also a second strip 152 having a concave side surface 158 and a convex side surface 160 at planes horizontal to the second strip 152. The second strip 152 of the dental matrix 130 also has a base portion 162 and an upper portion 164 integral with and extending upward from the base portion 162 of the second strip 152. The horizontally concave side surface 158 forming the base portion 162 is not vertically concave, that is, a cross-section of the base portion 162 has parallel straight vertical walls that are normal to a bottom surface 166 of the second strip 152 (see FIG. 17). The horizontally concave side surface 158 forming the upper portion 164 of the second strip 152 is vertically concave (see FIG. 17).

The first strip 132 and the second strip 152 are joined by fusing at a middle portion 172 of the dental matrix 130 at the upper portion 144 of the first strip 132 and the upper portion 164 of the second strip 152. The dashed oval in FIG. 16 shows an example area of fusion. The first strip 132 and the second strip 152 can be formed as separate pieces and fused together or molded as a single piece. Preferably, the dental matrix 130 is formed from a translucent (preferably transparent) material such as a polymeric film. One non-limiting example translucent material is the polyester film commercially available as Mylar™. Alternatively, the dental matrix 130 can be formed from a metallic material such as stainless steel or aluminum. The first strip 132 and the second strip 152 can be formed using the same or different materials.

Looking at FIG. 18, the ends of the first strip 132 and the second strip 152 have a material thickness Ta (which may be about 0.002-0.003 inches in an example embodiment). Moving toward the middle portion 172 of the dental matrix 130, the thickness of the first strip 132 and the second strip 152 tapers to a thickness Tb measured from the concave side surface 140 of the first strip 132 to the concave side surface 158 of the second strip 152. Preferably, the thickness Tb is less than two times the thickness Ta such that the dental matrix 130 can be more easily positioned between restoration of two approximating teeth. Most preferably, the thickness Tb equals the thickness Ta.

For example, in one form of the dental matrix 130, Ta can be about 0.002 inches and Tb can be about 0.002 inches. In other words, the contact area of the first strip 132 and the second strip 152 that is common to the first strip 132 and the second strip 152 will be the thickness of one sheet of strip (about 0.002 inches). This will mitigate the serious problem of back to back matrices that, when the matrices are removed, an open contact is created of 0.004 inches or more. In another form of the dental matrix 130, Ta can be about 0.002 inches and Tb can be about 0.001 inches. In other words, the contact area that is common to the first strip 132 and the second strip 152 will be less than the thickness of one strip, or less than 0.002 inches. In this case, only a minimal separation pressure will be needed. One non-limiting advantage of the thinner section where the two wings of the matrix join (or are shared) is to avoid the gapping that occurs when two matrix bands are placed back to back when restoring two decayed, approximating teeth simultaneously. The space taken by two thicknesses of a matrix dramatically increases the likelihood of an "open contact" where food becomes impacted and periodontal inflammation occurs.

When using the dental matrix 130 to restore two decayed, approximating teeth simultaneously, the placement of the interproximal dental matrix stabilizer 48 between approximating teeth occurs before the dental matrix 130 is inserted between the approximating teeth. The dentist stretches the dental matrix stabilizer 48 in directions A and B shown in FIG. 4. The dental matrix stabilizer 48 can be stretched by inserting the ends of a pliers in the first throughhole 58 and the second throughhole 59 of the dental matrix stabilizer 48 and opening the ends of the pliers. Alternatively, the dentist can grab and pull apart the end portions 51 and 52 of the dental matrix stabilizer 48 in directions A and B shown in FIG. 4. The stretching of the dental matrix stabilizer 48 leads to a decrease in vertical cross-section of the middle portion 53 of the dental matrix stabilizer 48 such that the dental matrix stabilizer 48 can be inserted between approximating teeth 12 and 24 by movement in direction C of FIG. 4. The dental matrix 130 can then be placed between approximating teeth 12 and 24 and the stretching tensile force on the dental matrix stabilizer 48 is released. As a result, the dental matrix stabilizer 48 biases the base portion 142 of the dental matrix 130 against the tooth 12 and the dental matrix stabilizer 48 biases the base portion 162 of the dental matrix 130 against the tooth 24. In one example, the matrix 130 is positioned in a four handed operation in which the double sided matrix 130 is inserted by one person as the other clinical person stretches the stabilizer 48 to allow the double sided matrix 130 to seat, then the stabilizer 48 is released and relaxes into proper position. Alternatively, one or two clear stabilizing wedges can be inserted after the matrix 130 is placed.

Figure 19:
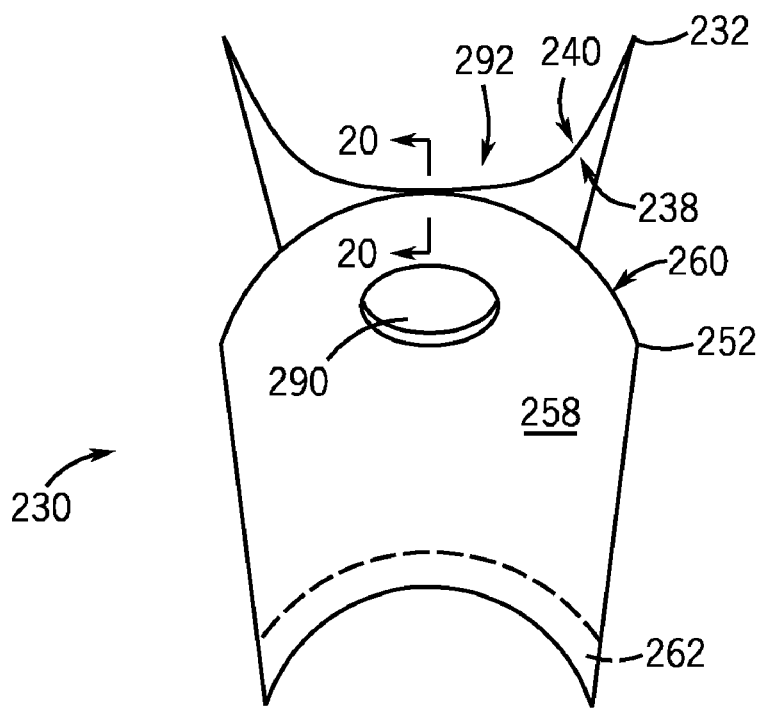
FIG. 19 is a top perspective view of yet another dental matrix according to the invention.
Figure 20:
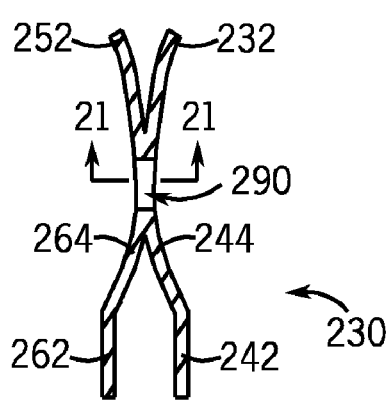
FIG. 20 is a cross-sectional view of the matrix of FIG. 19 taken along line 20-20 of FIG. 19.
Figure 21:
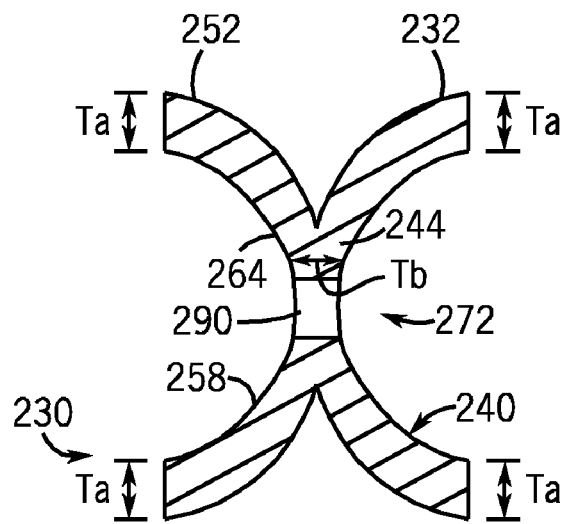
FIG. 21 is a cross-sectional view of the matrix of FIGS. 19 and 20 taken along line 21-21 of FIG. 20.

Turning to FIGS. 19-21, there is shown yet another embodiment of a sectional translucent (preferably transparent) anatomic dental matrix 230 which allows for the restoration of two approximating teeth simultaneously. In the dental matrix 230, there is a first strip 232 having a concave side surface 240 and a convex side surface 238 at planes horizontal to the first strip 232. The first strip 232 of the dental matrix 230 also has a base portion 242 and an upper portion 244 integral with and extending upward from the base portion 242 of the first strip 232. The horizontally concave side surface 240 forming the base portion 242 is not vertically concave, that is, a cross-section of the base portion 242 has parallel straight vertical walls that are normal to a bottom surface 246 of the first strip 232 (see FIG. 20). The horizontally concave side surface 240 forming the upper portion 244 of the first strip 232 is vertically concave (see FIG. 20).

In the dental matrix 230, there is also a second strip 252 having a concave side surface 258 and a convex side surface 260 at planes horizontal to the second strip 252. The second strip 252 of the dental matrix 230 also has a base portion 262 and an upper portion 264 integral with and extending upward from the base portion 262 of the second strip 252. The horizontally concave side surface 258 forming the base portion 262 is not vertically concave, that is, a cross-section of the base portion 262 has parallel straight vertical walls that are normal to a bottom surface 266 of the second strip 252 (see FIG. 20). The horizontally concave side surface 258 forming the upper portion 264 of the second strip 252 is vertically concave (see FIG. 20).

The first strip 232 and the second strip 252 are joined by fusing at a middle portion 272 of the dental matrix 230 at the upper portion 244 of the first strip 232 and the upper portion 264 of the second strip 252. The first strip 232 and the second strip 252 can be formed as separate pieces and fused together or molded as a single piece. The dental matrix 230 also includes an oval throughhole 290 that in one example can be a 2×3 millimeter oval. Other shapes are also possible for the throughhole 290. Preferably, the dental matrix 230 is formed from a translucent material such as a polymeric film. One non-limiting example translucent material is the polyester film commercially available as Mylar™. Alternatively, the dental matrix 230 can be formed from a metallic material such as stainless steel or aluminum.

Looking at FIG. 21, the ends of the first strip 232 and the second strip 252 have a material thickness Ta (which can be about 0.002-0.003 inches in an example embodiment). Moving toward the middle portion 272 of the dental matrix 230, the thickness of the first strip 232 and the second strip 252 tapers to a thickness Tb measured from the concave side surface 240 of the first strip 232 to the concave side surface 258 of the second strip 252. Preferably, the thickness Tb is less than two times the thickness Ta such that the dental matrix 230 can be more easily positioned between restoration of two approximating teeth. Most preferably, the thickness Tb equals the thickness Ta. One non-limiting advantage of the thinner section where the two wings of the matrix join is to avoid the gapping that occurs when two matrix bands are placed back to back when restoring two decayed, approximating teeth simultaneously. The space taken by two thicknesses of a matrix dramatically increases the likelihood of an "open contact" where food becomes impacted and periodontal inflammation occurs.

When using the dental matrix 230 to restore two decayed, approximating teeth simultaneously, the placement of the interproximal dental matrix stabilizer 48 between approximating teeth occurs before the dental matrix 230 is inserted between the approximating teeth. The dentist stretches the dental matrix stabilizer 48 in directions A and B shown in FIG. 4. The dental matrix stabilizer 48 can be stretched by inserting the ends of a pliers in the first throughhole 58 and the second throughhole 59 of the dental matrix stabilizer 48 and opening the ends of the pliers. Alternatively, the dentist can grab and pull apart the end portions 51 and 52 of the dental matrix stabilizer 48 in directions A and B shown in FIG. 4. The stretching of the dental matrix stabilizer 48 leads to a thinning of the middle portion 53 of the dental matrix stabilizer 48 such that the dental matrix stabilizer 48 can be inserted between approximating teeth 12 and 24 by movement in direction C of FIG. 4. The dental matrix 230 can then be placed between approximating teeth 12 and 24 and the stretching force on the dental matrix stabilizer 48 is released. As a result, the dental matrix stabilizer 48 biases the base portion 242 of the dental matrix 230 against the tooth 12 and the dental matrix stabilizer 48 biases the base portion 262 of the dental matrix 230 against the tooth 24.

When using the dental matrix 230 to restore two decayed, approximating teeth simultaneously, the throughhole 290 will allow restorative material from both cavity preparations to unite. By applying a gentle force at the end of the procedure, the approximating teeth will separate along the cleavage plane. Alternatively, the dental matrix 230 can be cutaway, and the patient can be dismissed and the teeth will thereafter cleave (snap apart) with normal mastication to form a tight contact. This will assure that a strong tight tooth to tooth contact is created. Special offset shears can be used to cutaway the matrix 230 that would otherwise be locked onto teeth. Alternatively, a perforation can be created on the lingual side that will allow for easy removal of the dental matrix 230.

Figure 22:
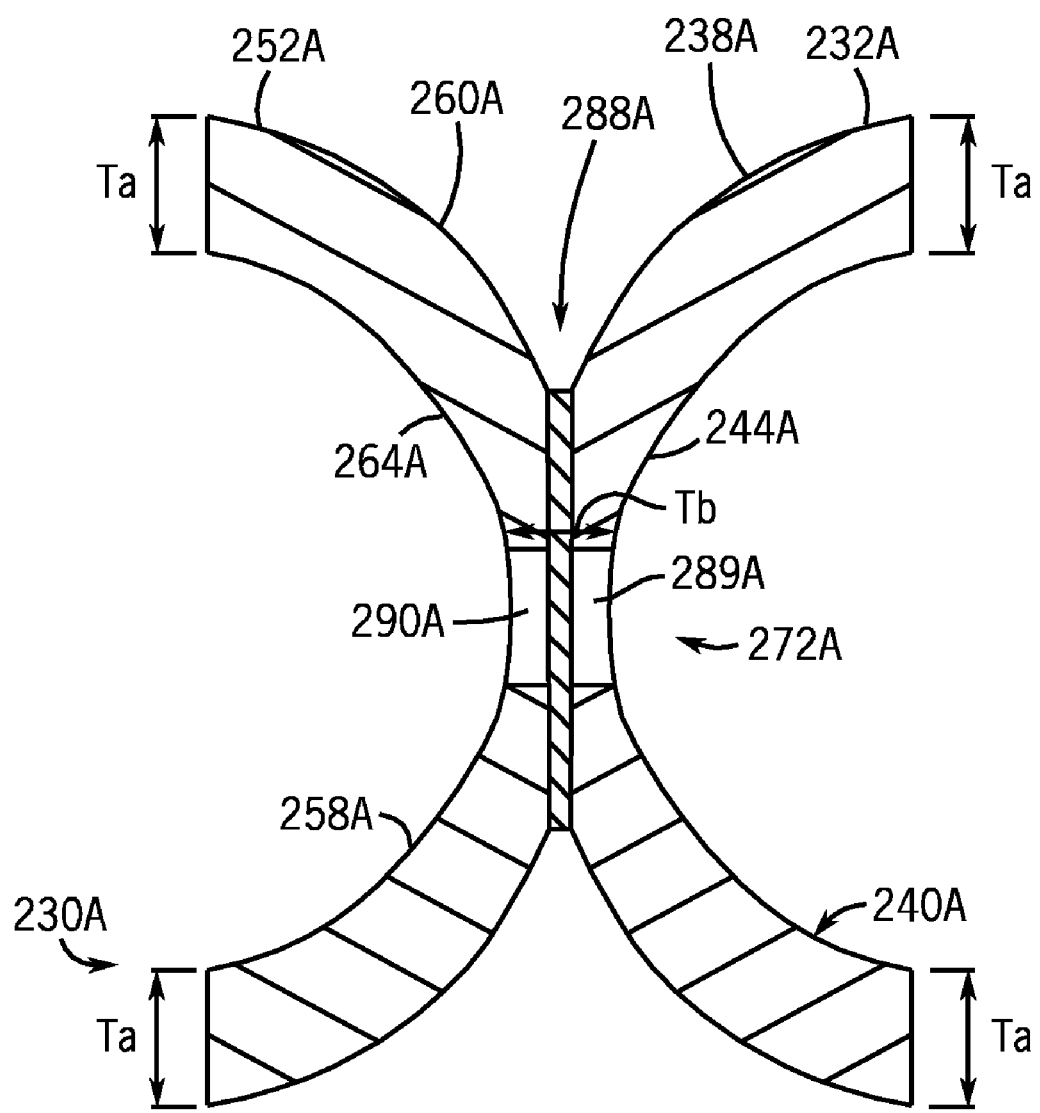
FIG. 22 is a cross-sectional view, similar to FIG. 21, of yet another dental matrix according to the invention.

Turning to FIG. 22, there is shown still another embodiment of a sectional translucent (preferably transparent) anatomic dental matrix 230A which allows for the restoration of two approximating teeth simultaneously. In the dental matrix 230A, there is a first strip 232A having a concave side surface 240A and a convex side surface 238A at planes horizontal to the first strip 232A. The first strip 232A of the dental matrix 230A also has a base portion (not shown, similar to 242 in FIG. 20) and an upper portion 244A integral with and extending upward from the base portion of the first strip 232A. The horizontally concave side surface 240A forming the base portion is not vertically concave, that is, a cross-section of the base portion has parallel straight vertical walls that are normal to a bottom surface of the first strip 232A. The horizontally concave side surface 240A forming the upper portion 244A of the first strip 232A is vertically concave.

In the dental matrix 230A, there is also a second strip 252A having a concave side surface 258A and a convex side surface 260A at planes horizontal to the second strip 252A. The second strip 252A of the dental matrix 230A also has a base portion (not shown, similar to 262 in FIG. 20) and an upper portion 264A integral with and extending upward from the base portion of the second strip 252A. The horizontally concave side surface 258A forming the base portion is not vertically concave, that is, a cross-section of the base portion has parallel straight vertical walls that are normal to a bottom surface of the second strip 252A. The horizontally concave side surface 258A forming the upper portion 264A of the second strip 252A is vertically concave.

The first strip 232A and the second strip 252A are joined by fusing at a middle portion 272A of the dental matrix 230A at the upper portion 244A of the first strip 232A and the upper portion 264A of the second strip 252A. The first strip 232A includes an oval throughhole 289A that in one example can be a 2×3 millimeter oval. The second strip 252A includes an oval throughhole 290A that in one example can be a 2×3 millimeter oval. The oval throughhole 289A and the oval throughhole 290A are aligned when the first strip 232A and the second strip 252A are joined by fusing. Other shapes are also possible for the throughholes 289A and 290A. When the first strip 232A and the second strip 252A are joined by fusing, a thin membrane 288A is positioned between the throughholes 289A and 290A and a portion of the first strip 232A and the second strip 252A. Preferably, the first strip 232A, the second strip 252A, and the membrane 288A are formed from a translucent material such as a polymeric film. One non-limiting example translucent material is the polyester film commercially available as Mylar™. Alternatively, the dental matrix 230A can be formed from a metallic material such as stainless steel or aluminum.

Looking at FIG. 22, the ends of the first strip 232A and the second strip 252A have a material thickness Ta (which can be about 0.002-0.003 inches in an example embodiment). Moving toward the middle portion 272A of the dental matrix 230A, the thickness of the first strip 232A and the second strip 252A tapers to a thickness Tb measured from the concave side surface 240A of the first strip 232A to the concave side surface 258A of the second strip 252A. Preferably, the thickness Tb is less than two times the thickness Ta such that the dental matrix 230A can be more easily positioned between restoration of two approximating teeth. Most preferably, the thickness Tb equals the thickness Ta. One non-limiting advantage of the thinner section where the two wings of the matrix join is to avoid the gapping that occurs when two matrix bands are placed back to back when restoring two decayed, approximating teeth simultaneously. The space taken by two thicknesses of a matrix dramatically increases the likelihood of an "open contact" where food becomes impacted and periodontal inflammation occurs.

Figure 23:
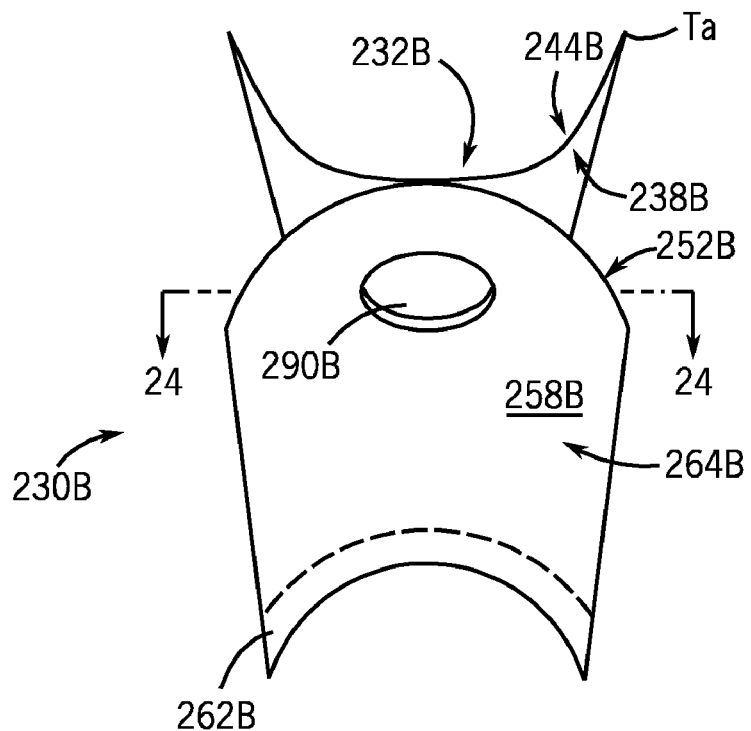
FIG. 23 is a top perspective view of still another dental matrix according to the invention.
Figure 24:
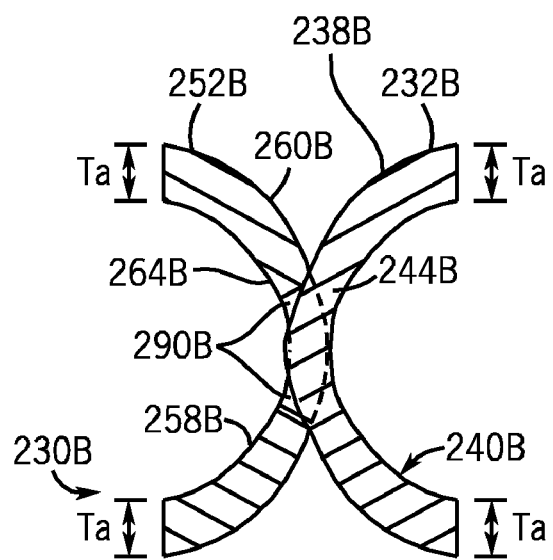
FIG. 24 is a cross-sectional view of the matrix of FIG. 23 taken along line 24-24 of FIG. 23.

Turning to FIGS. 23-24, there is shown yet another embodiment of a sectional translucent (preferably transparent) anatomic dental matrix 230B which allows for the restoration of two approximating teeth simultaneously. In the dental matrix 230B, there is a first strip 232B having a concave side surface 240B and a convex side surface 238B at planes horizontal to the first strip 232B. The first strip 232B of the dental matrix 230B also has a base portion (not shown, similar to 262B) and an upper portion 244B integral with and extending upward from the base portion of the first strip 232B. The horizontally concave side surface 240B forming the base portion is not vertically concave, that is, a cross-section of the base portion has parallel straight vertical walls that are normal to a bottom surface of the first strip 232B. The horizontally concave side surface 240B forming the upper portion 244B of the first strip 232B is vertically concave.

In the dental matrix 230B, there is also a second strip 252B having a concave side surface 258B and a convex side surface 260B at planes horizontal to the second strip 252B. The second strip 252B of the dental matrix 230B also has a base portion 262B and an upper portion 264B integral with and extending upward from the base portion of the second strip 252B. The horizontally concave side surface 258B forming the base portion is not vertically concave, that is, a cross-section of the base portion has parallel straight vertical walls that are normal to a bottom surface of the second strip 252B. The horizontally concave side surface 258B forming the upper portion 264B of the second strip 252B is vertically concave. Preferably, the first strip 232B and the second strip 252B are formed from a translucent material such as a polymeric film. One non-limiting example translucent material is the polyester film commercially available as Mylar™. Alternatively, the dental matrix 230B can be formed from a metallic material such as stainless steel or aluminum.

The second strip 252B includes an oval throughhole 290B that in one example can be about 2×3 millimeter oval. Other shapes are also possible for the throughhole 290B. When the first strip 232B and the second strip 252B are placed back to back, a section of the first strip 232B is positioned in the throughhole 290B of the second strip 252B. Looking at FIG. 24, the ends of the first strip 232B and the second strip 252B have a material thickness Ta (which can be about 0.002-0.003 inches in an example embodiment). When the first strip 232B and the second strip 252B are placed back to back, the thickness of the dental matrix 230B within the perimeter of the throughhole 290B will be the thickness of the first strip 232B, i.e., a single material thickness. One non-limiting advantage of the single material thickness within the perimeter of the throughhole 290B is to avoid the gapping that occurs when two matrix bands are placed back to back when restoring two decayed, approximating teeth simultaneously. The space taken by two thicknesses of a matrix dramatically increases the likelihood of an "open contact" where food becomes impacted and periodontal inflammation occurs. However, in the dental matrix 230B only a single material thickness within the perimeter of the throughhole 290B is present.

Referring now to FIGS. 25 to 28, there is shown the use of another alternative separator ring 410 according to the invention. The separator ring 410 has an arcuate body 412 having legs 414 and 416 that extend at a generally right angle from the body 412. Leg 414 has a disc-shaped end 415, and leg 416 has a disc-shaped end 417. In the relaxed position shown in FIGS. 26 and 27, there is a space between the legs 414 and 416. The body is preferably formed from stainless steel. However other elastic metallic and polymeric materials are suitable.

The separator ring 410 has a clamp 420 mounted on the end of the leg 414, and a clamp 422 mounted on the end of the leg 416. The clamp 420 has an inwardly directed outer surface 424 that slopes upward and outward from side walls 426, 428 of the clamp 420 and reaches a ridge 432. Likewise, the clamp 422 has an inwardly directed outer surface 434 that slopes upward and outward from side walls 436, 438 of the clamp 420 and reaches a ridge 439. Looking at FIG. 28, the bottom of the clamp 422 has an upwardly directed concavity 444. The bottom of the clamp 420 has a similar upwardly directed concavity (not shown). The upwardly directed concavity 444 allows the placement of a stabilizer with ends that do not separate (such as stabilizers 48d, 48g) under the upwardly directed concavity 444. The separator ring 410 also has an arcuate cover 456. The clamps 420, 422 and the cover 456 are preferably formed from a translucent elastomeric material such as a silicone or polyurethane elastomer.

Looking at FIG. 25, the clamp 422 of the separator ring 410 can be placed between the separate end members 63, 64 of the dental matrix stabilizer 48 with the ridge 439 directed inward toward the stabilizer 48 when the separator ring 410 is placed on the dental matrix stabilizer 48. The clamp 420 of the separator ring 410 can also be placed between the opposite side end members of the dental matrix stabilizer 48 in a similar fashion. The translucent (preferably transparent) elastomeric material of the clamps 420, 422 allows the passage of light to cure restorative material in the tooth 12.

Figure 29:
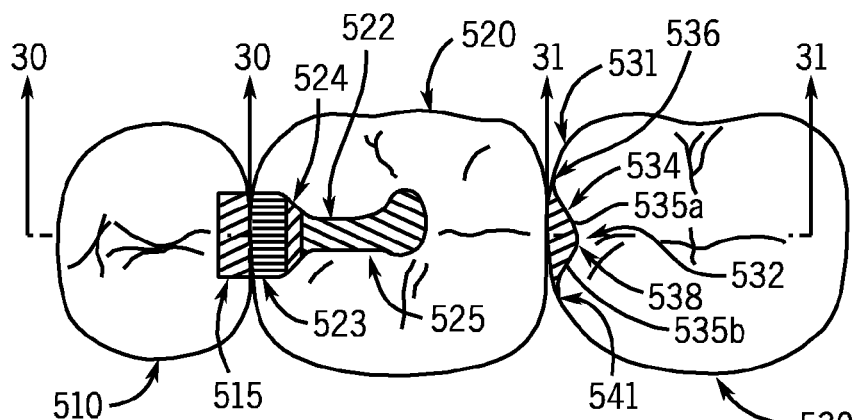
FIG. 29 is a top view of three adjacent teeth having three different cavity preparations.
Figure 30:
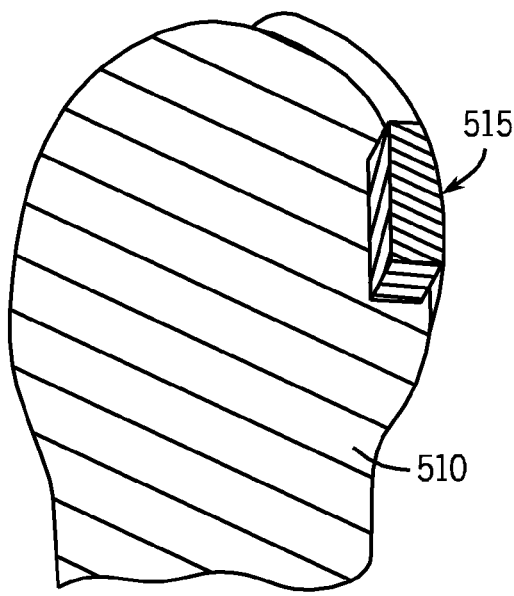
FIG. 30 is a cross-sectional view of a tooth of FIG. 29 taken along line 30-30 of FIG. 29.
Figure 31:
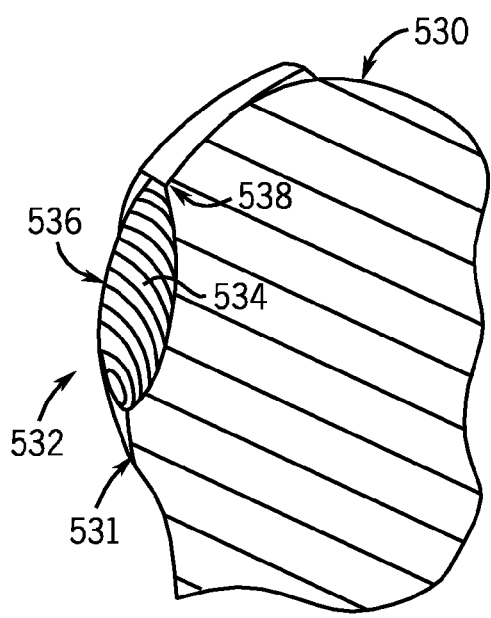
FIG. 31 is a cross-sectional view of a tooth of FIG. 29 taken along line 31-31 of FIG. 29.

Referring now to FIGS. 29-31, there is shown a top view of three adjacent teeth having three different cavity preparations. In tooth 510 of FIGS. 29 and 30, there is shown a conventional proximal box-shaped "slot" cavity preparation 515. In tooth 520 of FIG. 29, there is shown a conventional mesio-occlusal cavity preparation 522 having a first box shaped mesial section 523, a second intermediate section 524, and an inner extension 525. Typically, the distance from the occlusal to the floor of the mesial section 523 is greater than the distance from the occlusal to the floor of the intermediate section 524 which is greater than the distance from the occlusal to the floor of the inner extension 525. Often, the inner extension 525 may be described as having a dovetail shape.

Referring to FIGS. 29 and 31, a cavity preparation 532 according to the invention is shown in tooth 530 having an interproximal surface 531. In the occlusal view of FIG. 29, a surface 534 which will form the interface between the restorative material and the tooth has a serpentine outline 535a from the cavity margin 536 to an intermediate point 538 of the cavity preparation 532. Likewise, the surface 534 has a serpentine outline 535b from the cavity margin 541 to the intermediate point 538 of the cavity preparation 532. Looking at FIG. 31, the surface 534 slopes in a curvilinear manner from occlusal to gingival.

Other variations of the cavity preparation 532 can be prepared. The hollow cavity preparation 532 can be saucer shaped from buccal view and occlusal view. No mechanical retention is necessarily present in the cavity form as all retention is based on enamel adhesion, augmented with dentin adhesion. All margins are therefore knife edge and disappearing in nature versus the abrupt margins of current cavity designs. In another variation all of the margins, occlusal, gingival, buccal and lingual may have serpentine outlines. These margins provide additional adhesion and an even more pronounced knife edge, more invisible and better sealed filling margins.

Thus, the invention provides improved methods, dental matrices, dental wedges, interdental matrix stabilizers, dental separator rings, dental curing light devices, and kits for the restoration of a decayed portion of a tooth In the method, the filling material can be a single load of filling material that is cured in a single curing step in contrast to previous methods in which multiple two millimeter sections of filling material must be separately loaded and cured in multiple loading/curing steps. As a result, the method of the invention avoids the seams that are present between multiple two millimeter sections of filling material in prior methods.

Although the present invention has been described with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A dental curing light comprising:
    an electrical power supply;
    a first light guide in optical communication with at least one light source in electrical communication with the electrical power supply;
    a second light guide in optical communication with at least one light source in electrical communication with the electrical power supply,
    wherein the first light guide and the second light guide are connected to a housing, and
    wherein the first light guide and the second light guide are both hinged to the housing for movement with respect to the housing, and
    wherein the first light guide has a first distal tip, the second light guide has a second distal tip, and the first tip and the second tip are angled toward each other, and
    wherein the first light guide and the second light guide are normally biased by a spring into a relaxed position in which the first distal tip and the second distal tip are a first distance apart, and the first light guide and the second light guide have an outwardly flexed position in which the first distal tip and the second distal tip are a second distance apart, the second distance being greater than the first distance.

2. The dental curing light of claim 1 wherein:
    the first light guide and the second light guide are mounted on a hinge assembly including the spring.

3. The dental curing light of claim 1 wherein:
    the first distance is about 4 to about 15 millimeters.

4. The dental curing light of claim 1 wherein:
the first light guide is in optical communication with a first light source in electrical communication with the electrical power supply,
the second light guide is in optical communication with a second light source in electrical communication with the electrical power supply,
the first light source is located in the first distal end of the first light guide, and
the second light source is located in the second distal end of the second light guide.

5. The dental curing light of claim 1 further comprising:
a third light guide in optical communication with at least one light source in electrical communication with the electrical power supply.

6. The dental curing light of claim 1 wherein:
the dental curing light does not include structure in a light path between the first tip and the second tip.

7. A method for the restoration of a tooth having a hollow cavity preparation in an interproximal surface of the tooth, the method comprising:
(a) placing a light-curable restorative material in the cavity preparation;
(b) directing light from the first light guide of the dental curing light of claim 1 at a buccal portion of the restorative material in the cavity preparation; and
(c) simultaneously directing light from the second light guide of the dental curing light of claim 1 at a lingual portion of the restorative material in the cavity preparation.

8. A dental curing light comprising:
an electrical power supply;
a first light guide in optical communication with at least one light source in electrical communication with the electrical power supply;
a first light transmitting tip connected to a first distal end of the first light guide, the first tip including a first tip section having a diameter less than a diameter of the first distal end of the first light guide;
a second light guide in optical communication with at least one light source in electrical communication with the electrical power supply; and
a second light transmitting tip connected to a second distal end of the second light guide, the second tip including a second tip section having a diameter less than a diameter of the second distal end of the second light guide,
wherein the first light guide and the second light guide are both hinged to the housing for movement with respect to the housing, and
wherein the first tip and the second tip are angled toward each other, and
wherein the first light guide and the second light guide are normally biased by a spring into a relaxed position in which the first distal tip and the second distal tip are a first distance apart, and the first light guide and the second light guide have an outwardly flexed position in which the first distal tip and the second distal tip are a second distance apart, the second distance being greater than the first distance.

9. The dental curing light of claim 8 wherein:
the first light guide is in optical communication with a first light source in electrical communication with the electrical power supply, and
the second light guide is in optical communication with a second light source in electrical communication with the electrical power supply.

10. The dental curing light of claim 9 wherein:
the first light source is located in the first distal end of the first light guide, and
the second light source is located in the second distal end of the second light guide.

11. The dental curing light of claim 8 wherein:
the first tip includes a first light transmitting section extending laterally from a base of the first tip section, and
the second tip includes a second light transmitting section extending laterally from a base of the second tip section.

12. The dental curing light of claim 8 wherein:
at least one of the first distal end of the first light guide and the second distal end of the second light guide includes an opening in fluid communication with a source of flowing air.

13. The dental curing light of claim 8 further comprising:
a third light guide in optical communication with at least one light source in electrical communication with the electrical power supply.

14. The dental curing light of claim 13 wherein:
the third light guide directs light in a direction substantially perpendicular to the first light guide.

15. The dental curing light of claim 8 wherein:
the dental curing light does not include structure in a light path between the first tip and the second tip.

16. The dental curing light of claim 8 wherein:
the first light guide and the second light guide are are mounted on a hinge assembly including the spring.

* * * * *